United States Patent [19]
Moore et al.

[11] Patent Number: 5,985,828
[45] Date of Patent: Nov. 16, 1999

[54] MAMMALIAN RECEPTORS FOR INTERLEUKIN-10 (IL-10)

[75] Inventors: Kevin W. Moore, Palo Alto; Ying Liu, Mountain View; Alice Suk-Yue Ho, Milpitas; Di-Hwei Hsu, Palo Alto; J. Fernando Bazan, Menlo Park, all of Calif.; Jimmy C. Tan, Nutley; Chuan-Chu Chou, Westfield, both of N.J.

[73] Assignee: Schering Corporation, Kenilworth, N.J.

[21] Appl. No.: 08/472,097

[22] Filed: Jun. 7, 1995

Related U.S. Application Data

[60] Division of application No. 08/110,683, Aug. 23, 1993, Pat. No. 5,789,192, which is a continuation-in-part of application No. 08/011,066, Jan. 29, 1993, abandoned, which is a continuation-in-part of application No. 07/989,792, Dec. 10, 1992, abandoned.

[51] Int. Cl.$^6$ .................. C12N 15/12; C07K 14/715; A61K 38/16
[52] U.S. Cl. .................. 514/12; 514/2; 514/8; 530/350; 530/395; 530/402; 530/387.1; 530/387.9; 435/69.1; 435/69.7; 435/471; 435/325; 435/71.1; 435/320.1; 435/252.3; 424/184.1; 424/185.1
[58] Field of Search .................. 536/23.5; 435/69.1, 435/69.5, 240.1, 320.1, 252.3, 69.7, 471, 325, 71.1; 530/350, 395, 402, 387.1, 387.9; 514/2, 8, 12; 424/84, 184.1, 185.1

[56] References Cited

PUBLICATIONS

J. Fernando Bazan, "Structural design and molecular evolution of a cytokine receptor superfamily," *PNAS*, vol. 87, pp. 6934–6938, Sep. 1990.
René de Waal Malefyt, et al., "Interleukin 10 (IL–10) Inhibits Cytokine Synthesis by Human Monocytes: An Autoregulatory Role of IL–10 Produced by Monocytes," *J. Exp. Med.*, vol. 174, pp. 1209–1220, Nov. 1991.
David F. Fiorentino, et al., "IL–10 Inhibits Cytokine Production by Activated Macrophages," *J. Immunol.*, vol. 147, pp. 3815–3822, 1991.
David F. Fiorentino, et al., "Two Types of Mouse T Helper Cell IV. Th2 Clones Secrete a Factor that Inhibits Cytokine Production by Th1 Clones," *J. Exp. Med.*, vol. 170, pp. 2081–2095, Dec. 1989.
David P. Gearing, et al., "Expression cloning of a receptor for human granulocyte–macrophage colony–stimulating factor," *The EMBO Journal*, vol. 8, No. 12, pp. 3667–3676, 1989.
Kazuhiro Hayashida, et al., "Molecular cloning of a second subunit of the receptor for human granulocyte–macrophage colony–stimulating factor (GM–CSF): Reconstitution of a high-affinity GM–CSF receptor," *PNAS*, vol. 87, pp. 9655–9659, Dec. 1990.
Di–Hwei Hsu, et al., "Differential effects of IL–4 and IL–10 on IL–2–induced IFN–γ synthesis and lymphokine–activated killer activity," *International Immunology*, vol. 4, No. 5, pp. 563–569, 1992.

Di–Hwei Hsu, et al., "Expression of Interleukin–10 Activity by Epstein–Barr Virus Protein BCRF1," *Science*, vol. 250, pp. 830–832, Nov. 1990.
Hiroshi Ishida, et al., "Continuous Anti–Interleukin 10 Antibody Administration Depletes Mice of Ly–1 B Cells but Not Conventional B Cells," *J. Exp. Med.*, vol. 175, pp. 1213–1220, May 1992.
Naoto Itoh, et al., "Cloning of an Interleukin–3 Receptor Gene: A Member of a Distinct Receptor Gene Family," *Science*, vol. 247, pp. 324–327, Jan. 1990.
Kevin W. Moore, et al., "Homology of Cytokine Synthesis Inhibitory Factor (IL–10) to the Epstein–Barr Virus Gene BCRFI," *Science*, vol. 248, pp. 1230–1234, Jun. 1990.
Tim R. Mosmann, et al., "The role of IL–10 in crossregulation of $T_h1$ and $T_h2$ responses," *Immunology Today*, vol. 12, pp. A49–A53, 1991.
Stephen P. Squinto, et al., "Identification of Functional Receptors for Ciliary Neurotrophic Factor on Neuronal Cell Lines and Primary Neurons," *Neuron*, vol. 5, pp. 757–766, Dec. 1990.
Jan Tavernier, et al., "A Human High Affinity Interleukin–5 Receptor (IL5R) Is Composed of an IL5–Specific α Chain and a β Chain Shared with the Receptor for GM–CSF," *Cell*, vol. 66, pp. 1175–1184, Sep. 20, 1991.
P. Vieira, et al., "Isolation and expression of human cytokine synthesis inhibitory factor cDNA clones: Homology to Epstein–Barr virus open reading frame BCRFI," *PNAS*, vol. 88, pp. 1172–1176, Feb. 1991.
C. –C. Chou, et al. "Interleukin–10 Receptor: Detection and Characterization on Human and Mouse Cell Lines," Abstract No. 350 *FASEB Journal* American Society of Biochemistry & Molecular Biology & Division of Biological Chemistry—American Chemical Society: Joint Meeting San Diego, CA May 30–Jun. 3, 1993.
David Cosman, "The Hematopoietin Receptor Superfamily," *Cytokine*, 5(2):95–106, 1993.
R.S. Kaczmarski, et al. "The Cytokine Receptor Superfamily," *Blood Reviews*, 5(3):193–203, 1991.
Jimmy C. Tan, et al. "Characterization of Interleukin–10 Receptors on Human and Mouse Cells," *J. of Biol. Chem.* 268(28):21053–21059, 1993.
Miyajima et al Annu. Rev. Immunol 10, 295, 1992.
Farrar et al.Annu. Rev. Immunol 11, 571, 1993.
Greve et al Cell 31, 749, 1982.
Holmes et al J. Immunol. 139, 936, 1987.
Kayano et al 1988 (FEBS lett. 228:187).
Dasgupta et al 1987 (PNAS USA 84, 1094).
Muller et al 1983 Human Immunol 6, 189.

*Primary Examiner*—Prema Mertz
*Attorney, Agent, or Firm*—Sheela Mohan-Peterson; Edwin P. Ching

[57] ABSTRACT

Receptor components for IL-10 are isolated and characterized. The amino acid sequence and nucleic acid encoding various species variants of the receptors are disclosed. Uses of the purified receptor gene and polypeptide are disclosed, including means for screening for agonists and antagonists of the receptor ligands, for producing diagnostic or therapeutic reagents, and for producing antibodies. Therapeutic or diagnostic reagents and kits are also provided.

23 Claims, 30 Drawing Sheets

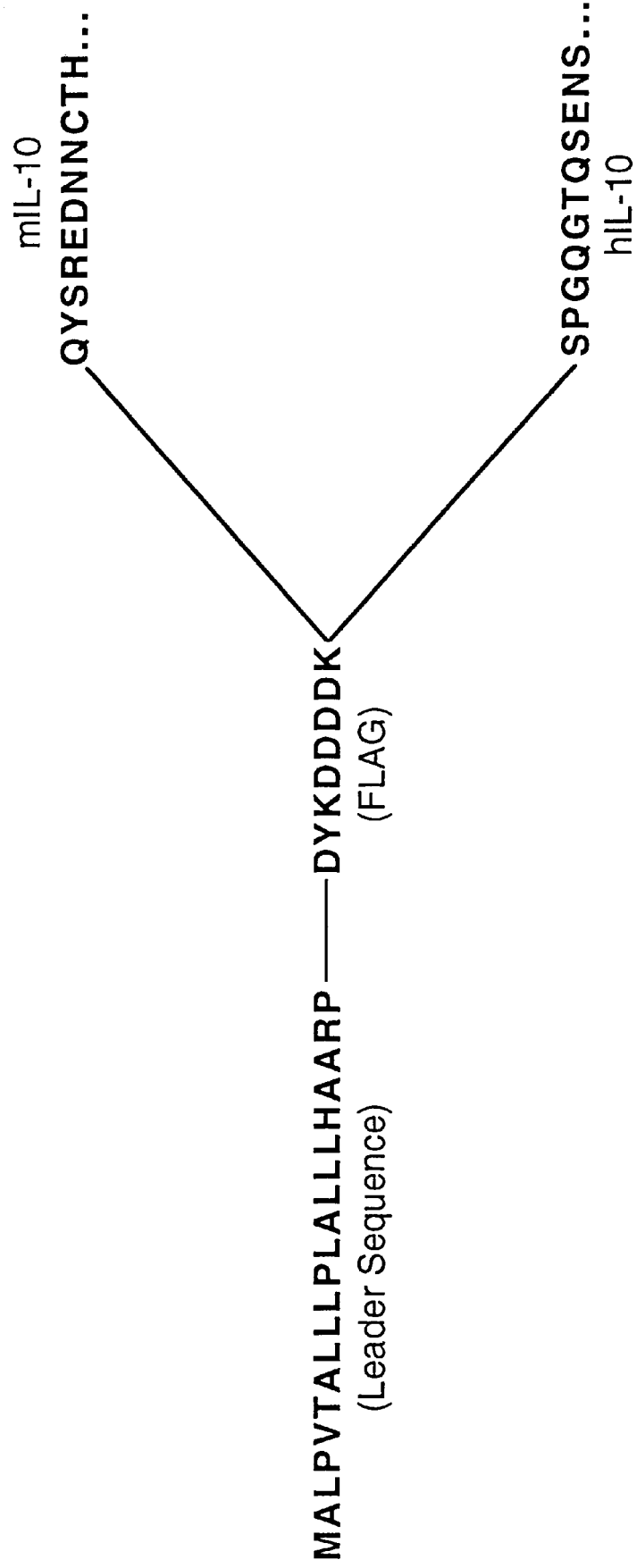

MC9: mouse mast cells
J774: mouse macrophage

<u>FACS was used to enrich for higher expression variants</u>

MAMMALIAN RECEPTORS FOR INTERLEUKIN-10 (IL-10)

CROSS REFERENCE TO RELATED APPLICATIONS

This is a divisional of U.S. Pat. application Ser. No. 08/110,683, filed 23 Aug. 1993, now U.S. Pat. No. 5,789,192, which is a continuation-in-part of U.S. Pat. application Ser. No. 08/011,066, filed 29 Jan. 1993, now abandoned, which is a continuation-in-part of U.S. Pat. application Ser. No 07/989,792, filed 10 Dec. 1992, now abandoned.

FIELD OF THE INVENTION

The present invention relates generally to nucleic acids and polypeptides characteristic of receptors for mammalian interleukin-10, and more particularly to their uses in preparing reagents useful for diagnosing or treating various receptor-related medical conditions.

BACKGROUND OF THE INVENTION

Activated hemopoietic cells secrete numerous proteins. Cytokines are a subset of these proteins and play a variety of important roles in regulation of immune responses by controlling proliferation, differentiation, and the effector functions of immune cells. Most cytokines have more than one biological activity and which activity is the most important likely depends on the local context in which the cytokine is produced.

These cytokines are intercellular signaling molecules whose actions are typically mediated through specific receptor molecules found on target cells. The structure and mechanism of action of these receptors on target cells is not well understood, though many are composed of at least two separate proteins. These earlier described heterodimeric receptors are often composed of polypeptides which are related both to each other and to receptors for other cytokines. Components of receptors for other cytokines have been described. See, e.g., Gearing, et al. (1989) *EMBO J.* 8:3667–3676 (low affinity α chain of a human GM-CSF receptor); Itoh, et al. (1990) *Science* 247:324–327 (low affinity α chain of a mouse IL-3 receptor); and Hayashida, et al. (1990) *Proc. Nat'l Acad. Sci. USA* 87:9655–9659 (a β chain of a human GM-CSF receptor); and Tavernier, et al. (1991) *Cell* 66:1175–1184 (IL-5 receptor, α and β chains). The various components of the earlier identified receptors appear to share properties useful in defining a receptor superfamily of related proteins. See, e.g., Bazan (1990) *Immunology Today* 11:350–354; and Bazan (1990) *Proc. Nat'l Acad. Sci. USA* 87:6934–6938. However, the structure and mechanism of action of a receptor for a mammalian interleukin-10 (IL-10) could not be predicted with reliability based merely upon speculated similarity to receptors for other cytokines.

As soluble intercellular messenger molecules, the cytokines likely bind to cellular receptors, e.g., cell surface receptors. Receptor molecules have been identified and isolated for G-CSF, GM-CSF, EPO, TNF, IFN-γ, IL-2, IL-3, IL-4, IL-5, IL-6, and IL-7. Many of these receptors have two chains, both of which are members of the hemopoietic receptor superfamily. In such cases, typically one chain, designated the a chain, can bind its ligand with low affinity. This interaction may or may not result in transduction to the cell of a signal. Another chain, designated the β chain, when associated with the α chain, confers higher affinity binding of the heterodimeric receptor to the cytokine. The β chain by itself usually lacks significant ligand binding affinity. The dimeric form of receptor is capable of transducing a signal into the cell as a consequence of ligand, e.g., cytokine, binding. However, any similarity between the structural and functional features of those receptors generally and a receptor for IL-10 is speculative. Additional subunits may also be associated with the receptors.

A cytokine synthesis inhibitory factor (CSIF) activity led to assays which allowed the isolation of a cytokine designated interleukin-10 (IL-10). See Fiorentino, et al. (1989) *J. Exptl. Med.* 170:2081–2095; and Mosmann, et al. (1991) *Immunol. Today* 12:A49–A53. Both mouse and human counterparts have been isolated. See Moore, et al. (1990) *Science* 248:1230–1234; and Vieira, et al. (1991) *Proc. Nat'l Acad. Sci. USA* 88:1172–1176. A human viral analog, known as either vIL-10 or BCRF1, has been described which shares many characteristic activities of the natural human form. See Hsu, et al. (1990) *Science* 250:830–832. Another viral homolog has been described from an equine herpes virus. See Rode, et al. (1993) *Virus Genes* 7:111–116.

Human IL-10 (hIL-10) has an N-terminal hydrophobic signal sequence of 18 amino acids, one potential N-linked glycosylation site, 4 cysteine residues, and seven methionine residues. It shares strong DNA and amino acid sequence homology with mouse IL-10 and an open reading frame in Eppstein-Barr virus, BCRF1, and an open reading frame in an equine herpes virus, type II. It inhibits cytokine synthesis by activated T cells, stimulates growth for thymocytes and mast cells, induces class II MHC expression, and sustains viability in culture of small dense resting mouse B cells. A mouse counterpart has also been described, and equivalent proteins would be found in other mammalian species. IL-10 binding to cell surface receptors is thought to be an initiating step for various specific cellular responses, as described below.

One means to modulate IL-10 effect upon binding to its receptor, and therefore potentially useful in treating inappropriate immune responses, e.g., autoimmune, inflammation, sepsis, and cancer situations, is to inhibit the receptor signal transduction. Unfortunately, finding reagents capable of serving as an antagonist or agonist has been severely hampered by the absence of large quantities of IL-10 receptor, preferably purified and in an active form. In order to characterize the structural properties of the IL-10 receptor in greater detail and to understand the mechanism of action at the molecular level, purified receptor will be very useful.

Moreover, similarities to other cytokine functions exist. In particular, the IL-10 receptor likely shares many functions and characteristics with other receptors, but also exhibits different structural and functional properties. The receptors provided herein, by comparison to other receptors or by combining structural components, will provide further understanding of signal transduction induced by ligand binding.

The isolated receptor gene should provide means to generate an economical source of the receptor, allow expression of more receptors on a cell leading to increased assay sensitivity, promote characterization of various receptor subtypes and variants, and allow correlation of activity with receptor structures. Moreover, fragments of the receptor may be useful as agonists or antagonists of ligand binding. See, e.g., Harada, et al. (1992) *J. Biol. Chem.* 267:22752–22758.

Thus, a need exists for the isolation and characterization of nucleic acids encoding components of receptors for IL-10. The present invention provides these and the means for preparing many other useful reagents.

SUMMARY OF THE INVENTION

The present invention provides nucleic acid and protein sequences of components of a receptor for IL-10. Both a human IL-10 receptor component and a mouse counterpart are exemplified, though equivalent components from other mammalian species will be found by similar methods or based upon other properties derived therefrom.

The present invention provides recombinant or isolated nucleic acids comprising a sequence exhibiting homology to a sequence encoding a mammalian receptor for IL-10, a fragment thereof, or a unique portion thereof. In preferred embodiments, the nucleic acids will comprise deoxyribonucleic acid, will be isolated, further comprise a regulatory sequence from the 5' or 3' sequence adjacent a gene encoding a receptor for IL-10, or are operably linked to a genetic control element. In alternative embodiments the receptors, fragments, or portions thereof have a biological activity, e.g., one characteristic of a receptor for IL-10, or are from a mammal, including a mouse or human.

In particular embodiments, the nucleic acids, are capable of hybridizing at high stringency to SEQ ID NO: 1 or 3, or are isolated using a probe which hybridizes at high stringency to a human receptor for IL-10. The invention also embraces nucleic acids capable of hybridizing to these sequences which contain mutations selected from the group consisting of nucleotide substitutions, nucleotide deletions, nucleotide insertions, and inversions of nucleotide stretches. Alternative embodiments include recombinant nucleic acids which are operably linked to a genetic control element, e.g., a prokaryotic promoter element or a eukaryotic expression control element, including a viral promoter.

Various embodiments include expression vectors for expressing DNA encoding a receptor for IL-10, or vectors comprising these sequences and a selection marker. The invention also embraces host cells comprising an expression vector which is capable of expressing these receptors. Preferred host cell embodiments include prokaryotes, including gram negative and gram positive bacteria, including *E. coli;* lower eukaryotes, including yeasts; and higher eukaryotes, including animal cells, including mammalian cells, including human. Preferably the receptor is selected from a human receptor for IL-10; or a mouse receptor for IL-10. Other embodiments include nucleic acids further encoding a second protein or polypeptide, e.g., where the second polypeptide is fused to the receptor. The invention further embraces subcellular structures, cells, or organisms comprising these nucleic acids.

The present invention also embraces proteins or polypeptides encoded by these DNA sequences, preferably which are substantially free of protein or cellular contaminants, other than those derived from a recombinant host. The receptor proteins or polypeptides will often be from a mammal, including a mouse or human, and can have an amino acid sequence as found in SEQ ID NO: 2 or 4, or an allelic or species variant thereof, or a unique portion thereof. The receptor proteins or polypeptides can be attached to a solid support, be substantially pure, or be in a pharmaceutically acceptable form, with or without additional carriers or excipients. The invention also conceives of fusion proteins or polypeptides, including those further comprising a sequence from a second receptor protein. Other embodiments include subcellular structures, cells, or organisms comprising such receptor proteins or polypeptides.

The invention also provides methods for producing receptor proteins or polypeptides comprising culturing a cell comprising a described nucleic acid in a nutrient medium; and expressing the receptor proteins or polypeptides in the cell. Various alternative embodiments further comprise a step of purifying the receptor proteins or polypeptides, where the receptor proteins or polypeptides are secreted into the medium and purified therefrom, and wherein the receptor is from a mammal, including a mouse or human. The invention also provides receptors made by these methods and exhibiting a post-translational modification pattern distinct from that in normal native receptor, e.g., glycosylation; alkylation; and carboxylation. The receptor can be made in a cell line expressing a receptor exhibiting a non-natural receptor glycosylation pattern. The invention also provides methods for diagnosing a medical condition characterized by inappropriate IL-10 response in a host comprising contacting a sample from the host with a specific binding reagent to a nucleic acid encoding a receptor for IL-10 or fragment thereof; or to a receptor for IL-10 or fragment thereof, and measuring the level of binding of the reagent to the sample. In various alternatives, the binding reagent is a nucleic acid probe for a gene encoding the receptor or fragment thereof, an antibody which recognizes a receptor for IL-10 or a fragment thereof; or a ligand, agonist, or antagonist for a receptor for IL-10. Preferably the receptor is from a mammal, including a mouse or human.

The invention also provides methods of screening for a compound having binding affinity to a receptor for IL-10, comprising producing an isolated or recombinant receptor by a method as described; and assaying for the binding of the compound to the receptor, thereby identifying compounds having defined binding affinity therefor. Preferably, the compound is a ligand, agonist, or antagonist for these receptors.

The present invention also provides proteins and polypeptides, e.g., free of proteins with which they are naturally associated and having an amino acid sequence homologous to a fragment of a receptor for IL-10. Typically, the receptor is from a mammal, including a mouse or human, and specific embodiments have sequence of SEQ ID NO: 2 or 4.

The invention encompasses a recombinant or substantially pure polypeptides comprising a region exhibiting substantial identity to an amino acid sequence of a receptor for IL-10. Particular embodiments include polypeptides having a sequence selected from SEQ ID NO: 2 or 4, or polypeptides attached to a solid support.

The present invention provides various antibodies having binding affinity to a recombinant receptor for IL-10, or a fragment thereof. Preferred embodiments are raised against the receptor for IL-10, and can be either neutralizing or non-neutralizing antibodies; fused to a toxic moiety, or conjugated to a marker moiety, including a radionuclide. Preferably, the antibody binds to a receptor from a mammal, including a mouse or human.

Additionally, the invention provides methods of treating a host having a medical condition characterized by inappropriate IL-10 response or exhibiting abnormal expression of a receptor for IL-10, comprising administering to the host a therapeutically effective amount of a composition comprising (a) an antibody which binds to a receptor for IL-10 or fragment thereof; (b) a ligand, agonist, or antagonist for a receptor for IL-10; or (c) a ligand binding receptor, or fragment thereof, for IL-10. In one embodiment, the antibody is a monoclonal antibody. In others, the agonist or antagonist is selected by a method of contacting a target compound with (a) isolated or recombinant receptor for IL-10, or (b) ligand binding fragment of the receptor; and identifying the target compound with isolated or recombinant receptor for IL-10, or ligand binding fragment of the receptor; and identifying the target compound based upon the effects of the contacting.

The invention also provides methods of evaluating binding affinity of a test compound to a receptor for IL-10, the method comprising contacting (a) a sample containing the receptor, or a fragment thereof, with a labeled compound having known affinity for the receptor; and (b) the test compound; and measuring the level of bound labeled compound, the amount being inversely proportional to the amount of test compound which bound to the receptor. Preferably, the receptor is from a mammal, including a mouse or human. An alternative embodiment is a method of modulating biological activity of a receptor for IL-10, comprising contacting the receptor with a composition selected from an antibody which binds to the receptor; a ligand, agonist, or antagonist for a receptor for IL-10; and a ligand binding fragment from a receptor for IL-10.

The invention also provides useful reagents in kit form. For example, it provides a kit useful for (a) quantifying a receptor for IL-10; or (b) for determining the bindings affinity of a test sample to a receptor for IL-10; the kit comprising a labeled compound having binding affinity for the receptor, and a means for measuring bound labeled compound. Various embodiments include kits further comprising recombinant receptor, wherein the labeled compound is a ligand for the receptor, including IL-10; wherein the compound is an antibody; wherein the means for measuring is a solid phase for immobilizing the receptor; or wherein the solid phase contains a capture molecule. The invention also provides a kit for assaying, in a sample, antibody against a receptor for IL-10, comprising the receptor and an antibody detection means. In one embodiment the receptor is attached to a solid support.

The invention also provides compounds known to modulate activity of a receptor for IL-10, selected by a method of: contacting the compound with isolated or recombinant receptor, or a fragment thereof, for IL-10; and evaluating the effect on biological activity by the contacting.

The invention also provides methods of modulating a biological effect of IL-10, comprising a step of interfering with biological mechanisms, e.g., signal transduction, of a class 2 cytokine receptor, e.g., an interferon receptor. It also provides methods of modulating a biological effect of a class 2 receptor, e.g., an interferon, comprising a step of interfering with biological mechanisms of an IL-10 receptor. (Numbered references following are found at the end of Example 14) Using epitope-tagged hIL-10, we identified a cell line expressing hIL-10R and isolated cDNA clones encoding hIL-10R. hIL-10R has 70% and 60% sequence identity to mIL-10R at the nucleic acid and protein levels, respectively (23). COS7 and Ba/F3 cells transfected with hIL-10R cDNA clones express cell-surface receptors, which bind hIL-10 (but not mIL-10) specifically with high affinity, and Ba/F3 cells expressing recombinant hIL-10R are stimulated by hIL-10 but not mIL-10, (FIGS. 22A–D). Recombinant hIL-10R is indistinguishable in size from hIL-10R expressed by the cells from which the cDNA was isolated, and moreover, is similar in size to mIL-10R (FIG. 21). hIL-10R mRNA was present in all cells examined which are known to respond to hIL-10 (FIG. 23A–C). We thus conclude that the hIL-10R identified is a functional receptor for hIL-10, because it binds ligand specifically, mediates transduction of a biological response to hIL-10, and exhibits the known species specificity of the human receptor (1, 46).

We have observed significant levels of hIL-10R mRNA expression by cells about which relatively little is known concerning their direct responses to IL-10: T cells and NK/LGL cells; IL-10 inhibits cytokine synthesis by both T cells and NK cells, but these inhibitory effects are indirect, mediated via the monocyte/macrophage costimulatory cell (1). However, hIL-10 does enhance generation of lymphokine-activated killer activity from resting NK cells in response to IL-2 (7), and also has demonstrable inhibitory effects on subsets of human T cell clones (48). In addition, mIL-10 costimulates growth of mouse thymocytes and T cells (14), and enhances generation of cytotoxic T cell activity (15). NK/LGL cells express a significant level of hIL-10R mRNA, especially when compared to the β-actin reference standard (FIG. 23B). T cells and T cell clones also express readily detectable hIL-10R mRNA, which is apparently down-regulated in the latter in response to activation by anti-CD3 and TPA (FIGS. 23A, C). We do not at present know the significance of the observed downregulation of hIL-10R mRNA expression, especially since it is unclear whether even an 8–10-fold lower hIL-10R number would significantly impair the ability of activated T cells to respond to IL-10. In any case, the expression of significant-levels of hIL-10R mRNA by these cells and its regulation by activation stimuli suggest possible additional, as yet uncharacterized effects of IL-10 on T cells and NK cells.

That the Kd of hIL-10R is larger than that obtained for $^{125}$I-hIL-10 binding to mIL-10R (~70 pM) expressed on transfected Ba/F3 (BaMR29) cells (23) is consistent with the observation that hIL-10 has a reproducibly higher specific activity in stimulation of BaMR29 cells compared to Ba8.1 cells (AH & KWM, unpublished). This finding may suggest an intrinsically higher affinity of mIL-10R for ligand. Alternatively, it is possible that additional receptor or signalling components provided in trans by (murine) Ba/F3 cells interact much more efficiently with mIL-10R than with hIL-10R due to the species difference.

Like the cellular cytokine, vIL-10 inhibits macrophage activation and sitimulates human and mouse B cells (1). Thus, further evidence for the possible existence of additional IL-10R components on human B cells and activated monocytes was the finding that vIL-10 at 100-fold molar excess did not detectably compete with FLAG-hIL-10 for binding to hIL-10R-although at 500-fold molar excess, vIL-10 competed slightly with FLAG-hIL-10 (data not shown). Moreover, we have so far been unable to detect significant levels of binding of FLAG-vIL-10 to either Ba8.1 or COS7 cells expressing hIL-10R using FACS analysis.

hIL-10R, along with mIL-10R (23), are new members of the class II subgroup of CR, the IFNR family. Many of the activating effects of IFNγ on macrophages are inhibited by IL-10 (1). The structures of the ligand-binding chains of IFNαβR and IFNγR are known (43, 50, 51), but biological and genetic evidence has been accumulated for the existence of an additional IFNR polypeptide(s) involved in transduction of a biological signal (see for example (52)). In this light, and in view of the demonstration of shared subunits among receptors for different cytokines (53, 54), it is possible that IL-10R could likewise share a second receptor chain with an IFNR. If so, IL-10 and IFNγ might compete for binding to each other's receptors, but as noted above, neither IFNα nor IFNγ competed for hIL-10 binding to recombinant hIL-10R. However, in the IL3, IL5, and GMCSF receptor system (45) a group of cytokine receptors shares a common secondary chain, but each CR is only capable of binding its respective cytokine. A further possibility is that the IL-10-IL-10R interaction might directly antagonize the IFNR signal transduction pathway (55, 56), perhaps by interacting with or sequestering one or more of its components. Further characterization of the structure and signal transduction mechanisms of IL-10R and IFNR may illuminate these possibilities.

Acknowledgments

The authors thank Dr. T. Kitamura for his continuing interest in this work and for valuable advice; Drs. J. Gabert and T. Kitamura for samples of TF-1 mRNA; S. Zurawski for teaching us receptor binding assay techniques; Dr. M. Billah for information and advice regarding DMSO induction of U937 cells; Drs. C.-C. Chou and J. Tan for sharing information before publication;

Dr. D.-H. Hsu for contributions to the early phase of this project; J. Polakoff, J. Cupp, and E. Callas for assistance in cell sorting and analysis; and D. Robison for synthetic oligonucleotides. A. S.-Y. Ho was supported by a DNAX Research Institute postdoctoral fellowship. DNAX Research Institute is supported by Schering-Plough Corporation.

1. The sequence reported herein has been deposited in the Genbank database, Accession No. 00672.

Abbreviations

CR, cytokine receptor; CSIF, cytokine synthesis inhibitory factor; ELISA, enzyme-linked immunosorbent assay; FACS, fluorescence-activated cell sorter; IFN, interferon; IL, interleukin; LGL, large granular lymphocyte; ORF, open reading frame; PBMC, peripheral blood mononuclear cells; PCR, polymerase chain reaction; SA-PE, streptavidin-phycoerythrin conjugate

BRIEF DESCRIPTION OF THE FIGURES

FIG. 1 shows the structure of the FLAG-mouse IL-10 (FLAG-mIL-10) and FLAG-human IL-10 (FLAG-hIL-10) hybrid cytokines. A leader sequence from the human CD8 gene was used to ensure processing and secretion of FLAG-IL-10. A human CD38 leader sequence is used, from MAL . . . ARP. This is fused to a FLAG sequence from DYK . . . to . . . DDK. These sequences are fused to mouse IL-10 at QYS . . . , or to human IL-10 at SPG.

FIGS. 2A and 2C show FACS profiles from freshly cultured cells. FIGS. 2B and 2D show FACS profiles after three cycles of enrichment for the top 3%–5% of IL-10 receptor positive cells. In each panel, the right profile shows a profile of FLAG-mIL-10 bound to IL-10 receptor, while the left profile show the result of competition with a 30–100-fold excess of wild-type mIL-10, which reduces signal to background. For panels in FIGS. 2A–2D, 3, 4, and 5A–5B, the horizontal axis is fluorescence intensity in arbitrary units, and the vertical axis is cell number, in arbitrary units.

FIG. 5A shows binding of FLAG-hIL-10 (dark), or with a 30–100-fold excess of hIL-10 (light), which competes the signal to background levels. FIG. 5B shows binding of FLAG-hIL-10 is not competed by a 30–100-fold excess of mIL-10.

In FIG. 7A, approximately 0.4 ml of lactoperoxidase-iodinated hIL-10 was passed through a 120 ml G75 Sepharose (Pharmacia LKB) column and collected in 1.1 ml fractions. Radioactivity was determined from fraction aliquots with a Clinigamma Counter (Pharmacia LKB). Blue Dextran (BD) and Bromophenol Blue (BPB) were used as markers for the void and total volumes, respectively. In FIG. 7B, low molecular weight markers (Pharmacia LKB) were applied to the G75 column, 1.1 ml fractions were collected, and protein concentrations of these fractions were determined using the BCA Protein Detection System (Pierce, Rockford, Ill.). The fractions of peak protein concentration were then plotted against the logarithms of the molecular weights. For FIG. 7C, approximately 20,000 cpm from the three peak fractions were partitioned in a 15% SDS-PAGE under non-reducing conditions. At the completion of the electrophoresis the gel was vacuum dried on Whatman paper followed by autoradiography using XAR film (Kodak). Molecular weight markers (BRL) were visualized by Coomassie blue staining.

In FIG. 11A, the two bars of each set indicate binding in the absence (left) or presence (right) of 1000-fold molar excess unlabeled hIL-10, respectively, in binding buffer with 500 pM labeled hIL-10. Triplicate binding assays were performed. Two binding experiments using the same preparation of labeled hIL-10 are presented in FIG. 11B.

In FIG. 12A, increasing concentrations of labeled hIL-10 were added to $5\times10^6$ MC/9 cells and tested for specific binding. FIG. 12B shows Scatchard analysis of the data obtained above using the EBDA program (Elsevier Biosoft, Cambridge, U.K.). The slope of the line obtained gives a Kd value of 49 pM while the Bmax is 4.0 pM.

In FIG. 13A, increasing concentrations of labeled hIL-10 were added to 5×10⁶ JY cells and tested for specific binding. FIG. 13B shows Scatchard analysis of data obtained from above using the EBDA program. The slope of the line gives an estimated Kd value of 140 pM while the Bmax value is 7.5 pM.

In FIG. 14A, a 500-fold molar excess of unlabeled human IL-10 or 1500-fold excess mouse IL-10 was incubated in duplicate with 100 pM iodinated hIL-10 in a binding assay with the mouse mast cell line MC/9. FIG. 14B shows the same as FIG. 14A except that the human B lymphoma line JY was used.

FIG. 15A shows the human IL-10 receptor and FIG. 15B shows the mouse IL-10 receptor.

FIG. 16A shows the increasing specific binding obtained when increasing amounts of labeled human IL-10 are added to COS7 cells transfected with the human (SW8.1) IL-10 cDNA clone. FIG. 16B shows a Scatchard plot obtained from these data points, which provide a Kd value of 120 pM. This result indicates that the recombinant human receptor, when expressed in COS7 cells, is able to bind human IL-10 with an affinity comparable to that of the natural human IL-10 receptor, as shown previously.

FIG. 17A shows the increasing specific binding obtained when increasing amounts of labeled human IL-10 are added to COS7 cells transfected with the mouse (m3.14) IL-10 cDNA clone. FIG. 17B shows a Scatchard plot obtained from these data points, which provide a Kd value of 83 pM. This result indicates that the recombinant mouse receptor, when expressed in COS7 cells, is able to bind human IL-10 with an affinity comparable to that of the natural human IL-10 receptor.

FIG. 22A FACS analysis of hIL-10R expression by Ba8.1 cells as detected by binding of FLAG-hIL-10 (histogram 1, shaded), FLAG-mIL-10 (histogram 2), or FLAG-hIL-10 in the presence of 100-fold excess hIL-10 (histogram 3. FIG. 22B FACS analysis of hIL-10R expression by BaF-Neo cells as detected by the FLAG-hIL-10. FIG. 22C Scatchard analysis of $^{125}$I-hIL-10 binding to Ba8.1 cells. Data were plotted and analyzed by a linear least-squares fit, and in the particular experiment shown gave a Kd value of _250 pM, _6000 receptors/cell, and a coefficient of variation r=0.997. Data from repeat experiments suggested Kd=200–250 pM, with 6000–8000 hIL-10R/cell. FIG. 22D Response of Ba8.1 and BaF-NeO cells to mIL10 and hIL-10. The responses of Ba8.1 cells in the presence of 10 μg/ml anti-hIL-10 (12G8) or isotype control (GL117) Mab are also shown. hIL-10 units were based on a CSIF assay using human PBMC (7, 10, 18).

FIG. 23A Human multiple tissue RNA blot (Clontech, Palo Alto, Calif.): each lane contains 2 μg polyA+RNA. FIG. 23B 10 μg total RNA from cells shown was used in each lane, except for TF-1 cells (2 μg polyA+RNA). U937/DMSO RNA was from U937 cells which were cultured with 1.5% DMSO for three days before RNA extraction (25, 26). The apparent different size of hIL-10R mRNA in LGL is a gel artifact; longer exposures showed that the mobility of β-actin mRNA was similarly affected (not shown). FIG. 23C 10 μg total RNA from T cell clones shown was used in each lane. T cell clones were either resting (−) or induced (+) with anti-CD3 and TPA as described (18, 48) prior to RNA isolation.

DETAILED DESCRIPTION OF THE PREFERRED EMBODIMENTS

Figure 2A:
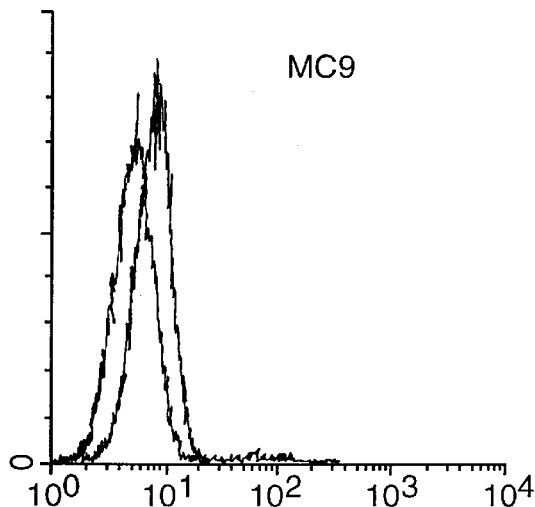
FIGS. 2A–2D, show detection by Fluorescence Activated Cell Sorter (FACS) analysis and enhancement of IL-10 receptor expression. MC/9 is a mouse mast cell line. J774 is a mouse macrophage cell line.
Figure 2B:
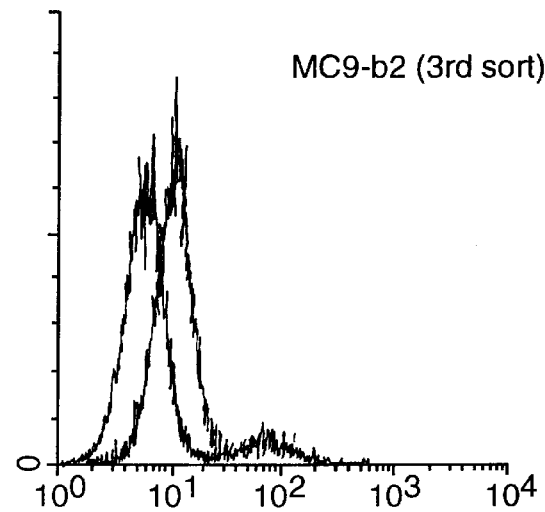
Figure 2C:
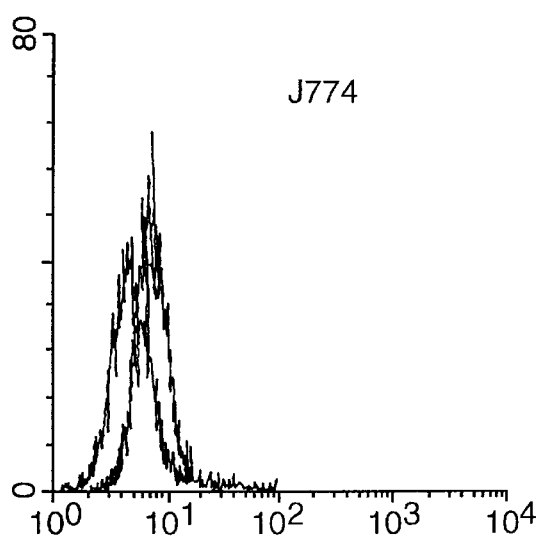
Figure 2D:
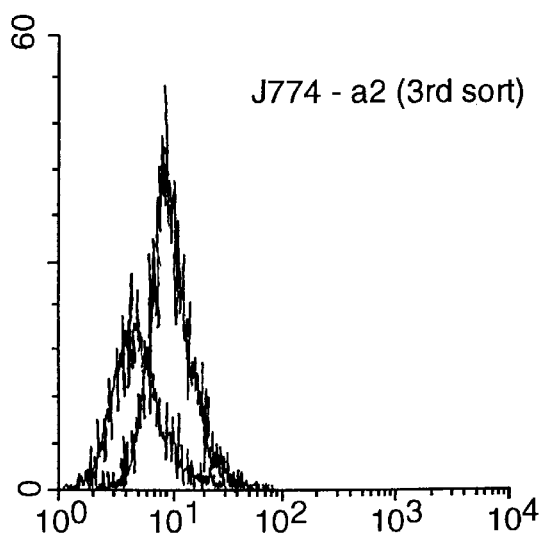

OUTLINE
I. General
II. Nucleic Acids
III. Receptor Variants
IV. Making Receptor
V. Receptor Isolation
VI. Receptor Analogs
VII. Antibodies
VIII. Other Uses of Receptors
IX. Ligands: Agonists and Antagonists
X. Kits
XI. Therapeutic Applications
XII. Additional Receptor Subunits I. General The present invention provides amino acid sequence and DNA sequence for components of receptors for interleukin-10, e.g., both a human receptor subunit and a mouse receptor subunit. These sequences were obtained based upon the ability of the protein which they encode to bind IL-10. Pools of cells containing cDNA expression library products were screened for their ability to bind IL-10. The receptor-ligand complexes were chemically crosslinked and methods were applied to isolate nucleic acids encoding those binding proteins.

This invention provides recombinant nucleic acids, and isolated or substantially pure nucleic acids, which are substantially homologous to a sequence encoding a receptor, or a fragment thereof, for an IL-10 peptide. Nucleic acids encoding fusion polypeptides are contemplated, as are vectors, cells, and organisms comprising such nucleic acids. Recombinant polypeptides, and isolated or substantially pure polypeptides derived from these protein sequences are encompassed herein. Fusion polypeptides are provided, along with cells and organisms comprising the polypeptides. Compositions comprising these polypeptides are embraced herein. Exemplary embodiments are, again, full length human and mouse proteins, and fragments thereof, e.g., soluble ligand binding fragments consisting of the extracellular domain of the protein.

The invention provides antibodies specific for epitopes unique to, or characteristic of, these receptor components. These include antibodies which bind specifically to either epitopes which are shared by the different species counterparts of receptors for IL-10, or epitopes which distinguish between different species counterparts.

Kits comprising any of these compositions are included herein. Thus, various nucleic acid molecules, polypeptides, and antibodies will provide the bases of various diagnostic or therapeutic kits.

The various compositions also provide bases for methods for treating hosts, particularly those suffering from undesired receptor function, e.g., autoimmune diseases, inappropriate immune responses of the T helper 2 class, inappropriate function of class II MHC, suppressed monocyte or macrophage-related immune functions, septic or toxic shock responses, and intracellular pathogen-mediated diseases, by administering effective amounts of these reagents, directly or indirectly, or contacting biological samples with them.

The compositions, e.g., ligand-binding fragments of the receptor, also provide the means to select and screen for additional agonists and antagonists for the respective receptor subtypes. Selected compounds are made available, both ligands and molecules which interact at polypeptide regions separate from the ligand binding regions. Of particular utility are compounds affecting multiple receptor types, e.g., those exhibiting desired spectra of specificity for modulating various biological activities.

The group of receptor components is also very useful in providing a group of receptor polypeptides having both substantial similarities and critical differences. These different species counterparts, as a group, may allow dissecting of structure and function for the class in a manner impossible from characterization of a single species version.

The descriptions below are often directed to either a mouse IL-10 receptor or a human receptor, but most properties, both structural or biological, will be shared between them and other mammalian counterparts, e.g., rat, pig, sheep, goat, etc. In particular, analogous uses and reagents derived from other species counterparts will be developed. Identification of new bioactive ligands for new receptor variants will also result.

Expression cloning of an IL-10 binding protein yielded nucleic acids encoding IL-10 receptor components from both human and mouse. Some standard methods are described or referenced, e.g., in Maniatis, et al. (1982) *Molecular Cloning. A Laboratory Manual,* Cold Spring Harbor Laboratory, Cold Spring Harbor Press; Wu, et al. (eds.)(1989) "Recombinant DNA Methodology" from *Methods in Enzymology,* Academic Press, NY; Sambrook, et al. (1989) *Molecular Cloning: A Laboratory Manual,* (2d ed.), vols 1–3, CSH Press, NY; Ausubel, et al., *Biology,* Greene Publishing Associates, Brooklyn, N.Y.; or Ausubel, et al. (1987 and Supplements) *Current Protocols in Molecular Biology,* Greene/Wiley, New York; all of which are each incorporated herein by reference. These genes allow isolation of species variants of these genes encoding a component of a receptor for IL-10, beyond the herein described human and mouse embodiments. One procedure is broadly set forth below in Table 1.

TABLE 1: Detection of IL-10 Receptor
1. Cells+FLAG-IL-10±excess IL-10
2. Wash
3. Cross-linking
4. Wash
5. Biotinylated anti-FLAG antibody (M1 or M2)
6. Wash
7. Streptavidin-phycoerythrin conjugate (SA-PE)
8. Wash
9. Fluorescence activated cell sorting (FACS)

A cDNA library, constructed in an appropriate expression vector was prepared from RNA isolated from appropriate cells. These cells were responsive to IL-10. A B cell line BJAB was used to make the cDNA library from human, and a mast cell line MC/9 and a macrophage cell line J774 were used to make cDNA from mouse. Several modifications and unique techniques had to be utilized to overcome problems associated with isolating a cDNA clone by expression cloning. In particular, it was necessary to identify an appropriate cell line from which to prepare the cDNA library encoding the desired IL-10 binding activity. Next, it was very useful to establish that IL-10 could bind to clonally isolated expression products. A cell line for expression with low background binding was also useful.

The IL-10 used as a ligand was modified by addition of an N-terminal extension. This extension was useful in providing a means to detect a ligand-receptor crosslinked complex. In this case, the extension was the FLAG peptide, though others could have been equivalent. See Hopp, et al. (1988) *Bio/Technolocry* 6:1204–1210. At the outset, it was unclear that the extension would not interfere in ligand-receptor interaction. It was also unclear whether the IL-10 binding protein interaction was physiologically important.

The extension provided a means to attach a marker or signal for a crosslinked ligand-receptor complex. Thus, means were provided to detect cells expressing a receptor component, or to affinity immobilize cells possessing a crosslinked complex on their surface. Both of these methods were applied to enrich and verify the identity of the receptor component.

Once a cDNA for a receptor component was isolated from mouse, it was partially sequenced. The same was done for the human receptor. Both are now completely sequenced. The nucleotide sequence reveals partial amino acid sequence of the primary translation product of an IL-10 receptor component, i.e., the amino acid sequence before any post-translational modification. The present invention encompasses both allelic variants of the protein and various metabolic variants, e.g., post-translational modifications, produced by different cell types, including recombinant proteins. Various glycosylation variants and post-translational modification variants are available by choosing appropriate cells for expression of recombinant nucleic acids.

Complete human IL-10 receptor nucleotide and amino acid sequences are shown in SEQ ID NO: 1 and 2, respectively. SEQ ID NO: 3 and 4 disclose nucleotide and amino acid sequences of the mouse receptor component, that binds IL-10. SEQ ID NO: 3 corresponds to a mouse nucleic acid sequence; SEQ ID NO: 4 corresponds to a mouse amino acid sequence.

The human sequence was derived from the clone SW8.1, which was deposited with the ATCC on Dec. 4, 1992, and assigned accession number 69146. The nucleotide sequence has been verified in both directions, and the presumptive open reading frame would begin in the appropriate position corresponding to those indicated for the mouse sequence. A hydrophobic membrane spanning segment appears to correspond to amino acids 217–243 of the mature human receptor component. Thus, a soluble binding fragment would correspond to one extending from about residues 1–216, or shorter.

As used herein, the term "IL-10 receptor" shall include a protein or peptide comprising amino acid sequences described in herein or encoded by nucleic acid sequences shown therein, or a fragment of either entity. It also refers to a polypeptide which functionally and similarly binds to an IL-10 protein, e.g., human or mouse, with high affinity, e.g., at least about 10 nM, usually better than about 3 nM, preferably better than about 1 nM, and more preferably at better than about 0.5 nM. It is expected that the binding affinity of a multiprotein complex to the ligand will be higher when additional protein components associate with the component disclosed herein, e.g., an α-like chain. The term shall also be used herein to refer, when appropriate, to a receptor gene, alleles of the human or mouse receptor component, or other species counterparts, e.g., mammals other than humans or mice. The term does not encompass natural antibodies which bind the ligand, since the structural features, e.g., complementarity determining regions (CDRs) of an antibody binding site, are different from a receptor's ligand binding site. Nucleic acid sequence from a mouse counterpart receptor component is provided in SEQ ID NO: 3 and a predicted corresponding amino acid sequence is designated SEQ ID NO: 4. This mouse sequence was derived from the clone pMR29, which was deposited with the ATCC on Dec. 4, 1992, and has been assigned accession number 69147. Table 2 compares the human and mouse receptors at both the nucleotide and amino acid levels.

Additionally, Applicants incorporate herein by reference, in its entirety including all figures and drawings, to the present application, the commonly assigned divisional application U.S. Ser. No. 08/477,166, filed on Jun. 7, 1995, for all purposes.

TABLE 2

Comparison of the human and mouse IL-10 receptor subunits at the nucleotide and amino acid levels. See SEQ ID NOs 1 through 4.

nucleotide; mouse above, human below

```
  1 CCATTGTGCTGGAAAGCAGGACGCGCCGGCCGGAGGCGTAAAGGCCG...   47
                  ||  ||||||||   ||||||
  1 .....................AAAGAGCTGGAGGCGCGCAGGCCGGCT    27

48 ..GCTCCAGTGGACGATGCCGCTGTGCGCCCAGGATGTTGTCGCGTTTGC   95
     |||||  |    || |  || | ||||||||||| || || |
 28 CCGCTCCGGCCCCGGACGATGCGGCGCGCCCAGGATGCTGCCGTGCCTCG   77

96 TCCCATTCCTCGTCACGATCTCCAGCCTGAGCCTAGAATTCATTGCATAC  145
     |    | |||   || ||  ||||||  | || |       || |
 78 TAGTGCTGCTGGCGGCGCTCCTCAGCCTCCGTCTTGGCTCAGACGCTCAT  127

146 GGGACAGAACTGCCAAGCCCTTCCTATGTGTGGTTTGAAGCCAGATTTTT  195
    ||||||||  |||||  ||||||  |  |  |||||||||||||||  ||||||
128 GGGACAGAGCTGCCCAGCCCTCCGTCTGTGTGGTTTGAAGCAGAATTTTT  177

196 CCAGCACATCCTCCACTGGAAACCTATCCCAAACCAGTCTGAGAGCACCT  245
    |||  |||||||||||||||||  |||  ||||||||||  |||||||||||||||  ||  ||||
178 CCACCACATCCTCCACTGGACACCCATCCCAAATCAGTCTGAAAGTACCT  227

246 ACTATGAAGTGGCCCTCAAACAGTACGGAAACTCAACCTGGAATGACATC  295
    ||||||||||||||  |||   |||  ||||       |||||||   ||||
228 GCTATGAAGTGGCGCTCCTGAGGTATGGAATAGAGTCCTGGAACTCCATC  277

296 CATATCTGTAGAAAGGCTCAGGCATTGTCCTGTGATCTCACAACGTTCAC  345
    |  ||||||        ||| |   ||||||  ||| ||  ||   |  |||
278 TCCAACTGTAG......CCAGACCCTGTCCTATGACCTTACCGCAGTGAC  321

346 CCTGGATCTGTATCACCGAAGCTATGGCTACCGGGCCAGAGTCCGGGCAG  395
    |  ||||  |||||  |||    |||  ||||||||||||||||||||||  |||||  |
322 CTTGGACCTGTACCAC...AGCAATGGCTACCGGGCCAGAGTGCGGGCTG  368

396 TGGACAACAGTCAGTACTCCAACTGGACCACCACTGAGACTCGCTTCACA  445
    |||||   |||  |  |  ||||||||||||||||   |||  |  || |||||||  |
369 TGGACGGCAGCCGGCACTCCAACTGGACCGTCACCAACACCCGCTTCTCT  418
```

TABLE 2-continued

Comparison of the human and mouse IL-10 receptor
subunits at the nucleotide and amino acid levels. See SEQ ID
NOs 1 through 4.

```
 446 GTGGATGAAGTGATTCTGACAGTGGATAGCGTGACTCTGAAAGCAATGGA  495
     ||||||||||||| |||||||||| | || |||| || |         |
 419 GTGGATGAAGTGACTCTGACAGTTGGCAGTGTGAACCTAGAGATCCACAA  468

496 CGGCATCATCTATGGGACAATCCATCCCCCAGGCCCACGATAACCCCTG   545
     ||| ||||    ||||  || || |  |||||||||||| |||   ||| |
 469 TGGCTTCATCCTCGGGAAGATTCAGCTACCCAGGCCCAAGATGGCCCCCG  518

546 CAGGGGATGAGTACGAACAAGTCTTCAAGGATCTCCGAGTTTACAAGATT  595
     |  ||   ||||| |||||| |||||  |  ||||||  || |||||
 519 CGAATGACACATATGAAAGCATCTTCAGTCACTTCCGAGAGTATGAGATT  568

596 TCCATCCGGAAGTTCTC...AGAACTAAAGAATGCAACCAAGAGAGTGAA  642
     |||| || ||| |    |   | |   |||   || ||||| ||| ||
 569 GCCATTCGCAAGGTGCCGGGAAACTTCACGTTCACACACAAGAAAGTAAA  618

643 ACAGGAAACCTTCACCCTCACGGTCCCCATAGGGGTGAGAAAGTTTTGTG  692
     |||  |||| |||||| ||||  ||  || ||| || ||||  ||||
 619 ACATGAAAACTTCAGCCTCCTAACCTCTGGAGAAGTGGGAGAGTTCTGTG  668

693 TCAAGGTGCTGCCCCGCTTGGAATCCCGAATTAACAAGGCAGAGTGGTCG  742
     || | ||||| ||    |   |  || |||||||| ||||||||  |||||
 669 TCCAGGTGAAACCATCTGTCGCTTCCCGAAGTAACAAGGGGATGTGGTCT  718

743 GAGGAGCAGTGTTTACTTATCACGACGGAGCAGTATTTCACTGTGACCAA  792
      |||| ||||  |      |||| |   |||||||||||| ||||||||
 719 AAAGAGGAGTGCATCTCCCTCACCA...GGCAGTATTTCACCGTGACCAA  765

793 CCTGAGCATCTTAGTCATATCTATGCTGCTATTCTGTGGAATCCTGG...  839
     | |   |||||  |      ||  ||| |||  ||| | |||   |||
 766 CGTCATCATCTTCTTTGCCTTTGTCCTGCTGCTCTCCGGAGCCCTCGCCT  815

840 TCTGTCTGGTTCTCCAGTGGTACATCCGGCACCCGGGGAAGTTGCCTACA  889
      ||| ||||  ||||||  |||   | |||| ||      |||| || |
 816 ACTGCCTGGCCCTCCAGCTGTATGTGCGGCGCCGAAAGAAGCTACCCAGT  865

890 GTCCTGGTCTTCAAGAAGCC...TCACGACTTCTTCCCAGCCAACCCTCT  936
     |||||| |||||||||||||    |  |  ||||||    |   |  |
 866 GTCCTGCTCTTCAAGAAGCCCAGCCCCTTCATCTTCATCAGCCAGCGTCC  915

937 CTGCCCAGAAACTCCCGATGCCATTCACATCGTGGACCTGGAGGTTTTCC  986
     || |||||| || || || || ||| |||  | ||||| |||||  ||
 916 CTCCCCAGAGACCCAAGACACCATCCACCCGCTTGATGAGGAGCCTTTT   965

987 CAAAGGTGTCACTAGAGCTGAGAGACTCAGTCCTGCATGGCAGCACCGAC  1036
      ||||||||| ||||||||||  ||||  |  |||| ||||||||||| |||
 966 TGAAGGTGTCCCCAGAGCTGAAGAACTTGGACCTGCACGGCAGCACAGAC 1015

1037 AGTGGCTTTGGCAGTGGTAAACCATCACTTCAGACTGAAGAGTCCCAATT  1086
     |||||||||||||||   |   ||||  |||||||||||||| |||||||
1016 AGTGGCTTTGGCAGCACCAAGCCATCCCTGCAGACTGAAGAGCCCCAGTT  1065

1087 CCTCCTCCCTGGCTCCCACCCCCAGATACAGGGGACTCTGGGAAAAGAAG  1136
     ||||||||||| | |||||||||      | || ||||||||| |  |
1066 CCTCCTCCCTGACCCTCACCCCCAGGCTGACAGAACGCTGGGAAACGGGG  1115

1137 AGTCTCCAGGGCTACAGGCACCT............GTGGGGACAACACG  1174
     ||  ||  |||   ||||  || ||                |  | |  |||
1116 AGCCCCCTGTGCTGGGGGACAGCTGCAGTAGTGGCAGCAGCAATAGCACA  1165
```

TABLE 2-continued

Comparison of the human and mouse IL-10 receptor
subunits at the nucleotide and amino acid levels. See SEQ ID
NOs 1 through 4.

```
1175 GACAGTGGGATCTGCCTGCAGGAGCCCGGCTTACACTCCAGCATGGGGCC 1224
     |||||  ||||||||||||||||||| || |   |  ||||||  ||||| 
1166 GACAGCGGGATCTGCCTGCAGGAGCCCAGCCTGAGCCCCAGCACAGGGCC 1215

1225 CGCCTGGAAGCAGCAGCTTGGATATACCCATCAGGACCAGGATGACAGTG 1274
     |  ||||| ||||  |||  || ||    || ||  || ||||||||||| 
1216 CACCTGGGAGCAACAGGTGGGAGCAACAGCAGGGGCCAGGATGACAGTG 1265

1275 ACGTTAACCTAGTCCAGAACTCTCCAGGGCAGCCTAAGTACACACAGGAT 1324
     | || || |||| || |||||  || ||| | |  | | |||||||||| | 
1266 GCATTGACTTAGTTCAAAACTCTGAGGGCCGGGCTGGGGACACACAGGGT 1315

1325 GCATCTGCCTTGGGCCATGTCTGTCTCCTAGAACCTAAAGCCCCTGAGGA 1374
     |  || |||||||||||  |  |||  || ||| ||  |  |||| ||| 
1316 GGCTCGGCCTTGGGCCACCACAGTCCCCCGGAGCCTGAGGTGCCTGGGGA 1365

1375 GAAAGACCAAGTCATGGTGACATTCCAGGGCTACCAGAAACAGACCAGAT 1424
     ||||||  ||       |||  |||||||||||| |||| || |||||||||| 
1366 AGAAGACCCAGCTGCTGTGGCATTCCAGGGTTACCTGAGGCAGACCAGAT 1415

1425 GGAAGGCAGAGGCAGCAGGCCCAGCAGAATGCTTGGACGAAGAGATTCCC 1474
     |    |  ||||  |||  |     ||| ||| |||| |||   ||| 
1416 GTGCTGAAGAGAAGGCAACCAAGACAGGCTGCCTGGAGGAAGAATCGCCC 1465

1475 TTGACAGATGCCTTTGATCCTGAACTTGGGGTACACCTGCAGGATGATTT 1524
     |||||||||| | ||| || || |||  |  ||||  |||||||  ||||| 
1466 TTGACAGATGGCCTTGGCCCCAAATTCGGGAGATGCCTGGTTGATGAGGC 1515

1525 GGCTTGGCCTCCACCAGCTCTGGCCGCAGGTTATTTGAAACAGGAGTCTC 1574
     |  || |||||||||| |||||||  || ||||||||||||||  || |||  ||| 
1516 AGGCTTGCATCCACCAGCCCTGGCCAAGGGCTATTTGAAACAGGATCCTC 1565

1575 AAGGGATGGCTTCTGCTCCACCAGGGACACCAAGTAGACAGTGGAATCAA 1624
     |   ||| ||   ||| |    |||||  | ||||    ||||||||||| || 
1566 TAGAAATGACTCTGGCTTCCTCAGGGGCCCCAACGGGACAGTGGAACCAG 1615

1625 CTGACCGAAGAGTGGTCACTCCTGGGTGTGGTTAGCTGTGAAGATCTAAG 1674
     |  || || || |||||||||||||||  || |||||   || || | 
1616 CCCACTGAGGAATGGTCACTCCTGGCCTTGAGCAGCTGCAGTGACCTGGG 1665

1675 CATAGAAAGTTGGAGGTTTGCCCATAAACTTGACCCTCTGGACTGTGGGG 1724
     |||      |||||||  |||||||| ||||  |||| || | |||| ||| 
1666 AATATCTGACTGGAGCTTTGCCCATGACCTTGCCCCTCTAGGCTGTGTGG 1715

1725 CAGCCCCTGGTGGCCTCCTGGATAGCCTTGGCTCTAACCTGGTCACCCTG 1774
     |||||||  ||||| ||||||||  ||| ||  ||  ||||||||||||| 
1716 CAGCCCCAGGTGGTCTCCTGGGCAGCTTTAACTCAGACCTGGTCACCCTG 1765

1775 CCGTTGATCTCCAGCCTGCAGGTAGAAGAATGACAGCGGCTAAGAG..TT 1822
     || | ||||| ||||||||||| |   ||  |||   ||| |||| | 
1766 CCCCTCATCTCTAGCCTGCAGTCAAGTGAGTGACTCGGGCTGAGAGGCTG 1815

1823 ATTTGTATTCCAGCCATGCCTGCTCCCCTCCCTGTACCTGGGAGGCTCAG 1872
     |||   |||   ||||||||||||||||||||  || |||| ||| || | 
1816 CTTTTGATTTTAGCCATGCCTGCTCCTCTGCCTGGACCAGGAGGAGGGCC 1865

1873 GAGTCAAAGAAAT.............ATGTGGGTCCTTTTCTGCAGACCT 1909
     |     |||| |             |||| |||||||||||| | 
1866 CTGGGGCAGAAGTTAGGCACGAGGCAGTCTGGGCACTTTTCTGCAAGTCC 1915
```

TABLE 2-continued

Comparison of the human and mouse IL-10 receptor
subunits at the nucleotide and amino acid levels. See SEQ ID
NOs 1 through 4.

```
1910 ACTG.................TGACCAGCTAGCCAGGCTCCACGGGGCA 1941
     ||||                  ||   ||| | ||||  |  ||||||
1916 ACTGGGGCTGGCCCAGCCAGGCTGCAGGGCTGGTCAGGGTGTCTGGGGCA 1965

1942 AGGAAAGGCCATCTTGATACACGAGTGTCAGGTACATGAGAGGTTGTG.G 1990
     |  ||||||| ||   |  ||||  ||||  || || ||    ||
1966 GGAGGAGGCCAACTCACTGAACTAGTGCAGGGTATGTGGGTGGCACTGAC 2015

1991 CTAGTCTGCTGAGTGAGGGTCTGTAGATACCAGCAGAGCTGAGCAGGATT 2040
     || |||| ||| || ||   ||| |||  |  ||||||||||||| ||
2016 CTGTTCTGTTGACTGGGGCCCTGCAGACTCTGGCAGAGCTGAGAAG.... 2061

2041 GACAGAGACCTCCTCATGCCTCAGGGCTGGCTCCTACA.CTGGAAGGACC 2089
     | |||  ||||| |||   ||| |  ||  =1|||  |   |  |||||
2062 GGCAGGGACCTTCTCCCTCCTAGGAACTCTTTCCTGTATCATAAAGGATT 2111

2090 TGTGTTTGGGTGTAACCTCAGGGCTTTCTGGA..TGTGGTAAGACTGTAG 2137
        |  |  | ||||  ||||||||||||  ||||||  || |
2112 ATTTGCTCAGGGGAACCATGGGGCTTTCTGGAGTTGTGGTGAGGCCACCA 2161

2138 GTCTGAAGTCAGCTGAG.CCTGGATGTCTGCGGAGGTGTTGGAGTGGCTA 2186
     | |||||||||||||| || || || || |   |   10  |      ||
2162 GGCTGAAGTCAGCTCAGACCCAGACCTCCCTGCTTAGGCCACTCGAGCAT 2211

2187 GCCTGCTACAGGATAAAGGGAAGGCTCAAGAGATAGAAG..GGCAGAGCA 2234
           ||| |   |||  | ||||  || || ||||    | |
2212 CAGAGCTTCCAGCAGGAGGAAGGGCTGTAGGAATGGAAGCTTCAGGGCCT 2261

2235 TGAGCCAGGTTTAATTTT.........................GTCCTGTA 2260
      ||  | ||  | |||||                         ||| |
2262 TGCTGCTGGGGTCATTTTTAGGGGAAAAAGGAGGATATGATGGTCACATG 2311

2261 GAGATGGTCCC.........CAGCCAGGATGGGTTACTTGTGGCTGGGAG 2301
     | ||   ||||         |  | ||  ||   ||||| ||||  ||
2312 GGGAACCTCCCCTCATCGGGCCTCTGGGGCAGGAAGCTTGTCACTGGAAG 2361

2302 ATCTTGGGGTATA......CACCACCCTGAATGATCAGCCAGTCAATTCA 2345
     |||||  |||||      |   || || |    |  | ||   ||||||
2362 ATCTTAAGGTATATATTTTCTGGACACTCAAACACATCATAATGGATTCA 2411

2346 GAGCTGTGTGGCAAAAGGGACTGAGACCCAGAATTTCTGTTCCTCTTGTG 2395
     |  |   |||| ||  | ||||||| ||   ||   |||  |  |
2412 CTGAGGGGAGACAAAGGGAGCCGAGACCCTGGATGGGGCTTCCAGCTCAG 2461

2396 A................GGTGTCTCTGCTACCCATCTGCAGACAGACATC 2429
     |                |||  |||||  ||||||||||||| |      |
2462 AACCCATCCCTCTGGTGGGTACCTCTGGCACCCATCTGCAAATATCTCCC 2511

2430 TTCATCTTTTTACTATGGCTGTGT.CCCCTGAATTACCAGCAGTGGCCAA 2478
     |  ||    ||   |  |  | ||||||  || || ||||||
2512 TCTCTCCAACAAATGGAGTAGCATCCCCCTGGGGCACTTGCTGAGGCCAA 2561

2479 GCCATT..........ACTCCCTGCTGCTCACTGTTGTGACGTCAGACCA 2518
     ||||  |          |  ||||  || | |||           |||
2562 GCCACTCACATCCTCACTTTGCTGCCCACCATCTTGCTGACAACTTCCA 2611

2519 GACCAGAC...GCTGTCTGTCTGTGTTAGTACACTACCCTTTAGGTGGCC 2565
     || || |    ||| |||  |   ||  || | |  ||||||  ||||
2612 GAGAAGCCATGGTTTTTTGTATTGGTCATAACTCAGCCCTTTGGGCGGCC 2661
```

TABLE 2-continued

Comparison of the human and mouse IL-10 receptor
subunits at the nucleotide and amino acid levels. See SEQ ID
NOs 1 through 4.

```
2566 TTTGGGCTTGAGCACTGGCCCA....................GGCTTAGG 2595
     | |||||||| |||| || ||                     || | |
2662 TCTGGGCTTGGGCACCAGCTCATGCCAGCCCCAGAGGGTCAGGGTTGGAG 2711

2596 ACTTATGTCTGCTTTTGCTGCTAATCTCTAACTGCAGACCCAGAGAACAG 2645
     | | || || |||||||||||| || | || |||||||||| | |
2712 GCCTGTGCTTGTGTTTGCTGCTAATGTCCAGCTACAGACCCAGAGGATAA 2761

2646 GGTGCTGGG................CTGACACCTCCGTGTTCAGCTGTGT 2679
     |  |||||                 ||| |    | ||||||||||||||
2762 GCCACTGGGCACTGGGCTGGGGTCCCTGCCTTGTTGGTGTTCAGCTGTGT 2811

2680 GACCTCCGACCAGCAGCTTCCTCAGGGGACTAAAATAATGACTAGGTCAT 2729
     || | ||| ||| |||       ||| || ||        |   |   |
2812 GATTTTGGACTAGCCACTTGTCAGAGGGCCTCAATCTCCCATCTGTGAAA 2861

2730 TCAGAAGTCCCTCATGCTGAATGTTAACCAAGGTGCCCCTGGGGTGATAG 2779
     | ||| |||   ||  ||  | ||  ||    ||       |||| |||
2862 TAAGGA....CTCCACCTTTAGGGGACCCTCCATGTTTGCTGGGTATTAG 2907

2780 TTTAGGTCCTGCAACCTCTGGGTTGGAAGGAAGTGGACTACGGAAGCCAT 2829
          || | ||                  || ||    |         | |
2908 CCAAGCTGGTCC...............TGGGAGAATGCAGATACTGTCCG 2942

2830 CTGTCCCCCTGGGGAGCTTCCACCTCATGCCAGTGTTTCAGAGATCTTGT 2879
       |  || ||  ||||    || |||||||| |  | |||| |
2943 TGGACTACCAAGCTGGCTTGTTTCTTATGCCAGAGGCTAACAGATCCAAT 2992

2880 GGGAGCCTAGGGCCTTGTGCCAAGGGAGCTGCTAGTCCCTGGGGTCTAGG 2929
     |||| | | ||  | |||||||| ||  |    |               |||
2993 GGGAGTCCATGGTGTCATGCCAAGACAGTATCAGACACAGCCCCAGAAGG 3042

2930 G......CTGGTCCCTGCCTCCCTATACTGCGTTTGAGACCTGTCTTCAA 2973
     |       ||| ||||||||||| |||   |  ||||   ||| ||||||
3043 GGGCATTATGGGCCCTGCCTCCCCATAGGCCATTTGGACTCTGCCTTCAA 3092

2974 ATGGAGGCAGTTTGCAGCCCCTAAGCAAGGATGCTGAGAGAAGCAGCAAG 3023
     |  |||||||||  |||  |  | |||  ||| |||| ||| |
3093 ACAAAGGCAGTT..CAGTCCACAGGCATGGAAGCTGTGAGGGACAGGCC 3140

3024 GCTGC..........TGATCCCTGAGCCCAGAGTTTCTCTGAAGCTTTC 3062
     |||              |  || |||| | ||||||| ||| ||| |||
3141 TGTGCGTGCCATCCAGAGTCATCTCAGCCCTGCCTTTCTCTGGAGCATTC 3190

3063 CAAATACAGACTGTGTGACGGGGTGAGGCCAGCCATGAACTTTGGCATCC 3112
      || ||||| ||| | ||  |||||||||||||| |    |    |
3191 TGAAAACAGATATTCTGGCCCAGGGAATCCAGCCATGACCCCCACCCCTC 3240

3113 TGCCGAGAAGGTCAT.GACCCTAATCTGGTACGAGAGCTCCTTCTGGAAC 3161
     |||| |     |||| |    | | ||||||||  || |||| ||||||
3241 TGCCAAAGTACTCTTAGGTGCCAGTCTGGTAACTGAACTCCCTCTGGAGG 3290

3162 TGGGCAAG........CTCTTTGAGACCCCCCTGGAACCTTTATTTATTT 3203
     ||| |           || |  |   ||| ||||||||||||||||
3291 CAGGCTTGAGGGAGGATTCCTCAGGGTTCCCTTGAAAGCTTTATTTATTT 3340

3204 A.TTTGCTCACTTATTTATTGAGGAAGCAGCGTGGCACAGGCGCAAGGCT 3252
     | |||| ||| |||||||||| |||||| ||  ||||| | ||    |
3341 ATTTTGTTCATTTATTTATTGGAGAGGCAGCATTGCACAGTGAAAGAATT 3390
```

TABLE 2-continued

Comparison of the human and mouse IL-10 receptor
subunits at the nucleotide and amino acid levels. See SEQ ID
NOs 1 through 4.

```
3253 CTGGGTCTCTCAGGAG........GTCTAGATTTGCCTGCCCTGTTTCTA 3294
     ||||  |||||||||       ||||| |  || ||   |||||||| |
3391 CTGGATATCTCAGGAGCCCCGAAATTCTAGCTCTGACTTTGCTGTTTCCA 3440

3295 GCTGTGTGACCTTGGGCAAGTCACGTTTCCTCGTGGAGCCTCAGTTTTCC 3344
     |  || |||||||||  |||||| ||||||| ||||| ||||||||||| |
3441 GTGGTATGACCTTGGAGAAGTCACTTATCCTCTTGGAGCCTCAGTTTCCT 3490

3345 TGTCTGTATGCAAAGCTTGGAAATTGAAATGTACCTGACGTGCTCCATCC 3394
     |||| |   ||   ||  |   |  |   |  |    |  ||    | |
3491 CATCTGCAGAATAATGACTGACTTGTCTAATTCATAGGGATGTGAGGTTC 3540

3395 CTAGGAGTGCTGAGTCCCACTGAGAAAGCGGGCACAGACGCCTCAAATGG 3444
     |||||||       |    |   | ||  ||    |
3541 .......TGCTGAGGAAATGGGTATGAATGTGCCTTGAACACAAAGCTCT 3583

3445 AACCACAAGTGGTGTGTG.TTTTCATCCTAATAAAAAGTCAGGTGTTTTG 3493
     |  | ||||| |   || |||| || | ||||||  ||||
3584 GTCAATAAGTGATACATGTTTTTTATTCCAATAAATTGTCAAGACCACA. 3632
``` nucleotides 3632–3647 of human are A; putative polyadenylation
site underlined nucleotide; coding region;
mouse above, human below

```
 80 ATGTTGTCGCGTTTGCTCCCATTCCTCGTCACGATCTCCAGCCTGAGCCT 129
    ||| ||  | |  |  |       | |||  | || || ||||||| | ||
 62 ATGCTGCCGTGCCTCGTAGTGCTGCTGGCGGCGCTCCTCAGCCTCCGTCT 111

130 AGAATTCATTGCATACGGGACAGAACTGCCAAGCCCTTCCTATGTGTGGT 179
    | | | | ||   | ||||||||| |||||| |||| |  | |||||||
112 TGGCTCAGACGCTCATGGGACAGAGCTGCCCAGCCCTCCGTCTGTGTGGT 161

180 TTGAAGCCAGATTTTTCCAGCACATCCTCCACTGGAAACCTATCCCAAAC 229
    ||||||| |||||||||||| ||||||||||||||  || ||||||||
162 TTGAAGCAGAATTTTTCCACCACATCCTCCACTGGACACCCATCCCAAAT 211

230 CAGTCTGAGAGCACCTACTATGAAGTGGCCCTCAAACAGTACGGAAACTC 279
    |||||||   || |||| |||||||||||  | ||||   ||| |||
212 CAGTCTGAAAGTACCTGCTATGAAGTGGCGCTCCTGAGGTATGGAATAGA 261

280 AACCTGGAATGACATCCATATCTGTAGAAAGGCTCAGGCATTGTCCTGTG 329
    ||||||||  ||||  | ||||||    | |||||| | ||||||  ||
262 GTCCTGGAACTCCATCTCCAACTGTAG......CCAGACCCTGTCCTATG 305

330 ATCTCACAACGTTCACCCTGGATCTGTATCACCGAAGCTATGGCTACCGG 379
    |  || |  | | |||  ||||  |||   || |||| |||||||||||
306 ACCTTACCGCAGTGACCTTGGACCTGTACCAC...AGCAATGGCTACCGG 352

380 GCCAGAGTCCGGGCAGTGGACAACAGTCAGTACTCCAACTGGACCACCAC 429
    |||||||| |||||||||||  |||| ||| | |||||||||||||  ||
353 GCCAGAGTGCGGGCTGTGGACGGCAGCCGGCACTCCAACTGGACCGTCAC 402

430 TGAGACTCGCTTCACAGTGGATGAAGTGATTCTGACAGTGGATAGCGTGA 479
     | ||  |||||  ||||||||||||||| ||||||||| |||||||||
403 CAACACCCGCTTCTCTGTGGATGAAGTGACTCTGACAGTTGGCAGTGTGA 452

480 CTCTGAAAGCAATGGACGGCATCATCTATGGGACAATCCATCCCCCCAGG 529
    ||  |       | |||  ||||  ||||  || || | |  |||||||
453 ACCTAGAGATCCACAATGGCTTCATCCTCGGGAAGATTCAGCTACCCAGG 502

530 CCCACGATAACCCCTGCAGGGGATGAGTACGAACAAGTCTTCAAGGATCT 579
```

TABLE 2-continued

Comparison of the human and mouse IL-10 receptor subunits at the nucleotide and amino acid levels. See SEQ ID NOs 1 through 4.

```
      |||| ||| |||| ||    ||    || |||   ||||||  | |
503 CCCAAGATGGCCCCCGCGAATGACACATATGAAAGCATCTTCAGTCACTT  552

580 CCGAGTTTACAAGATTTCCATCCGGAAGTTCTC...AGAACTAAAGAATG  626
    |||||  || |||||  ||||  ||  ||| |    |  | | |  |||
553 CCGAGAGTATGAGATTGCCATTCGCAAGGTGCCGGGAAACTTCACGTTCA  602

627 CAACCAAGAGAGTGAAACAGGAAACCTTCACCCTCACGGTCCCCATAGGG  676
    ||  ||||| |||  ||||| |||| ||||| ||||     | |  ||
603 CACACAAGAAAGTAAAACATGAAAACTTCAGCCTCCTAACCTCTGGAGAA  652

677 GTGAGAAAGTTTTGTGTCAAGGTGCTGCCCCGCTTGGAATCCCGAATTAA  726
    ||| ||  |||  ||||| |||||   ||    | |  |||||||| |||
653 GTGGGAGAGTTCTGTGTCCAGGTGAAACCATCTGTCGCTTCCCGAAGTAA  702

727 CAAGGCAGAGTGGTCGGAGGAGCAGTGTTTACTTATCACGACGGAGCAGT  776
    |||||     ||||||  | ||| ||||  |    ||||  |   |||||
703 CAAGGGGATGTGGTCTAAAGAGGAGTGCATCTCCCTCACCA...GGCAGT  749

777 ATTTCACTGTGACCAACCTGAGCATCTTAGTCATATCTATGCTGCTATTC  826
    |||||||  |||||||||  ||||||| |    |  | | ||||||  ||
750 ATTTCACCGTGACCAACGTCATCATCTTCTTTGCCTTTGTCCTGCTGCTC  799

827 TGTGGAATCCTGG...TCTGTCTGGTTCTCCAGTGGTACATCCGGCACCC  873
    |  |||  |||  |   |||  ||||  ||||||  |||  | |||| ||
800 TCCGGAGCCCTCGCCTACTGCCTGGCCCTCCAGCTGTATGTGCGGCGCCG  849

874 GGGGAAGTTGCCTACAGTCCTGGTCTTCAAGAAGCC...TCACGACTTCT  920
    ||||  |  ||  |   ||||||  |||||||||||||  | |    |||
850 AAAGAAGCTACCCAGTGTCCTGCTCTTCAAGAAGCCCAGCCCCTTCATCT  899

921 TCCCAGCCAACCCTCTCTGCCCAGAAACTCCCGATGCCATTCACATCGTG  970
    || |  |  | |  ||  ||| ||||| || ||   ||   ||||   ||
900 TCATCAGCCAGCGTCCCTCCCCAGAGACCCAAGACACCATCCACCCGCTT  949

971 GACCTGGAGGTTTTCCCAAAGGTGTCACTAGAGCTGAGAGACTCAGTCCT 1020
    ||   |||||  ||    ||||||| ||  ||||||||  |||| | |||
950 GATGAGGAGGCCTTTTTGAAGGTGTCCCCAGAGCTGAAGAACTTGGACCT  999

1021 GCATGGCAGCACCGACAGTGGCTTTGGCAGTGGTAAACCATCACTTCAGA 1070
     |||  ||||||||| |||||||||||||| ||  |||   ||  | ||||
1000 GCACGGCAGCACAGACAGTGGCTTTGGCAGCACCAAGCCATCCCTGCAGA 1049

1071 CTGAAGAGTCCCAATTCCTCCTCCCTGGCTCCCACCCCCAGATACAGGGG 1120
     |||||||| ||||  |||| ||||||||||| ||||||| | ||  |  |
1050 CTGAAGAGCCCCAGTTCCTCCTCCCTGACCCTCACCCCCAGGCTGACAGA 1099

1121 ACTCTGGGAAAAGAAGAGTCTCCAGGGCTACAGGCCACCT.......... 1160
     || ||||||||| |  ||| ||| |||  |||   ||| ||| ||| ||
1100 ACGCTGGGAAACGGGGAGCCCCCTGTGCTGGGGGACAGCTGCAGTAGTGG 1149

1161 ..GTGGGACAACACGGACAGTGGGATCTGCCTGCAGGAGCCCGGCTTAC 1208
       |  |    | |  ||| |||||  ||||||||||||||||| | || |
1150 CAGCAGCAATAGCACAGACAGCGGGATCTGCCTGCAGGAGCCCAGCCTGA 1199

1209 ACTCCAGCATGGGCCCGCCTGGAAGCAGCAGCTTGGATATACCCATCAG 1258
     | |||||  ||||| |||| |||| ||| |||| |  | |   |  |
1200 GCCCCAGCACAGGGCCCACCTGGGAGCAACAGGTGGGAGCAACAGCAGG 1249

1259 GACCAGGATGACAGTGACGTTAACCTAGTCCAGAACTCTCCAGGGCAGCC 1308
```

TABLE 2-continued

Comparison of the human and mouse IL-10 receptor subunits at the nucleotide and amino acid levels. See SEQ ID NOs 1 through 4.

```
      |||||||||||||||| | || || |||| || ||||||   || | | ||
1250 GGCCAGGATGACAGTGGCATTGACTTAGTTCAAAACTCTGAGGGCCGGGC 1299

1309 TAAGTACACACAGGATGCATCTGCCTTGGGCCATGTCTGTCTCCTAGAAC 1358
      | | |||||||||| || || |||||||||||  | ||| || |||
1300 TGGGGACACACAGGGTGGCTCGGCCTTGGGCCACCACAGTCCCCCGGAGC 1349

1359 CTAAAGCCCCTGAGGAGAAAGACCAAGTCATGGTGACATTCCAGGGCTAC 1408
      || | |  |||| ||| |||||| ||    ||| |||||||||||| |||
1350 CTGAGGTGCCTGGGGAAGAAGACCCAGCTGCTGTGGCATTCCAGGGTTAC 1399

1409 CAGAAACAGACCAGATGGAAGGCAGAGGCAGCAGGCCCAGCAGAATGCTT 1458
      | ||  ||||||||||||   ||||    |||  |    ||| ||||||
1400 CTGAGGCAGACCAGATGTGCTGAAGAGAAGGCAACCAAGACAGGCTGCCT 1449

1459 GGACGAAGAGATTCCCTTGACAGATGCCTTTGATCCTGAACTTGGGGTAC 1508
      ||| ||||     ||||||||||||||||| ||| || || ||| |
1450 GGAGGAAGAATCGCCCTTGACAGATGGCCTTGGCCCCAAATTCGGGAGAT 1499

1509 ACCTGCAGGATGATTTGGCTTGGCCTCCACCAGCTCTGGCCGCAGGTTAT 1558
      ||||     |||||     |    ||  ||||||||||  ||||||   || |||
1500 GCCTGGTTGATGAGGCAGGCTTGCATCCACCAGCCCTGGCCAAGGGCTAT 1549

1559 TTGAAACAGGAGTCTCAAGGGATGGCTTCTGCTCCACCAGGGACACCAAG 1608
      ||||||||||  ||| ||  ||| ||    ||| |  |||||  | ||||
1550 TTGAAACAGGATCCTCTAGAAATGACTCTGGCTTCCTCAGGGGCCCCAAC 1599

1609 TAGACAGTGGAATCAACTGACCGAAGAGTGGTCACTCCTGGGTGTGGTTA 1658
      |||||||||| ||  || || || ||||||||||||  || || |
1600 GGGACAGTGGAACCAGCCCACTGAGGAATGGTCACTCCTGGCCTTGAGCA 1649

1659 GCTGTGAAGATCTAAGCATAGAAAGTTGGAGGTTTGCCCATAAACTTGAC 1708
      ||||   || ||  | |||     ||||| |||||||||| |  |||| |
1650 GCTGCAGTGACCTGGGAATATCTGACTGGAGCTTTGCCCATGACCTTGCC 1699

1709 CCTCTGGACTGTGGGGCAGCCCCTGGTGGCCTCCTGGATAGCCTTGGCTC 1758
      ||||| | |||||  ||||||||| |||||  ||||||| ||| || |||
1700 CCTCTAGGCTGTGTGGCAGCCCCAGGTGGTCTCCTGGGCAGCTTTAACTC 1749

1759 TAACCTGGTCACCCTGCCGTTGATCTCCAGCCTGCAGGTAGAAGAA     1804
      |||||||||||||||||  | |||||| |||||||||| |   ||
1750 AGACCTGGTCACCCTGCCCCTCATCTCTAGCCTGCAGTCAAGTGAG     1795
``` amino acid sequence comparison; mouse above, human below
```
  1 MLSRLLPFLVTISSLSLEFIAYGTELPSPSYVWFEARFFQHILHWKPIPN   50
    ||. |:.:|...: ||.|:  |.|||||||. ||||| ||:|||||.||||
  1 MLPCLVVLLAALLSLRLGSDAHGTELPSPPSVWFEAEFFHHILHWTPIPN   50
                                                     ↑

51 QSESTYYEVALKQYGNSTWNDIHICRKAQALSCDLTTFTLDLYHRSYGYR  100
    |||||:||||| .|| ..||.| | .|.|:|||..|||||| | |||
 51 QSESTCYEVALLRYGIESWNSISNC..SQTLSYDLTAVTLDLYH.SNGYR   97

101 ARVRAVDNSQYSNWTTTETRFTVDEVILTVDSVTLKAMDGIIYGTIHPPR  150
    ||||||.|..||||.:|||.||||.||||.|||:||.|.  :|:|.|.|: ||
 98 ARVRAVDGSRHSNWTVTNTRFSVDEVTLTVGSVNLEIHNGFILGKIQLPR  147

151 PTITPAGDEYEQVFKDLRVYKISIRKF.SELKNATKRVKQETFTLTVPIG  199
    |.:.||.|.|| :|...:| |.|.|||. :::. . |:||:|.|.| ..:
148 PKMAPANDTYESIFSHFREYEIAIRKVPGNFTFTHKKVKHENFSLLTSGE  197
```

TABLE 2-continued

Comparison of the human and mouse IL-10 receptor
subunits at the nucleotide and amino acid levels. See SEQ ID
NOs 1 through 4.

```
200 VRKFCVKVLPRLESRINKAEWSEEQCLLITTEQYFTVTNLSILVISMLLF  249
    | .|||.| |.:.|| ||: ||.|:|: : | ||||||||: |:.  :||:
198 VGEFCVQVKPSVASRSNKGMWSKEECISL.TRQYFTVTNVIIFFAFVLLL  246
                                      →TM

250 CGILV.CLVLQWYIRHPGKLPTVLVFKKPHDF.FPANPLCPETPDAIHIV  297
    :| |. ||.||:|:|:. |||.||:|||| .| | ... :|||.|.|| :
247 SGALAYCLALQLYVRRRKKLPSVLLFKKPSPFIFISQRPSPETQDTIHPL  296
         TM←

298 DLEVFPKVSLELRDSVLHGSTDSGFGSGKPSLQTEESQFLLPGSHPQIQG  347
    | |.| ||| ||:: ||||||||||||.||||||||.||||:.||| :
297 DEEAFLKVSPELKNLDLHGSTDSGFGSTKPSLQTEEPQFLLPDPHPQADR  346

348 TLGKEESPGLQATC....GDNTDSGICLQEPGLHSSMGPAWKQQLGYTHQ  393
    |||.:|.|.|...|    ::.|||||||||||:| .| ||.|.||:| . .
347 TLGNGEPPVLGDSCSSGSNSTDSGICLQEPSLSPSTGPTWEQQVGSNSR  396

394 DQDDSDVNLVQNSPGQPKYTQDASALGHVCLLEPKAPEEKDQVMVTFQGY  443
    :||||:::|||||.|.: ||::|||||  :  ||..:|.|.. |.||||
397 GQDDSGIDLVQNSEGRAGDTQGGSALGHHSPPEPEVPGEEDPAAVAFQGY  446

444 QKQTRWKAEAAGPAECLDEEIPLTDAFDPELGVHLQDDLAWPPPALAAGY  493
    :|||  .| |...:||:|| ||||:::|.:|  | |: ::.||||| ||
447 LRQTRCAEEKATKTGCLEEESPLTDGLGPKFGRCLVDEAGLHPPALAKGY  496

494 LKQESQGMASAPPGTPSRQWNQLTEEWSLLGVVSCEDLSIESWRFAHKLD  543
    |||:. :|. |..|.|. |||| ||||||||:: ||.||:|..|.|||.|.
497 LKQDPLEMTLASSGAPTGQWNQPTEEWSLLALSSCSDLGISDWSFAHDLA  546

544 PLDCGAAPGGLLDSLGSNLVTLPLISSLQVEE  575
    ||:|.||||||||:|..|:||||||||||| .|
547 PLGCVAAPGGLLGSFNSDLVTLPLISSLQSSE  578
``` for human: predicted signal cleavage site indicated by arrow;
hydrophobic memb- membrane spanning region indicated 236–260;
potential glycosylation sites (N-X-S/T)underlined, cytoplasmic
motif underline twice The present invention also encompasses proteins or peptides having substantial amino acid sequence homology with the amino acid sequences in Table 2, but excluding any protein or peptide which exhibits substantially the same or lesser amino acid sequence homology than do known G-CSF, GM-CSF, EPO, TNF, IFN-γ, IL-2, IL-3, IL-4, IL-5, IL-6, or IL-7 receptor component sequences.

A polypeptide "fragment", or "segment", is a stretch of amino acid residues of at least about 8 amino acids, generally at least 10 amino acids, more generally at least 12 amino acids, often at least 14 amino acids, more often at least 16 amino acids, typically at least 18 amino acids, more typically at least 20 amino acids, usually at least 22 amino acids, more usually at least 24 amino acids, preferably at least 26 amino acids, more preferably at least 28 amino acids, and, in particularly preferred embodiments, at least about 30 or more amino acids. Typically, fragments of homologous receptor components will exhibit substantial identity.

Amino acid sequence homology, or sequence identity, is determined by optimizing residue matches, if necessary, by introducing gaps as required. This changes when considering conservative substitutions as matches. Conservative substitutions typically include substitutions within the following groups: [glycine, alanine]; [valine, isoleucine, leucine]; [aspartic acid, glutamic acid]; [asparagine, glutamine]; [serine, threonine]; [lysine, arginine]; and [phenylalanine, tyrosine]. Homologous amino acid sequences are intended to include natural allelic and interspecies variations in each respective receptor sequence. Typical homologous proteins or peptides will have from 25–100% homology (if gaps can be introduced), to 50–100% homology (if conservative substitutions are included) with the amino acid sequence of Table 2. Homology measures will be at least about 50%, generally at least 56%, more generally at least 62%, often at least 67%, more often at least 72%, typically at least 77%, more typically at least 82%, usually at least 86%, more usually at least 90%, preferably at least 93%, and more preferably at least 96%, and in particularly preferred embodiments, at least 98% or more. Some homologous proteins or peptides, such as the various receptor subtypes, will share various biological activities with the components of a receptor for IL-10, e.g., the embodiments provided in Table 2. As used herein, the term "biological activity" is defined as including, without limitation, ligand (e.g., IL-10-like protein) binding, cross-reactivity with antibodies raised against each respective receptor component, and ligand dependent signal transduction. A "ligand-related activity" refers either to ligand binding itself, or to biological activities which are mediated by ligand binding, including, e.g., second messenger modulation, $Ca^{++}$ sequestration, phosphorylation, protein associations, etc.

The term "ligand" refers to molecules, usually members of the family of cytokine-like peptides, that bind to the receptor via the segments involved in peptide ligand binding. Also, a ligand is a molecule which serves either as a natural ligand to which the receptor, or an analog thereof, binds, or a molecule which is a functional analog of a natural ligand. The functional analog may be a ligand with structural modifications, or may be a wholly unrelated molecule which has a molecular shape which interacts with the appropriate ligand binding determinants. The ligands may serve as agonists or antagonists, see, e.g., Goodman, et al. (eds.) (1990) *Goodman & Gilman's: The Pharmacoloaical Bases of Therapeutics* (8th ed.), Pergamon Press.

Solubility of a polypeptide or fragment depends upon the environment and the polypeptide. Many parameters affect polypeptide solubility, including temperature, electrolyte environment, size and molecular characteristics of the polypeptide, and nature of the solvent. Typically, the temperature at which the polypeptide is used ranges from about 4° C. to about 65° C. Usually the temperature at use is greater than about 18° C. and more usually greater than about 22° C. For diagnostic purposes, the temperature will usually be about room temperature or warmer, but less than the denaturation temperature of components in the assay. For therapeutic purposes, the temperature will usually be body temperature, typically about 37° C. for humans, though under certain situations the temperature may be raised or lowered in situ or in vitro.

The electrolytes will usually approximate in situ physiological conditions, but may be modified to higher or lower ionic strength where advantageous. The actual ions may be modified to conform to standard buffers used in physiological or analytical contexts.

The size and structure of the polypeptide should generally be in a substantially stable state, and usually not in a denatured state. The polypeptide may be associated with other polypeptides in a quaternary structure, e.g., to confer solubility, or associated with lipids or detergents in a manner which approximates its natural lipid bilayer interactions.

The solvent will usually be a biologically compatible buffer, of a type used for preservation of biological activities, and will usually approximate a physiological solvent. Usually the solvent will have a neutral pH, typically between about 5 and 10, and preferably about 7.5. On some occasions, a detergent will be added, typically a mild non-denaturing one, e.g., CHS or CHAPS.

One crude measure of solubility is based upon sedimentation rates, e.g., Svedberg units, which are a measure of the sedimentation velocity of a molecule under particular conditions. The determination of the sedimentation velocity was classically performed in an analytical ultracentrifuge, but is typically now performed in a standard ultracentrifuge. See, Freifelder (1982) *Physical Biochemistry* (2d ed.), W. H. Freeman; and Cantor and Schimmel (1980) *Biophysical Chemistry*, parts 1–3, W. H. Freeman & Co., San Francisco; each of which is hereby incorporated herein by reference. As a crude determination, a sample containing a putatively soluble polypeptide is spun in a standard full sized ultracentrifuge at about 50K rpm for about 10 minutes, and soluble molecules will remain in the supernatant. A soluble particle or polypeptide will typically be less than about 30 S, more typically less than about 15 S, usually less than about 10 S, more usually less than about 6 S, and, in particular embodiments, preferably less than about 4 S, and more preferably less than about 3 S.

Particularly useful soluble fragments of the receptor component will be ligand binding fragments. As the protein appears to contain extracellular domains with which the ligand should bind, a protein comprising the extracellular segments amino proximal to the transmembrane helix segment running from residues 217–243 would exhibit such binding activity. Fusions of the extracellular domain with other proteins, and shorter segments can be easily tested for ligand binding activity. Alternatively, fragments consisting of the intracellular domain should also be of interest.

Figure 18:
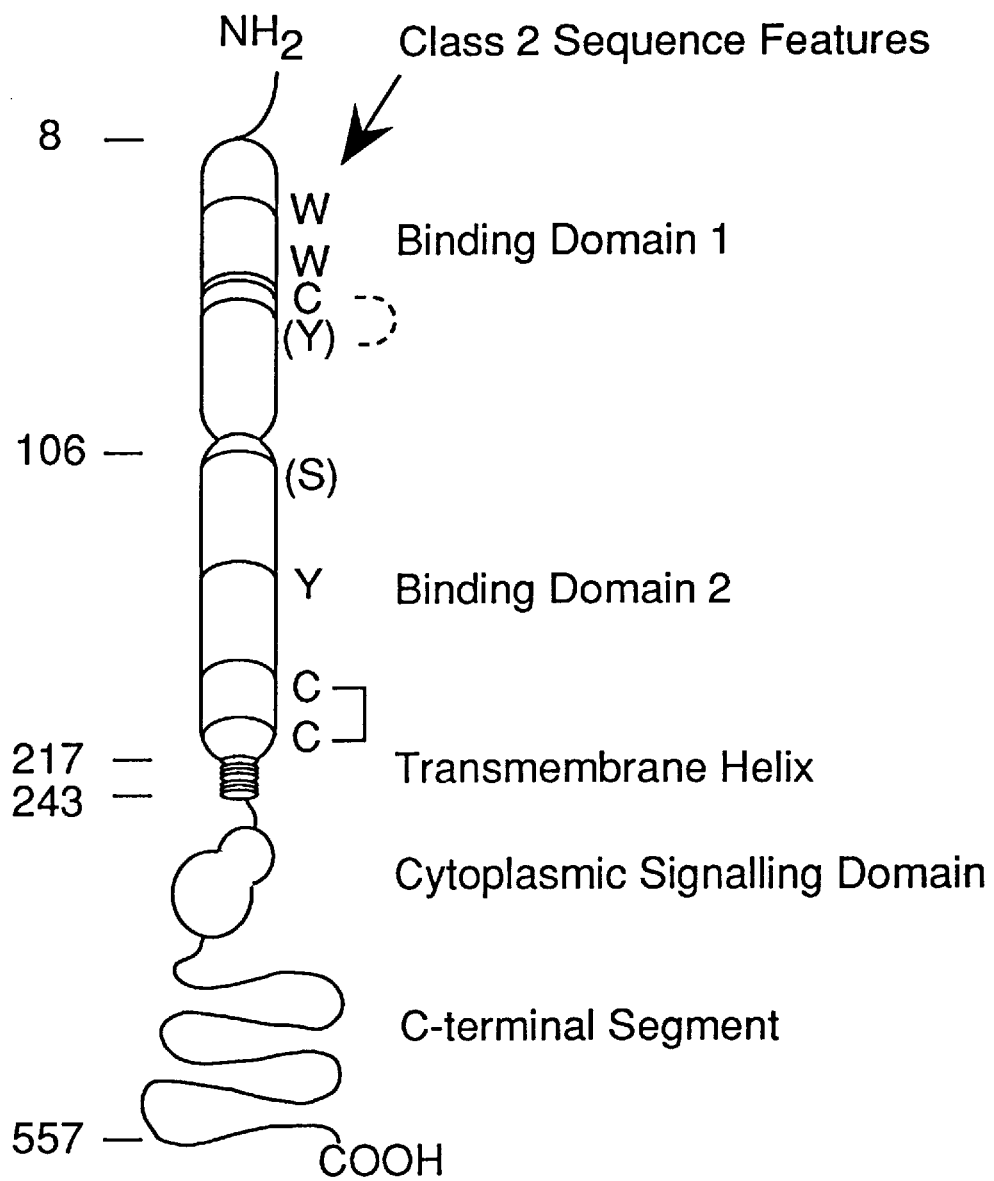
FIG. 18 shows a cartoon of the structure of the IL-10 receptor, its domain structure, and structural features which suggest a class 2 cytokine receptor classification.
Figure 19:
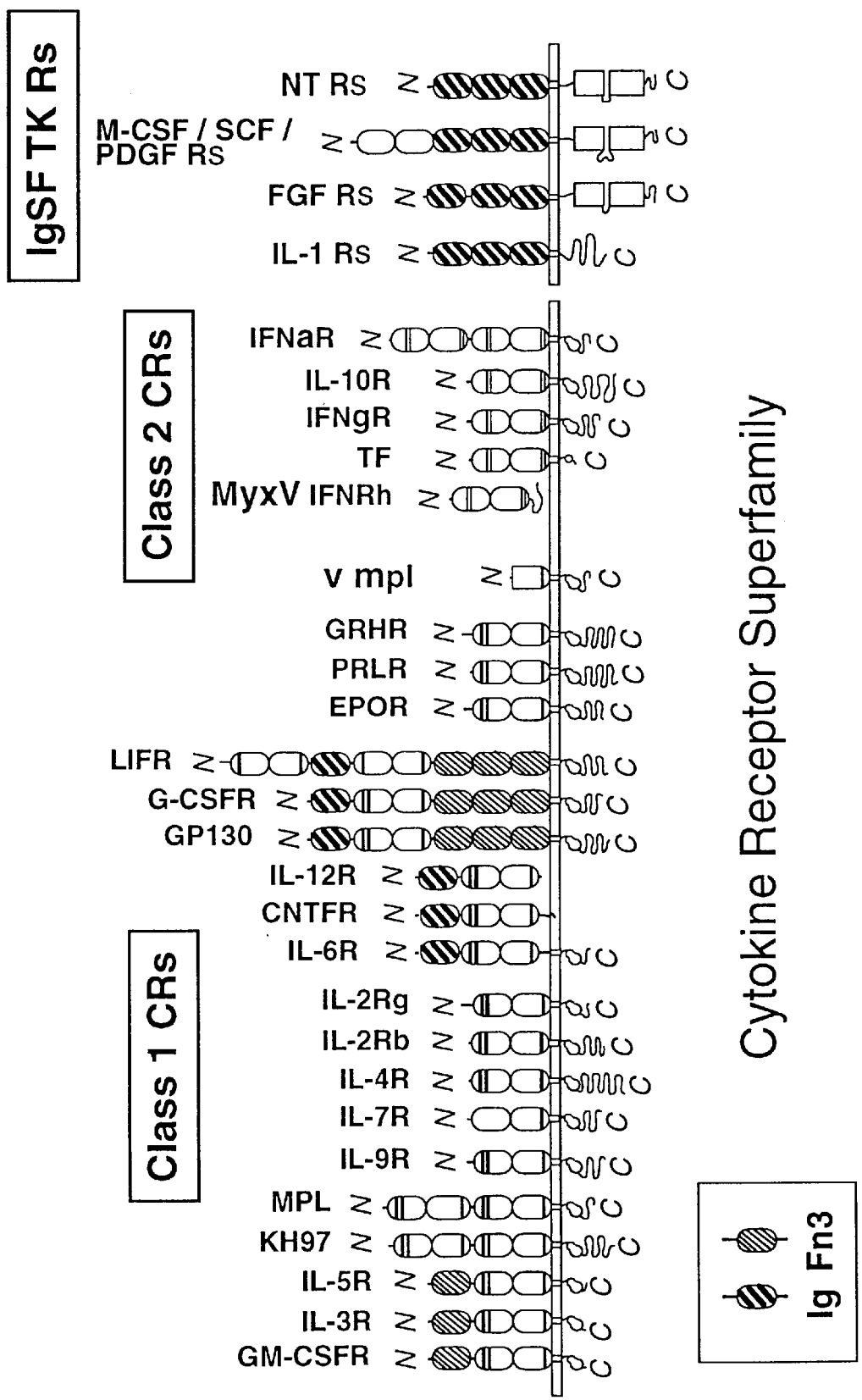
FIG. 19 shows a cartoon of members of the cytokine receptor superfamily.

In analysis of the polypeptide sequences of the human and mouse IL-10 receptors, the sequences exhibit 70–75% homology at the DNA and protein sequence levels. See, e.g., Table 2. On the basis of distinctive structural motifs, it is recognized that the IL-10 receptor polypeptides encoded herein are members of the class 2 group of the cytokine receptor superfamily. See, e.g., Bazan (1990) *Immunology Today* 11:350–354; and Bazan (1990) *Proc. Nat'l Acad. Sci. USA* 87:6934–6938; and FIGS. 18 and 19.

The characteristic motifs of the class 1 receptors include an amino-terminal set of four conserved cystines and one tryptophan residue, and a carboxy-terminal (membrane-proximal) collection of spaced aromatic residues. The motifs characteristic of the class 2 receptors are a conserved tryptophan and the second cysteine pair in the amino-terminal half, a WSxWS box analog in the carboxy-terminal half, and a second conserved cysteine pair.

The other members of the Class 2 are the receptors for interferon-α (IFN-α), for interferon-γ (IFN-γ), and for tissue factor, and for a second soluble viral IFN receptor homolog. The IL-10 receptor components described herein are particularly closely related to the interferon-γ receptor. These domain structure similarities suggest that the mechanisms of action of the IL-10 on its receptor may be related to similar mechanisms in the interaction of IFN-γ with its receptor. See, e.g., Levy, et al. (1990) *New Biologist* 2:923–928; Sen, et al. (1992) *J. Biol, Chem.* 267:5017–5020; and Uze, et al. (1992) *Proc. Nat'l Acad. Sci. USA* 89:4774–4778.

For example, the antagonistic effect of IL-10 on macrophage activation by IFN-γ may directly intervene in the signal cascade of IFN response. This may be effected by interaction of a component in the IFN signal pathway with a component in the IL-10 pathway. Sharing of components in the two pathways is a real possibility, including direct structural overlap of one or more components in active receptor complexes, e.g., shared β-like subunits. Alternatively, the structural similarities of the IFN and IL-10 receptor components will predict that regions of receptor structure critical in one pathway and conserved in the other will have like importance. This predictability extends to both ligand molecular surface shapes and to intracellular features likely to interact with downstream signal pathway components. This suggests methods of modulating a biological effect of IL-10, comprising a step of interfering with signal transduction of an interferon receptor, including, e.g., agonists or antagonists of an IFN, or homologous IL-10 receptor variants to IFN receptor mutants.

II. Nucleic Acids

This invention contemplates use of isolated nucleic acids, e.g., DNA, or fragments which encode these receptor components for IL-10-like peptides, e.g., each respective species variant of these receptors, or any fragment thereof, to encode a biologically active counterpart receptor polypeptide. In addition, this invention covers isolated or recombinant DNA which encodes a biologically active protein or polypeptide having receptor activity and which is capable of hybridizing under appropriate conditions with the DNA sequences as in SEQ ID NO: 1 or 3. Said biologically active protein or polypeptide can be a receptor itself, or fragment, and comprise an amino acid sequence as in SEQ ID NO: 2 or 4 or Table 2. Further, this invention covers the use of isolated or recombinant DNA, or fragments thereof, which encode proteins which are homologous to each respective species variant or receptor or which was isolated using cDNA encoding a receptor for IL-10 as a probe. The isolated DNA can have the respective regulatory sequences in the 5' and 3' flanks, e.g., promoters, enhancers, poly-A addition signals, and others.

An "isolated" nucleic acid is a nucleic acid, e.g., an RNA, DNA, or a mixed polymer, which is substantially separated from other components which naturally accompany a native sequence, e.g., ribosomes, polymerases, and flanking genomic sequences from the originating species. The term embraces a nucleic acid sequence which has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules, but will, in some embodiments, contain minor heterogeneity. This heterogeneity is typically found at the polymer ends or portions not critical to a desired biological function or activity.

A "recombinant" nucleic acid is defined either by its method of production or its structure. In reference to its method of production, e.g., a product made by a process, the process is use of recombinant nucleic acid techniques, e.g., involving human intervention in the nucleotide sequence. Alternatively, it can be a nucleic acid made by generating a sequence comprising fusion of two fragments which are not naturally contiguous to each other, but is meant to exclude products of nature, e.g., naturally occurring mutants. Thus, for example, products made by transforming cells with any unnaturally occurring vector is encompassed, as are nucleic acids comprising sequence derived using any synthetic oligonucleotide process. Such is often done to replace a codon with a redundant codon encoding the same or a conservative amino acid, while typically introducing or removing a sequence recognition site. Alternatively, it is performed to join together nucleic acid segments of desired functions to generate a single genetic entity comprising a desired combination of functions not found in the commonly available natural forms. Restriction enzyme recognition sites are often the target of such artificial manipulations, but other site specific targets, e.g., promoters, DNA replication sites, regulation sequences, control sequences, or other useful features may be incorporated by design. A similar concept is intended for a recombinant, e.g., fusion, polypeptide. Specifically included are synthetic nucleic acids which, by genetic code redundancy, encode similar polypeptides to fragments of these receptors, and fusions of sequences from various different receptors or proteins.

A "fragment" in a nucleic acid context is a contiguous segment of at least about 17 nucleotides, generally at least 20 nucleotides, more generally at least 23 nucleotides, ordinarily at least 26 nucleotides, more ordinarily at least 29 nucleotides, often at least 32 nucleotides, more often at least 35 nucleotides, typically at least 38 nucleotides, more typically at least 41 nucleotides, usually at least 44 nucleotides, more usually at least 47 nucleotides, preferably at least 50 nucleotides, more preferably at least 53 nucleotides, and in particularly preferred embodiments will be at least 56 or more nucleotides.

A DNA which codes for a receptor for IL-10 will be particularly useful to identify genes, mRNA, and cDNA species which code for related or homologous receptors, as well as nucleic acids which code for species variants of these receptor components.

Preferred probes for screens are those regions of the receptors which are conserved between different species variants. Conserved regions will be identified by comparisons of completed sequences to one another.

This invention further covers recombinant DNA molecules and fragments having a DNA sequence identical to or highly homologous to the isolated DNAs set forth herein. In particular, the sequences will often be operably linked to DNA segments which control transcription, translation, and DNA replication. Genomic sequences containing introns are also made available, along with methodologies to isolate them.

Homologous nucleic acid sequences, when compared, exhibit significant similarity. The standards for homology in nucleic acids are either measures for homology generally used in the art by sequence comparison or based upon hybridization conditions. The hybridization conditions are described in greater detail below, but are further limited by the homology to other known receptors for cytokines, e.g., the above described receptor components. Homology measures will be limited, in addition to any stated parameters, to exceed any such similarity to these receptors, e.g., GM-CSF, IL-3, IL-4, and IL-5 receptor components.

Substantial homology in the nucleic acid sequence comparison context means either that the segments, or their complementary strands, when compared, are identical when optimally aligned, with appropriate nucleotide insertions or deletions, in at least about 50% of the nucleotides, generally at least 56%, more generally at least 59%, ordinarily at least 62%, more ordinarily at least 65%, often at least 68%, more often at least 71%, typically at least 74%, more typically at least 77%, usually at least 80%, more usually at least about 85%, preferably at least about 90%, more preferably at least about 95 to 98% or more, and in particular embodiments, as high as about 99% or more of the nucleotides. Alternatively, substantial homology exists when the segments will hybridize under selective hybridization conditions, to a strand, or its complement, typically using a sequence derived from Table 2. Typically, selective hybridization will occur when there is at least about 55% homology over a stretch of at least about 14 nucleotides, preferably at least about 65%, more preferably at least about 75%, and most preferably at least about 90%. See, Kanehisa (1984) *Nuc. Acids Res.* 12:203–213, which is incorporated herein by reference. The length of homology comparison, as described, may be over longer stretches, and in certain embodiments will be over a stretch of at least about 17 nucleotides, usually at least about 20 nucleotides, more usually at least about 24 nucleotides, typically at least about 28 nucleotides, more typically at least about 40 nucleotides, preferably at least about 50 nucleotides, and more preferably at least about 75 to 100 or more nucleotides.

Stringent conditions, in referring to homology in the hybridization context, will be stringent combined conditions of salt, temperature, organic solvents, and other parameters typically controlled in hybridization reactions. Stringent temperature conditions will usually include temperatures in excess of about 30° C., more usually in excess of about 37°

C., typically in excess of about 45° C., more typically in excess of about 55° C., preferably in excess of about 65° C., and more preferably in excess of about 70° C. Stringent salt conditions will ordinarily be less than about 1000 mM, usually less than about 500 mM, more usually less than about 400 mM, typically less than about 300 mM, preferably less than about 200 mM, and more preferably less than about 150 mM. However, the combination of parameters is much more important than the measure of any single parameter. See, e.g., Wetmur and Davidson (1968) *J. Mol. Biol.* 31:349–370, which is hereby incorporated herein by reference.

Isolation and characterization of these nucleic acids allow use thereof to make variants and mutants. It will also allow production of vector constructs useful, e.g., for making transgenic cells, including homologous recombination, e.g., gene "knock-out" animals, and for gene therapy. See, e.g., Goodnow (1992) "Transgenic Animals" in Roitt (ed.) *Encyclopedia of Immunology* Academic Press, San Diego, pp. 1502–1504; Travis (1992) Science 256:1392–1394; Kuhn, et al. (1991) *Science* 254:707–710; Capecchi (1989) *Science* 244:1288; Robertson (1987) (ed.) *Teratocarcinomas and Embryonic Stem Cells: A Practical Approach* IRL Press, Oxford; and Rosenberg (1992) *J. Clinical Oncology* 10:180–199; which are each incorporated herein by reference.

III. Receptor Variants

The isolated receptor DNAs can be readily modified by nucleotide substitutions, nucleotide deletions, nucleotide insertions, and inversions of nucleotide stretches. These modifications result in novel DNA sequences which encode these receptors, their derivatives, or proteins having IL-10 receptor activity. These modified sequences can be used to produce mutant receptors or to enhance the expression of receptor species. Enhanced expression may involve gene amplification, increased transcription, increased translation, and other mechanisms. Such mutant receptor derivatives include predetermined or site-specific mutations of the respective receptor or its fragments. A "mutant IL-10 receptor" encompasses a polypeptide otherwise falling within the homology definition of the IL-10 receptor as set forth above, but having an amino acid sequence which differs from that IL-10 receptor most commonly as found in nature, whether by way of an amino acid deletion, substitution, or insertion. In particular, "site specific mutant IL-10 receptor" is a protein having homology with a receptor of Table 2, and as sharing various biological activities with those receptor components. Similar proteins and nucleic acids should be available from other warm blooded animals, e.g., mammals and birds. As stated before, it is emphasized that descriptions are generally meant to encompass species and allelic variants of these receptor components, not limited to the IL-10 receptor examples specifically discussed.

Although site specific mutation sites are predetermined, mutants need not be site specific. IL-10 receptor mutagenesis can be conducted by making amino acid insertions or deletions. Substitutions, deletions, insertions, or any combinations may be generated to arrive at a final construct. Insertions include but are not limited to amino- or carboxy-terminal fusions. Random mutagenesis can be conducted at a target codon and the expressed IL-10 receptor mutants can then be screened for the desired activity. Methods for making substitution mutations at predetermined sites in DNA having a known sequence are well known in the art, e.g., by M13 primer mutagenesis. See also Sambrook, et al. (1989) and Ausubel, et al. (1987 and Supplements).

The mutations in the DNA normally should not place coding sequences out of reading frames and preferably will not create complementary regions that could hybridize to produce secondary mRNA structure such as loops or hairpins.

The present invention also provides recombinant proteins, e.g., heterologous fusion proteins using segments from these receptor components. A heterologous fusion protein is a fusion of proteins or segments which are naturally not normally fused in the same manner. Thus, the fusion product of an immunoglobulin with a receptor polypeptide is a continuous protein molecule having sequences fused in a typical peptide linkage, e.g., typically made as a single translation product and exhibiting properties derived from each source peptide. A similar concept applies to heterologous nucleic acid sequences.

In addition, new constructs may be made from combining similar functional domains from other proteins. For example, ligand-binding or other segments may be "swapped" between different new fusion polypeptides or fragments. See, e.g., Cunningham, et al. (1989) *Science* 243:1330–1336; and O'Dowd, et al. (1988) *J. Biol. Chem.* 263:15985–15992, each of which is incorporated herein by reference. Thus, new chimeric polypeptides exhibiting new combinations of specificities will result from the functional linkage of ligand-binding specificities and intracellular regions. For example, the ligand binding domains from other related receptors may be added or substituted for other binding domains of these receptors. The resulting protein will often have hybrid function and properties.

The phosphoramidite method described by Beaucage and Caruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

The present invention provides means to produce fusion proteins. Various receptor variants may have slightly different functions or biological activities, even though they share significant structural similarities. Dissection of structural elements which effect the various physiological functions or biological activities provided by the receptors is possible using standard techniques of modern molecular biology, particularly in comparing variants within the related family of cytokine receptors. See, e.g., the homolog-scanning mutagenesis technique described in Cunningham, et al. (1989) *Science* 243:1339–1336; and approaches used in O'Dowd, et al. (1988) *J. Biol. Chem.* 263:15985–15992; and Lechleiter, et al. (1990) *EMBO J.* 9:4381–4390; each of which is incorporated herein by reference.

In particular, ligand binding segments can be substituted between receptors to determine what structural features are important in both ligand binding affinity and specificity. The segments of receptor accessible to an extracellular ligand would be primary targets of such analysis. An array of different receptor variants, e.g., allelic, will be used to screen for ligands exhibiting combined properties of interaction with them. Intracellular functions would probably involve segments of the receptor which are normally accessible to the cytosol. However, receptor internalization may occur under certain circumstances, and interaction between intracellular components and the designated "extracellular" segments may occur. These intracellular functions usually involve signal transduction from ligand binding. The specific segments of interaction of receptor with other proteins may be identified by mutagenesis or direct biochemical means, e.g., cross-linking or affinity methods. Structural analysis by crystallographic or other physical methods will also be applicable. Identification of the similarities and differences between receptor variants exhibiting distinct functions will lead to new diagnostic and therapeutic reagents or treatments.

Further study of the expression and control of receptor variants will be useful. The controlling elements associated with the receptors could exhibit differential developmental, tissue specific, or other expression patterns. Upstream or downstream genetic regions, e.g., control elements, are of interest.

Structural studies of the receptor variants will lead to design of new ligands, particularly analogs exhibiting agonist or antagonist properties. This can be combined with previously described screening methods to isolate ligands exhibiting desired spectra of activities.

Expression in other cell types will often result in glycosylation differences in a particular receptor. Various receptor variants may exhibit distinct biological activities based upon structural differences other than amino acid sequence. Differential modifications may be responsible for differential function, and elucidation of the effects are now made possible.

Thus, the present invention provides various receptors, e.g., species variants and fusion proteins, for IL-10, and reagents developed from them. Although the foregoing description has focused primarily upon the human and mouse IL-10 receptors, those of skill in the art will immediately recognize that the invention encompasses receptors from various different mammalian species.

IV. Making Receptor

A nucleic acid which encodes the IL-10 receptor or fragments thereof is available in the pMR29 and pSW8.1 clones, or can be obtained by chemical synthesis, screening cDNA libraries, or by screening genomic libraries prepared from a wide variety of cell lines or tissue samples.

This DNA can be expressed in a wide variety of host cells for the synthesis of a full-length receptor or fragments of a receptor which can in turn, for example, be used to generate polyclonal or monoclonal antibodies; for binding studies; for construction and expression of modified receptor molecules; and for structure/function studies. Each receptor or its fragments can be expressed in host cells that are transformed or transfected with appropriate expression vectors. These molecules can be substantially free of protein or cellular contaminants, other than those derived from the recombinant host, and therefore are particularly useful in pharmaceutical compositions when combined with a pharmaceutically acceptable carrier and/or diluent. The receptor, or portions thereof, may be expressed as fusions with other proteins.

Expression vectors are typically self-replicating DNA or RNA constructs containing the desired receptor gene or its fragments, usually operably linked to suitable genetic control elements that are recognized in a suitable host cell. These control elements are capable of effecting expression within a suitable host. The specific type of control elements necessary to effect expression will depend upon the eventual host cell used. Generally, the genetic control elements can include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also usually contain an origin of replication that allows the vector to replicate independently of the host cell.

The vectors of this invention contain DNA which encodes a receptor for an IL-10-like peptide, or a fragment thereof encoding a biologically active receptor polypeptide. The DNA can be under the control of a viral promoter and can encode a selection marker. This invention further contemplates use of such expression vectors which are capable of expressing eukaryotic cDNA coding for a receptor in a prokaryotic or eukaryotic host, where the vector is compatible with the host and where the eukaryotic cDNA coding for the receptor is inserted into the vector such that growth of the host containing the vector expresses the cDNA in question. Usually, expression vectors are designed for stable replication in their host cells or for amplification to greatly increase the total number of copies of the desirable gene per cell. It is not always necessary to require that an expression vector replicate in a host cell, e.g., it is possible to effect transient expression of the IL-10 receptor or its fragments in various hosts using vectors that do not contain a replication origin that is recognized by the host cell. It is also possible to use vectors that cause integration of IL-10 receptor or its fragments into the host DNA by recombination.

Vectors, as used herein, comprise plasmids, viruses, bacteriophage, integratable DNA fragments, and other vehicles which enable the integration of DNA fragments into the genome of the host. Expression vectors are specialized vectors which contain genetic control elements that effect expression of operably linked genes. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual,* Elsevier, N.Y., and Rodriquez, et al. (eds.) *Vectors: A Survey of Molecular Cloning Vectors and Their Uses,* Buttersworth, Boston, 1988, which are incorporated herein by reference.

Transformed cells are cells, preferably mammalian, that have been transformed or transfected with receptor vectors constructed using recombinant DNA techniques. Transformed host cells usually express the receptor or its fragments, but for purposes of cloning, amplifying, and manipulating its DNA, do not need to express the receptor. This invention further contemplates culturing transformed cells in a nutrient medium, thus permitting the receptor or fragments, e.g., a soluble protein, to accumulate in the culture. The receptor proteins can be recovered from the cells or from the culture medium.

For purposes of this invention, DNA sequences are operably linked when they are functionally related to each other. For example, DNA for a presequence or secretory leader is operably linked to a polypeptide if it is expressed as a preprotein or participates in directing the polypeptide to the cell membrane or in secretion of the polypeptide. A promoter is operably linked to a coding sequence if it controls the transcription of the polypeptide; a ribosome binding site is operably linked to a coding sequence if it is positioned to permit translation. Usually, operably linked means contiguous and in reading frame, however, certain genetic elements such as repressor genes are not contiguously linked but still bind to operator sequences that in turn control expression.

Suitable host cells include prokaryotes, lower eukaryotes, and higher eukaryotes. Prokaryotes include both gram negative and gram positive organisms, e.g., *E. coli* and *B. subtilis.* Lower eukaryotes include yeasts, e.g., *S. cerevisiae* and *Pichia,* and species of the genus *Dictyostelium.* Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the receptor or its fragments include, but are not limited to, such vectors as those containing the lac promoter (pUC-series); trp promoter (pBR322-trp); Ipp promoter (the pIN-series); lambda-pP or pR promoters (pOTS); or hybrid promoters such as ptac (pDR540). See Brosius, et al. (1988) "Expression Vectors Employing Lambda-, trp-, lac-, and Ipp-derived Promoters", in *Vectors: A Survey of Molecular Cloning Vectors and Their Uses,* (eds. Rodriguez and Denhardt), Buttersworth, Boston, Chapter 10, pp. 205–236, which is incorporated herein by reference.

Lower eukaryotes, e.g., yeasts and *Dictyostelium,* may be transformed with IL-10 receptor sequence containing vectors. For purposes of this invention, the most common lower eukaryotic host is the baker's yeast, *Saccharomyces cerevisiae.* It will be used to generically represent lower eukaryotes although a number of other strains and species are also available. Yeast vectors typically consist of a replication origin (unless of the integrating type), a selection gene, a promoter, DNA encoding the receptor or its fragments, and sequences for translation termination, polyadenylation, and transcription termination. Suitable expression vectors for yeast include such constitutive promoters as 3-phosphoglycerate kinase and various other glycolytic enzyme gene promoters or such inducible promoters as the alcohol dehydrogenase 2 promoter or metallothionine promoter. Suitable vectors include derivatives of the following types: self-replicating low copy number (such as the YRp-series), self-replicating high copy number (such as the YEp-series); integrating types (such as the YIp-series), or mini-chromosomes (such as the YCp-series).

Higher eukaryotic cells grown in tissue culture are often the preferred host cells for expression of the functionally active IL-10 receptor protein. In principle, any higher eukaryotic tissue culture cell line is workable, e.g., insect baculovirus expression systems, whether from an invertebrate or vertebrate source. However, mammalian cells are often preferred. Transformation or transfection and propagation of such cells has become a routine procedure. Examples of useful cell lines include HeLa cells, Chinese hamster ovary (CHO) cell lines, baby rat kidney (BRK) cell lines, insect cell lines, bird cell lines, and monkey (COS) cell lines. Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as from adenovirus, SV40, parvoviruses, vaccinia virus, or cytomegalovirus. Representative examples of suitable expression vectors include pCDNA1 (Invitrogen, San Diego, Calif.); pCD, see Okayama, et al. (1985) *Mol. Cell Biol.* 5:1136–1142; pMC1neo Poly-A, see Thomas, et al. (1987) *Cell* 51:503–512; and a baculovirus vector such as pAC 373 or pAC 610, see e.g., O'Reilly, et al. (1992) *Baculovirus Expression Vectors: A Laboratory Manual* Freeman & Co., N.Y.

It will often be desired to express a receptor polypeptide in a system which provides a specific or defined glycosylation pattern. In this case, the usual pattern will be that provided naturally by the expression system. However, the pattern will be modifiable by exposing the polypeptide, e.g., an unglycosylated form, to appropriate glycosylating proteins introduced into a heterologous expression system. For example, the receptor gene may be co-transformed with one or more genes encoding mammalian or other glycosylating enzymes. Using this approach, certain mammalian glycosylation patterns will be achievable in prokaryote or other cells.

V. Receptor Isolation

The described nucleic acids will provide useful source materials possessing high levels of receptor proteins. Cells expressing these proteins can be sources for protein purification, of the natural receptor forms, or variants thereof. In addition, purification segments can be fused to appropriate portions of the receptor to assist in isolation and production. For example, the FLAG sequence, or a functional equivalent, can be fused to the protein via a protease-removable sequence, allowing the FLAG sequence to be recognized by an affinity reagent, and the purified protein subjected to protease digestion to remove the extension. Many other equivalent segments exist, e.g., poly-histidine segments possessing affinity for heavy metal column reagents. See, e.g., Hochuli (1989) *Chemische Industrie* 12:69–70; Hochuli (1990) "Purification of Recombinant Proteins with Metal Chelate Adsorbent" in Setlow (ed.) *Genetic Engineering, Principle and Methods* 12:87–98, Plenum Press, N.Y.; and Crowe, et al. (1992) *OIAexpress: The High Level Expression & Protein Purification System* QUIAGEN, Inc. Chatsworth, Calif.; which are incorporated herein by reference.

Moreover, appropriate host cells may be used to express the receptor proteins at high levels and under physiological conditions which may allow for desirable post-translational processing, e.g., glycosylation variants.

Having produced high level expression sources, standard protein purification techniques are applied to purify the IL-10 receptor components to near homogeneity. These will include such methods as ammonium sulfate precipitation, column chromatography, electrophoresis, centrifugation, crystallization, and others. See, e.g., Ausubel, et al. (1987 and periodic supplements) *Current Protocols in Molecular Biology;* Deutscher (1990) "Guide to Protein Purification" in *Methods in Enzymology* vol 182, and other volumes in this series; and manufacturers' literature on use of protein purification products, e.g., Pharmacia, Piscataway, N.J., or Bio-Rad, Richmond, Calif.; which are incorporated herein by reference.

VI. Receptor Analogs

"Derivatives" of the IL-10 receptor include amino acid sequence mutants, glycosylation variants, and covalent or aggregative conjugates with other chemical moieties. Covalent derivatives can be prepared by linkage of functionalities to groups which are found in the IL-10 receptor amino acid side chains or at the N- or C- termini, by means which are well known in the art. These derivatives can include, without limitation, aliphatic esters or amides of the carboxyl terminus, or of residues containing carboxyl side chains, O-acyl derivatives of hydroxyl group-containing residues, and N-acyl derivatives of the amino terminal amino acid or amino-group containing residues, e.g., lysine or arginine. Acyl groups are selected from the group of alkyl-moieties including C3 to C18 normal alkyl, thereby forming alkanoyl aroyl species.

In particular, glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells which normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine.

A major group of derivatives are covalent conjugates of the IL-10 receptor or fragments thereof with other proteins or polypeptides. These derivatives can be synthesized in recombinant culture such as N- or C-terminal fusions or by the use of agents known in the art for their utility in crosslinking proteins through reactive side groups. Preferred IL-10 derivatization sites with cross-linking agents are at free amino groups, carbohydrate moieties, and cysteine residues.

Fusion polypeptides between the receptors and other homologous or heterologous proteins are also provided. Homologous polypeptides may be fusions between different growth factor or cytokine receptors, resulting in, for instance, a hybrid protein exhibiting ligand specificity of one receptor and the intracellular region of another, or a receptor which may have broadened or weakened specificity of binding. Likewise, heterologous fusions may be constructed which would exhibit a combination of properties or activities of the derivative proteins. Typical examples are fusions of a reporter polypeptide, e.g., luciferase, with a segment or domain of a receptor, e.g., a ligand-binding segment, so that the presence or location of a desired ligand may be easily determined. See, e.g., Dull, et al., U.S. Pat. No. 4,859,609, which is hereby incorporated herein by reference. Other gene fusion partners include bacterial β-galactosidase, trpE, Protein A, β-lactamase, alpha amylase, alcohol dehydrogenase, and yeast alpha mating factor. See, e.g., Godowski, et al. (1988) *Science* 241:812–816.

The phosphoramidite method described by Beaucage and Caruthers (1981) *Tetra. Letts.* 22:1859–1862, will produce suitable synthetic DNA fragments. A double stranded fragment will often be obtained either by synthesizing the complementary strand and annealing the strand together under appropriate conditions or by adding the complementary strand using DNA polymerase with an appropriate primer sequence.

Such polypeptides may also have amino acid residues which have been chemically modified by phosphorylation, sulfonation, biotinylation, or the addition or removal of other moieties, particularly those which have molecular shapes similar to phosphate groups. In some embodiments, the modifications will be useful labeling reagents, or serve as purification targets, e.g., affinity ligands.

Fusion proteins will typically be made by either recombinant nucleic acid methods or by synthetic polypeptide methods. Techniques for nucleic acid manipulation and expression are described generally, for example, in Sambrook, et al. (1989) *Molecular Cloning: A Laboratory Manual* (2d ed.), Vols. 1–3, Cold Spring Harbor Laboratory, which are incorporated herein by reference. Techniques for synthesis of polypeptides are described, for example, in Merrifield (1963) *J. Amer. Chem. Soc.* 85:2149–2156; Merrifield (1986) *Science* 232: 341–347; and Atherton, et al. (1989) *Solid Phase Peptide Synthesis: A Practical Approach*, IRL Press, Oxford; each of which is incorporated herein by reference.

This invention also contemplates the use of derivatives of the IL-10 receptor other than variations in amino acid sequence or glycosylation. Such derivatives may involve covalent or aggregative association with chemical moieties. These derivatives generally fall into three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of IL-10 or other binding ligands. For example, the IL-10 receptor can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of anti-IL-10 receptor antibodies or IL-10. The IL-10 receptor can also be labeled with a detectable group, for example radioiodinated by the chloramine T procedure, covalently bound to rare earth chelates, or conjugated to another fluorescent moiety for use in diagnostic assays.

The solubilized IL-10 receptor of this invention can be used as an immunogen for the production of antisera or antibodies specific for the receptor or any fragments thereof. The purified receptor can be used to screen monoclonal antibodies or antigen-binding fragments prepared by immunization with various forms of impure preparations containing the IL-10 receptor. In particular, the term "antibodies" also encompasses antigen binding fragments of natural antibodies. The purified receptor can also be used as a reagent to detect any antibodies generated in response to the presence of elevated levels of IL-10 receptor or cell fragments containing the IL-10 receptor. Additionally, IL-10 receptor fragments may also serve as immunogens to produce the antibodies of the present invention, as described immediately below. For example, this invention contemplates antibodies having binding affinity to or being raised against the amino acid sequence shown in Table 2, or fragments thereof. In particular, this invention contemplates antibodies having binding affinity to or being raised against specific fragments which are predicted to lie outside of the lipid bilayer. These fragments should become readily apparent upon completion of the sequence of the human or mouse receptors. In addition, this invention covers fragments of the IL-10 receptor which are predicted to reside on the extracellular side of the membrane. Analysis of protein structure to identify membrane associated regions is described, e.g., in von Heijne (1992) *J. Mol. Biol.* 225:487–494; and Fasman, et al. (1990) *Trends in Biochemical Sciences* 15:89–92.

VII. Antibodies

Antibodies can be raised to the various species variants of these receptor components, and fragments thereof, both in their naturally occurring forms and in their recombinant forms. Additionally, antibodies can be raised to IL-10 receptors in either their active forms or in their inactive forms, the difference being that antibodies to the active receptor are more likely to recognize epitopes which are only present in the active receptor. Anti-idiotypic antibodies are also contemplated.

Antibodies, including binding fragments and single chain versions, against predetermined fragments of the IL-10 receptor can be raised by immunization of animals with conjugates of the fragments with immunogenic proteins. Monoclonal antibodies are prepared from cells secreting the desired antibody. These antibodies can be screened for binding to normal or defective IL-10 receptors, or screened for agonistic or antagonistic IL-10 receptor activity. These monoclonal antibodies will normally bind with at least a Kd of about 1 mM, more normally at least 300 $\mu$M, generally at least 100 $\mu$M, more generally at least 30 $\mu$M, ordinarily at least 10 μM, more ordinarily at least 3 μM, often at least 1 μM, more often at least 300 nM, typically at least 100 nM, more typically at least 30 nM, usually at least 10 nM, more usually at least 3 nM, preferably at least 1 nM, more preferably at least 300 pM, and in especially preferred embodiments at least 100 to 10 pM or better. Antibodies will be raised against species or other variants of these receptor components.

The antibodies, including antigen binding fragments, of this invention can have significant diagnostic or therapeutic value. They can be potent antagonists that bind to the IL-10 receptor and inhibit ligand binding to the receptor or inhibit the ability of an IL-10-like peptide to elicit a biological response. They also can be useful as non-neutralizing antibodies and can be coupled to toxins or radionuclides so that when the antibody binds to the receptor, the cell itself is killed. Further, these antibodies can be conjugated to drugs or other therapeutic agents, either directly or indirectly by means of a linker.

The antibodies of this invention can also be useful in diagnostic applications. As capture or non-neutralizing antibodies, they can bind to the IL-10 receptor without inhibiting ligand binding. As neutralizing antibodies, they can be useful in competitive binding assays. They will also be useful in detecting or quantifying IL-10 or IL-10 receptors.

Receptor fragments may be joined to other materials, particularly polypeptides, as fused or covalently joined polypeptides to be used as immunogens. The IL-10 receptor and its fragments may be fused or covalently linked to a variety of immunogens, such as keyhole limpet hemocyanin, bovine serum albumin, tetanus toxoid, etc. For descriptions of methods of preparing polyclonal antisera, see *Microbiology,* Hoeber Medical Division, Harper and Row, 1969; Landsteiner (1962) *Specificity of Serological Reactions,* Dover Publications, New York, and Williams, et al. (1967) *Methods in Immunology and Immunochemistry,* Vol. 1, Academic Press, New York, each of which is incorporated herein by reference. A typical method involves hyperimmunization of an animal with an antigen. Blood from the animal is then collected shortly after repeated immunizations and gamma globulin is isolated.

In some instances, it is desirable to prepare monoclonal antibodies from various mammalian hosts, such as mice, rodents, cows, sheep, goats, donkeys, primates, humans, etc. Description of techniques for preparing such monoclonal antibodies may be found in, e.g., Stites, et al. (eds.) *Basic and Clinical Immunology* (4th ed.), Lange Medical Publications, Los Altos, Calif., and references cited therein; Harlow and Lane (1988) *Antibodies: A Laboratory Manual,* CSH Press; Goding (1986) *Monoclonal Antibodies: Principles and Practice* (2d ed.) Academic Press, New York; and particularly in Kohler and Milstein (1975) in *Nature* 256: 495–497, which discusses one method of generating monoclonal antibodies. Each of these references is incorporated herein by reference. Summarized briefly, this method involves injecting an animal with an immunogen. The animal is then sacrificed and cells taken from its spleen, which are then fused with myeloma cells. The result is a hybrid cell or "hybridoma" that is capable of reproducing in vitro. The population of hybridomas is then screened to isolate individual clones, each of which secretes a single antibody species to the immunogen. In this manner, the individual antibody species obtained are the products of immortalized and cloned single B cells from the immune animal generated in response to a specific site recognized on the immunogenic substance.

Other suitable techniques involve in vitro exposure of lymphocytes to the antigenic polypeptides or alternatively to selection of libraries of antibodies in phage or similar vectors. See, Huse, et al. (1989) "Generation of a Large Combinatorial Library of the Immunoglobulin Repertoire in Phage Lambda," *Science* 246:1275–1281; and Ward, et al. (1989) *Nature* 341:544–546, each of which is hereby incorporated herein by reference. The polypeptides and antibodies of the present invention may be used with or without modification, including chimeric or humanized antibodies. Frequently, the polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent moieties, chemiluminescent moieties, magnetic particles, and the like. Patents, teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced, see Cabilly, U.S. Pat. No. 4,816,567. These patents are incorporated herein by reference.

The antibodies of this invention can also be used for affinity chromatography in isolating the receptor. Columns can be prepared where the antibodies are linked to a solid support, e.g., particles, such as agarose, Sephadex, or the like, where a cell lysate may be passed through the column, the column washed, followed by increasing concentrations of a mild denaturant, whereby the purified receptor protein will be released.

The antibodies may also be used to screen expression libraries for particular expression products. Usually the antibodies used in such a procedure will be labeled with a moiety allowing easy detection of presence of antigen by antibody binding.

Antibodies raised against each receptor will also be used to raise anti-idiotypic antibodies. These will be useful in detecting or diagnosing various immunological conditions related to expression of the respective receptors.

VIII. Other Uses of Receptors

Soluble receptor fragments will also find use as carriers for IL-10, e.g., to protect the cytokine from various degradative or other activities. The complex may be useful in certain situations as a slow release composition, allowing slow functional release of the cytokine or antagonist. Moreover, as an antagonist of IL-10, soluble forms of the receptor, e.g., a fragment containing the cytokine binding portions without membrane associated segments, will be useful diagnostic or therapeutic compositions. As a diagnostic reagent, such fragment may be used as a substitute for antibodies against IL-10, but will likely be equivalent to a neutralizing antibody.

In addition, it is likely that the isolated component described herein is analogous to α subunits of other cytokine receptors. This suggests that a unique β component for the IL-10 receptor may exist, and could, in association with these components, modulate the activity from IL-10 binding. This will provide a convenient means to isolate this putative β subunit. See, e.g., Hayashida, et al. (1990) *Proc. Nat'l Acad. Sci. USA* 87:9655–9659. Alternatively, species or tissue specific accessory molecules, e.g., proteins, may provide a context for modification of the receptor protein properties or activities.

Both the naturally occurring and the recombinant form of the IL-10 receptor components of this invention are particularly useful in kits and assay methods which are capable of screening compounds for binding activity to the receptors. Several methods of automating assays have been developed in recent years so as to permit screening of tens of thousands of compounds per year. See, e.g., Fodor, et al. (1991) *Science* 251:767–773, which is incorporated herein by reference and which describes means for testing of binding affinity by a plurality of defined polymers synthesized on a solid substrate. Phage or other libraries of various random polypeptide sequences would also be useful. The development of suitable assays can be greatly facilitated by the availability of large amounts of purified, soluble receptor such as is provided by this invention.

For example, antagonists can normally be found once the receptor has been characterized. Testing of potential receptor antagonists is now possible upon the development of highly automated assay methods using a purified receptor. In particular, new agonists and antagonists will be discovered using screening techniques made available by the reagents provided herein.

This invention is particularly useful for screening compounds by using the recombinant receptors in any of a variety of drug screening techniques. The advantages. of using a recombinant receptor in screening for receptor reactive drugs include: (a) improved renewable source of the receptor from a specific source; (b) potentially greater number of receptors per cell giving better signal-to-noise ratio in assays; and (c) species variant specificity (theoretically giving greater biological and disease specificity).

One method of drug screening utilizes eukaryotic or prokaryotic host cells which are stably transformed with recombinant DNA molecules expressing the receptor. Cells may be isolated which express a receptor in isolation from any others. Such cells, either in viable or fixed form, can be used for standard receptor/ligand binding assays. See also, Parce, et al. (1989) *Science* 246:243–247; and Owicki, et al. (1990) *Proc. Nat'l Acad. Sci. USA* 87:4007–4011, which are incorporated herein by reference and describe sensitive methods to detect cellular responses. Competitive assays are particularly useful, where the cells (a source of IL-10 receptor) are contacted and incubated with a labeled ligand having known binding affinity to the receptor, such as $^{125}$I-IL-10, and a test compound whose binding affinity to the IL-10 receptor is being measured. The bound ligand and free ligand are then separated to assess the degree of ligand binding. The amount of test compound bound is inversely proportional to the amount of labeled ligand binding measured. Any one of numerous techniques can be used to separate bound from free ligand to assess the degree of ligand binding. This separation step could typically involve a procedure such as adhesion to filters followed by washing, adhesion to plastic followed by washing, or centrifugation of the cell membranes. Viable cells could also be used to screen for the effects of drugs on IL-10 receptor mediated functions, e.g., second messenger levels, i.e., $Ca^{++}$; cell proliferation; inositol phosphate pool changes; levels of phosphorylation; nitrous oxide levels; and others. Some detection methods allow for elimination of a separation step, e.g., a proximity sensitive detection system. Calcium sensitive dyes will be useful for detecting $Ca^{++}$ levels, with a fluorimeter or a fluorescence cell sorting apparatus. See also, Lowenstein, et al. (1992) *Cell* 70:705–707.

Another method utilizes membranes from transformed eukaryotic or prokaryotic host cells as the source of the IL-10 receptor. These cells are stably transformed with DNA vectors directing the expression of the IL-10 receptor. Essentially, the membranes would be prepared from the cells and used in an appropriate receptor/ligand binding assay, e.g., the competitive assay set forth above.

Still another approach is to use solubilized, unpurified or solubilized, purified receptors from transformed eukaryotic or prokaryotic host cells. This allows for a "molecular" binding assay with the advantages of increased specificity, the ability to automate, and high drug test throughput.

Another technique for drug screening involves an approach which provides high throughput screening for compounds having suitable binding affinity to the IL-10 receptor and is described in detail in Geysen, European Patent Application 84/03564, published on Sep. 13, 1984, which is incorporated herein by reference. First, large numbers of different small peptide test compounds are synthesized on a solid substrate, e.g., plastic pins or some other appropriate surface, see Fodor, et al. (1991). Then all the pins are reacted with solubilized, unpurified or solubilized, purified IL-10 receptor, and washed. The next step involves detecting bound IL-10 receptor.

Rational drug design may also be based upon structural studies of the molecular shapes of the receptor and other effectors or ligands. Effectors may be other proteins which mediate other functions in response to ligand binding, or other proteins which normally interact with the receptor. One means for determining which sites interact with specific other proteins is a physical structure determination, e.g., x-ray crystallography or NMR techniques (2 or 3 dimensional). These will provide guidance as to which amino acid residues form molecular contact regions. For a detailed description of protein structural determination, see, e.g., Blundell and Johnson (1976) *Protein Crystalloaraphy*, Academic Press, New York, which is hereby incorporated herein by reference.

Purified receptor can be coated directly onto plates for use in the aforementioned drug screening techniques. However, non-neutralizing antibodies to these receptors can be used as capture antibodies to immobilize the respective receptor on the solid phase.

IX. Ligands: Agonists and Antagonists

The blocking of physiological response to IL-10-like peptides may result from the inhibition of binding of the ligand to the receptor, likely through competitive inhibition. Thus, in vitro assays of the present invention will often use isolated membranes from cells expressing a recombinant receptor, soluble fragments comprising the ligand binding segments of these receptors, or fragments attached to solid phase substrates. These assays will also allow for the diagnostic determination of the effects of either binding segment mutations and modifications, or ligand mutations and modifications, e.g., ligand analogs.

This invention also contemplates the use of competitive drug screening assays, e.g., where neutralizing antibodies to the receptor or receptor fragments compete with a test compound for binding to the receptor. In this manner, the antibodies can be used to detect the presence of any polypeptide which shares one or more binding sites of the receptor and can also be used to occupy binding sites on the receptor that might otherwise be occupied. by IL-10.

Additionally, neutralizing antibodies against the receptor and soluble fragments of the receptor which contain the ligand binding site can be used to inhibit IL-10 receptor function in, e.g., macrophages, B cells, T cells, or related cell types.

X. Kits

This invention also contemplates use of the IL-10 receptor, fragments thereof, peptides, and their fusion products in a variety of diagnostic kits and methods for detecting the presence of the IL-10 receptor. Typically the kit will have a compartment containing either a defined receptor peptide or gene segment or a reagent which recognizes one or the other.

A kit for determining the binding affinity of a test compound to IL-10 receptor would typically comprise a test compound; a labeled compound, for example a ligand or antibody having known binding affinity for IL-10 receptor; a source of IL-10 receptor (naturally occurring or recombinant); and a means for separating bound from free labeled compound, such as a solid phase for immobilizing IL-10 receptor. Once compounds are screened, those having suitable binding affinity to the IL-10 receptor can be evaluated in suitable biological assays, as are well known in the art, to determine whether they act as agonists or antagonists. The availability of recombinant receptor polypeptides also provide well defined standards for calibrating such assays.

A preferred kit for determining the concentration of, for example, IL-10 receptor in a sample would typically comprise a labeled compound, e.g., ligand or antibody, having known binding affinity for the receptor, a source of IL-10 receptor (naturally occurring or recombinant) and a means for separating the bound from free labeled compound, for example a solid phase for immobilizing the IL-10 receptor. Compartments containing reagents, and instructions, will normally be provided.

One method for determining the concentration of IL-10 receptor in a sample would typically comprise the steps of: (1) preparing membranes from a sample comprised of a IL-10 receptor source; (2) washing the membranes and suspending them in a buffer; (3) solubilizing the IL-10 receptor by incubating the membranes in a culture medium to which appropriate detergents have been added; (4) adjusting the detergent concentration of the solubilized receptor; (5) contacting and incubating said dilution with radiolabeled IL-10 to form IL-10:IL-10 receptor complexes; (6) recovering the complexes such as by filtration through polyethyleneimine treated filters; and (7) measuring the radioactivity of the recovered complexes.

Antibodies, including antigen binding fragments, specific for the receptor or receptor fragments are useful in diagnostic applications to detect the presence of elevated levels of the receptor and/or its fragments. Such diagnostic assays can employ lysates, live cells, fixed cells, immunofluorescence, cell cultures, body fluids, and further can involve the detection of antigens related to the IL-10 receptor in serum, or the like. Diagnostic assays may be homogeneous (without a separation step between free reagent and receptor-ligand complex) or heterogeneous (with a separation step). Various commercial assays exist, such as radioimmunoassay (RIA), enzyme-linked immunosorbent assay (ELISA), enzyme immunoassay (EIA), enzyme-multiplied immunoassay technique (EMIT), substrate-labeled fluorescent immunoassay (SLFIA) and the like. For example, unlabeled antibodies can be employed by using a second antibody which is labeled and which recognizes the antibody to the IL-10 receptor or to a particular fragment thereof. These assays have also been extensively discussed in the literature. See, e.g., Harlow and Lane (1988) *Antibodies: A Laboratory Manual,* CSH.

Anti-idiotypic antibodies may have similar use to diagnose presence of antibodies against a receptor, as such may be diagnostic of various abnormal states. For example, over- or inappropriate production of IL-10 receptor may result in various immunological reactions which may be diagnostic of abnormal receptor expression, particularly in proliferative cell conditions such as cancer.

Frequently, the reagents for diagnostic assays are supplied in kits, so as to optimize the sensitivity of the assay. For the subject invention, depending upon the nature of the assay, the protocol, and the label, either labeled or unlabeled antibody, or labeled receptor is provided. This is usually in conjunction with other additives, such as buffers, stabilizers, materials necessary for signal production such as substrates for enzymes, and the like. Preferably, the kit will also contain instructions for proper use and disposal of the contents after use. Typically the kit has compartments for each useful reagent. Desirably, the reagents are provided as a dry lyophilized powder, where the reagents may be reconstituted in an aqueous medium having appropriate concentrations for performing the assay.

Any of the aforementioned constituents of the drug screening and the diagnostic assays may be used without modification or may be modified in a variety of ways. For example, labeling may be achieved by covalently or non-covalently joining a moiety which directly or indirectly provides a detectable signal. In any of these assays, the ligand, test compound, IL-10 receptor, or antibodies thereto can be labeled either directly or indirectly. Possibilities for direct labeling include label groups: radiolabels such as $^{125}$I, enzymes (U.S. Pat. No. 3,645,090) such as peroxidase and alkaline phosphatase, and fluorescent labels (U.S. Pat. No. 3,940,475) capable of monitoring the change in fluorescence intensity, wavelength shift, or fluorescence polarization. Both of the patents are incorporated herein by reference. Possibilities for indirect labeling include biotinylation of one constituent followed by binding to avidin coupled to one of the above label groups.

There are also numerous methods of separating the bound from the free ligand, or alternatively the bound from the free test compound. The receptor can be immobilized on various matrices followed by washing. Suitable matrices include plastic such as an ELISA plate, filters, and beads. Methods of immobilizing the receptor to a matrix include, without limitation, direct adhesion to plastic, use of a capture antibody, chemical coupling, and biotin-avidin. The last step in this approach involves the precipitation of receptor/ligand complex by any of several methods including those utilizing, e.g., an organic solvent such as polyethylene glycol or a salt such as ammonium sulfate. Other suitable separation techniques include, without limitation, the fluorescein antibody magnetizable particle method described in Rattle, et al. (1984) *Clin. Chem.* 30(9):1457–1461, and the double antibody magnetic particle separation as described in U.S. Pat. No. 4,659,678, each of which is incorporated herein by reference.

The methods for linking protein receptors or their fragments to the various labels have been extensively reported in the literature and do not require detailed discussion here. Many of the techniques involve the use of activated carboxyl groups either through the use of carbodiimide or active esters to form peptide bonds, the formation of thioethers by reaction of a mercapto group with an activated halogen such as chloroacetyl, or an activated olefin such as maleimide, for linkage, or the like. Fusion proteins will also find use in these applications.

Another diagnostic aspect of this invention involves use of oligonucleotide or polynucleotide sequences taken from the sequence of a receptor for IL-10. These sequences can be used as probes for detecting abnormal levels of the receptor in defined cells of patients suspected of having, e.g., an autoimmune condition, inability to properly respond to infections or inflammation, or a proliferative cell condition like cancer. The preparation of both RNA and DNA nucleotide sequences, the labeling of the sequences, and the preferred size of the sequences has received ample description and discussion in the literature. Normally an oligonucleotide probe should have at least about 14 nucleotides, usually at least about 18 nucleotides, and the polynucleotide probes may be up to several kilobases. Various labels may be employed, most commonly radionuclides, particularly $^{32}$P. However, other techniques may also be employed, such as using photoreactive or biotin modified nucleotides for introduction into a polynucleotide. The biotin then serves as the site for binding to avidin or antibodies, which may be labeled with a wide variety of labels, such as radionuclides, fluorescers, enzymes, or the like. Alternatively, antibodies may be employed which can recognize specific duplexes, including DNA duplexes, RNA duplexes, DNA-RNA hybrid duplexes, or DNA-protein complexes. The antibodies in turn may be labeled and the assay carried out where the duplex is bound to a surface, so that upon the formation of duplex on the surface, the presence of antibody bound to the duplex can be detected. The use of probes to the novel anti-sense RNA may be carried out in any conventional techniques such as nucleic acid hybridization, plus and minus screening, recombinational probing, hybrid released translation (HRT), and hybrid arrested translation (HART). This also includes amplification techniques such as polymerase chain reaction (PCR).

Diagnostic kits which also test for the qualitative or quantitative presence of other markers are also contemplated. Diagnosis or prognosis may depend on the combination of multiple indications used as markers. Thus, kits may test for combinations of markers. See, e.g., Viallet, et al. (1989) *Progress in Growth Factor Res.* 1:89–97.

XI. Therapeutic Applications

This invention provides reagents with significant therapeutic value. The IL-10 receptor (naturally occurring or recombinant), fragments thereof and antibodies thereto, along with compounds identified as having binding affinity to the IL10 receptor, should be useful in the treatment of various conditions, e.g., autoimmune conditions, septic and toxic shock conditions, and infectious conditions. See, e.g., Hsu et al (1992) *Intn'l Immunol.* 4:563–569; de Waal Malefyt, et al. (1991) *J. Expt'l Med.* 174:1209–1220; Fiorentino, et al. (1991) *J. Immunol.* 147:3815–3822; and Ishida, et al. (1992) *J. Expt'l Med.* 175:1213–1220. Additionally, this invention should have therapeutic value in any disease or disorder associated with abnormal expression or abnormal triggering of receptors for IL10. For example, it is believed that the IL-10 receptor likely plays a role in many basic regulatory processes in immune function. Agonists and antagonists of the cytokine will be developed using the present invention. See also, e.g., Harada, et al. (1992) *J. Biol. Chem.* 267:22752–22758, which identifies receptor segments which are useful in antagonizing receptor function.

Recombinant IL-10 receptor, including soluble fragments thereof, or IL-10 receptor antibodies can be purified and then administered to a patient. These reagents can be combined for therapeutic use with additional active ingredients, e.g., in conventional pharmaceutically acceptable carriers or diluents, along with physiologically innocuous stabilizers and excipients. These combinations can be sterile filtered and placed into dosage forms as by lyophilization in dosage vials or storage in stabilized aqueous preparations. This invention also contemplates use of antibodies or binding fragments thereof, e.g., which are soluble, which are not complement-binding.

Drug screening using the IL-10 receptor or fragments thereof can be performed to identify compounds having binding affinity to the IL-10 receptor. Subsequent biological assays can then be utilized to determine if the compound has intrinsic stimulating activity and is therefore a blocker or antagonist in that it blocks the activity of IL-10. Likewise, a compound having intrinsic stimulating activity can activate the receptor and is thus an agonist in that it simulates the activity of IL-10. This invention further contemplates the therapeutic use of antibodies to the IL-10 receptor as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; each of which is hereby incorporated herein by reference. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index,* Merck & Co., Rahway, N.J. Because of the high affinity binding between IL-10 and its receptors, low dosages of these reagents would be initially expected to be effective. Thus, dosage ranges would ordinarily be expected to be in amounts lower than 1 mM concentrations, typically less than about 10 $\mu$M concentrations, usually less than about 100 nM, preferably less than about 10 pM (picomolar), and most preferably less than about 100 fM (femtomolar), with an appropriate carrier. Slow release formulations, or slow release apparatus will often be utilized for continuous administration. The intracellular segments of the receptors, both the IL-10 receptor and related receptors will find additional uses as described in detail below.

The IL-10 receptor, fragments thereof, and antibodies to the receptor or its fragments, antagonists, and agonists, may be administered directly to the host to be treated or, depending on the size of the compounds, it may be desirable to conjugate them to carrier proteins such as ovalbumin or serum albumin prior to their administration. Therapeutic formulations may be administered in any conventional dosage formulation. While it is possible for the active ingredient to be administered alone, it is preferable to present it as a pharmaceutical formulation. Formulations comprise at least one active ingredient, as defined above, together with one or more acceptable carriers thereof. Each carrier must be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics,* 8th Ed., Pergamon Press; and *Remington's Pharmaceutical Sciences,* 17th ed. (1990), Mack Publishing Co., Easton, Pa.; each of which is hereby incorporated herein by reference. The therapy of this invention may be combined with or used in association with other chemotherapeutic or chemopreventive agents.

XII. Additional Receptor Subunits

It is quite likely that additional subunits of the IL-10 receptor exist. IL-10 exhibits different specific activities (units per mg of protein) in different biological assays. For example, the specific activity of IL-10 in cytokine synthesis inhibitory factor assays, where IL-10 acts on macrophages, is higher than that observed in costimulation of mouse thymocyte or mouse mast cell proliferation. See Table 3.

TABLE 3

Activities of recombinant mouse of human IL-10, in units/ml.

| | | CSIF ASSAYS | |
|---|---|---|---|
| Sample | IFN-γ | $^3$H cpm | thymocyte $^3$H cpm |
| mouse IL-10 | | | |
| E. coli (~0.2 mg/ml) | $10^6$ | $2 \times 10^6$ | $\sim 2 \times 10^5$ |
| Baculovirus (~5 μg/ml) | $5 \times 10^4$ | $6 \times 10^4$ | 6000 |
| COS7 (~0.6 μg/ml) | 9000 | 9000 | ~500 |
| human IL-10 | | | |
| COS7 (~0.15 μg/ml) | 1400 | 1100 | ~90 |
| CHO (~1 mg/ml) | $10^7$ | $10^7$ | $\sim 8 \times 10^5$ |

The human and mouse IL-10 receptors provided herein bind IL-10 on their own. However, the ability of each component by itself to bind vIL-10 has not yet been demonstrated. In addition, the apparent Kd of the recombinant IL-10 receptor (100–400 pM) is considerably higher than the $EC_{50}$ of IL-10 on macrophages and monocytes (5–20 pM). By analogy to related class 2 cytokine receptors, e.g., IFN-α, IFN-β, or IFN-γ, whose structural motifs are similar, an accessory molecule might be required for signal transduction upon IL-10 binding.

If so, various approaches would be useful for screening for accessory components. These approaches include both physical affinity methods, and activity screening. Similar affinity methods as used herein with human IL-10 can be used with vIL-10. See, e.g., Table 1. Since binding of these components to vIL10, which has activity, has not been demonstrated some modified form of the receptor would be expected to exist. A FLAG-vIL-10 fusion construct should be useful in selective purification of cells containing such a receptor form.

One approach is to transfect libraries made from appropriate cells, e.g., cells capable of responding to vIL-10, to screen transfected cells which otherwise are non-responsive to v-IL-10; or fail to bind to vIL-10 (or the FLAG-vIL-10 fusion). Such a library of transfected cells could be screened using a FLAG-vIL-10 marker at a concentration too low to bind effectively to a receptor component described in Table 2. See, e.g., Kitamura, et al. (1991) Cell 66:1165–1174; and Hara, et al. (1992) 11:1875–1884. Alternatively, a FLAG-vIL-10 fusion construct can be used for panning or FACS separation, e.g., as described in Table 1 and Example 4. These techniques may be combined with co-transfection with the IL-10 component already isolated, e.g., to isolate accessory components which modify the binding properties. Components which increase ligand binding affinity upon association are particularly desired. cDNA clones isolated in this manner are characterized, e.g., by sequencing, and compared structurally to other subunits or accessory proteins identified in other receptors.

The broad scope of this invention is best understood with reference to the following examples, which are not intended to limit the inventions to specific embodiments.

EXPERIMENTAL

The following experimental results show that high specific activity iodinated hIL-10 can be enzymatically prepared and that this labeled ligand can bind in a specific and saturable manner to its receptor in several mouse and human cell lines. MC/9 proliferation assays showed that this labeled protein retains greater than 50% biological activity. Molecular weight sizing of the purified, iodinated protein indicated that the protein exists predominantly as a dimer and in this form is capable of binding specifically to its receptor. A 37 kDa dimer of human IL-10, when examined under reducing conditions, may be dissociated by detergents to a single 18 kDa species. This is consistent with the 37 kDa species representing a non-covalently linked dimer of the cytokine. Moreover, this suggests that active hIL-10 is a non-covalently linked dimer.

Screening for specific binding with several cell lines of mouse and human origin indicates that murine mast cell line MC/9 and human B lymphoma line JY have the highest number of accessible, e.g., unoccupied, receptors per cell. Human B cell lines Ramos and BH5, as well as erythroleukemia line TF-1, bind at a reduced level relative to MC/9 and JY, followed by human T-cell and macrophage lines. These cell lines were chosen based on the reported observations that mast cells, macrophage/monocytes, B cells, and T cells respond to IL-10. The TF-1 cell line, originally derived from an erythroleukemic patient, is dependent on IL-3, erythropoietin, or GM-CSF for long term growth. The cell line is also responsive to IL-4, IL-5 and IL-6 in proliferation assays. Despite the responsiveness of the TF-1 cell line to a variety of cytokines, no proliferative effects on TF-1 cells in response to hIL-10 either alone or in combination with other cytokines could be detected.

The Kd values obtained from Scatchard analysis indicate that hIL-10 binds with relatively high affinity to its receptor on both mouse and human cells, and that the receptor is present at the numbers between 100 and 300 unoccupied receptors per cell. Competition binding assays with human and murine IL-10 on the mouse mast cell line MC/9 and the human cell line JY demonstrated that while the mouse ligand is able to compete with binding of iodinated hIL-10 to the mouse cell line, it cannot do so with the human cell line. One explanation is that under the binding conditions employed, hIL-10 can recognize and bind to both the mouse and the human receptor, while the mouse IL-10 can only recognize the mouse receptor. Supporting this notion of species-specificity of the mouse ligand in binding site-recognition is the absence of any significant biological cross-reactivity of murine IL-10 on human cells.

Chemical cross-linking of radiolabeled hIL-10 to JY and MC/9 cells yielded a similar pattern of complexes. The intensities of observable signals were very weak even after a long exposure. In MC/9, two major and a few minor bands were detected, representing hIL-10 specific binding complexes. The apparent Mr of the minor bands was estimated to be about 110–180 kDa and the two more visible bands were estimated to be about 98 kDa and 83 kDa, respectively. The 98 kDa and 83 kDa bands were also observed with JY cells although the signals were relatively weaker. The presence of these common bands indicated that the molecular sizes of the observed human and mouse IL-10 receptors are similar. The approximated size difference between the 117 kDa and the 98 kDa complex, i.e., 19 kDa, is consistent with the molecular weight of an hIL-10 monomer. One explanation of the these observations is that the 117 kDa band might represent receptor/hIL-10 dimer complex and the 98 kDa might represent a dissociation product. However, there are other explanations such as differential glycosylation of the receptor(s), multimeric receptor(s), or protein degradation of ligand-receptor complexes.

Upon reevaluation of the molecular weight standards, the major bands have been assigned molecular weights in the range of 90–110 kD.

Several cytokines and growth factors, for example, G-CSF and IL-5, possess both high and low affinity binding sites on cell lines. Under the conditions used to examine the binding of human IL-10 to cells, it has not been possible to detect more than one class of binding site with the JY and MC/9 cell lines. There is a possibility of low affinity binding sites on these cell lines which are not detectable under the binding and washing regimen employed, or the presence of low affinity binding sites on other cell lines not included in this study. There is also a possibility of higher affinity binding sites present in numbers too small to be detected.

EXAMPLE 1: General Methods

Cell Lines and tissue culture.

MC/9 cells (ATCC# CRL1649) were routinely grown in Dulbecco's modified essential medium (DMEM) with 10% fetal bovine serum containing 3–5% mitogen-stimulated spleen-conditioned media, 100 U/ml mIL-4, 10 U/ml Penicillin/Streptomycin, 2 mM glutamine, 1 mM sodium pyruvate, 1×MEM essential and non-essential amino acids, 1×MEM vitamins, 50 µM β-mercaptoethanol, 6 mg/liter folic acid, 116 mg/liter L-arginine, and 36 mg/liter L-asparagine. TF-1 cells (see Kitamura, et al. (1989) *J. Cell. Physiol.* 140:323–334) were grown in RPMI1640 with 10% FBS and 1 µg/liter mouse GM-CSF. JY cells (provided by J. de Vries, DNAX, Palo Alto, Calif.) were grown in DMEM with 10% FBS, 6 mM glutamine, and antibiotics. The other cell lines [Ramos (ATCC# CRL1596), WEHI 265.1 (TIB204), U937 (CRL1593), HL-60 (CCL240), JD (CRL8163), Jijoye (CCL87), THP-1 (TIB202), B-JAB (provided by J. Banchereau, Schering-Plough France), and BH-5 (provided by W. Tadmori, Schering-Plough Research Institute, SPRI)] were grown in RPMI with 10% FBS, 6 mM glutamine, and antibiotics. In addition, culture media for BH-5 and THP-1 cells were supplemented with 50 µM β-mercaptoethanol. All tissue culture reagents were from GIBCO (Gaithersburg, Md.). Fluorescence activated cell sorting (FACS)

Fluorescent activated cell sorting was performed using standard methods on a Becton-Dickinson FACStar PLUS. See, e.g., Shapiro (1988) *Practical Flow Cytometry* (2d ed.) Alan Liss, New York, which is incorporated herein by reference.

Cytokines and antibodies.

Recombinant CHO-derived human IL-10 and IL-5, as well as *E. coli*-derived human GM-CSF, IFN-γ, and mouse IL-10 were supplied by Schering-Plough Research Institute (SPRI), New Jersey. The specific biological activity of these preparations were $2.3 \times 10^7$ units/mg for hIL-10 and $1.6 \times 10^7$ units/mg for mIL-10 as measured by the MC/9 proliferation assay (see below). Recombinant hIL-6 was purchased from Genzyme (Cambridge, Mass.), though other commercial suppliers include, e.g., PeproTech, Inc., Rocky Hill, N.J. Monoclonal antibodies to IL-10 and IL-5 were provided by J. Abrams (DNAX, Palo Alto, Calif.), see Abrams, et al. (1992) *Immunol. Rev.* 127:5–24.

Iodination of hIL-10.

Purified hIL-10 protein was labeled using the Enzymobead radioiodination reagent (Bio-Rad, Richmond, Calif.), which is an immobilized preparation of lactoperoxidase and glucose oxidase, following the manufacturer's protocols. The purified protein was passed through a PD-10 column (Pharmacia LKB Biotechnology, Piscataway, N.J.) to remove free label. Additional samples were also customiodinated following the lactoperoxidase method (NEN Research Products, Boston, Mass.). Specific radioactivity obtained was in the range of 100–180 µCi/µg hIL-10. The iodinated material was then passed through a 120 ml Sephadex G-75 column (Pharmacia LKB) with 1.1 ml fractions collected in phosphate-buffered saline (PBS). TCA precipitation was performed by incubating aliquots of the fractions in 10% trichloroacetic acid for 1 hour at 4° C. Pellets formed after centrifugation were then counted in Clinigamma counter (Pharmacia LKB). MC/9 Proliferation Assay.

Biological activity of hIL-10 was determined using a colorimetric MTT dye-reduction assay. See, e.g., Tada, et al. (1986) *J. Immun. Meth.* 93:157–165; and Mosmann (1983) *J. Immun. Meth.* 65:55–63, which are incorporated herein by reference. Briefly, five thousand MC/9 cells per well in 100 µl media containing 100 U mIL-4/ml in a 96 microtiter well were treated for 48 hours with varying amounts of human IL-10. The hIL-10 standard was used at a maximum of 200 units/100 µl and two-fold serially diluted. Twenty-five microliters of 5 mg/ml MTT was added and incubated for 3 to 5 hours. The cells were then detergent-lysed in 10% SDS with 10 mM HCl and the plates were read for absorbance at 570 nm.

Binding Assays and Scatchard Analysis.

Approximately $5 \times 10^6$ cells for each cell line tested were pelleted by centrifugation at 200×g for 10 min., washed in PBS, and resuspended in 200 µl binding buffer (PBS, 10% fetal calf serum, 0.1% $NaN_3$) containing iodinated hIL-10 at a concentration of 100–500 pM. After incubation at 4° C. for two hours in a rotary mixer, the cells were centrifuged at 200×g for 10 minutes, resuspended in 100 µl binding buffer without labeled hIL-10, layered over 200 µl of a 1:1 mixture of dibutyl-and dioctyl-phthalate oils in elongated microcentrifuge tubes, centrifuged at 400×g for 5 minutes at 4° C., and quick frozen in liquid nitrogen. The cell pellets were then cut and counted in a Clinigamma 1272 counter (Pharmacia LKB). Non-specific binding was determined by performing the binding in the presence of 500 to 1000-fold molar excess unlabeled hIL-10. For saturation binding experiments, two-fold serial dilutions of approximately 600 pM solution of iodinated hIL-10 were used, with a parallel series done to determine non-specific binding. Scatchard analysis was performed on the data points obtained using the EBDA Program (Elsevier-Biosoft, Cambridge, U.K.). Antibody inhibition was performed under the above binding conditions but with the addition of a 100-fold molar excess of each of the indicated monoclonal antibodies. Cytokine specificity was determined under similar conditions but with the addition of 500-fold molar excess of the cytokines indicated.

Chemical cross-linking.

Cross-linking may be done using BS3, Sulfo-EGS, or EDC following manufacturer's instructions, Pierce, Rockford, Ill.

Alternatively, about $5 \times 10^6$ cells were incubated for 4 hours at 4° C. in 400 µl of binding medium consisting of RPMI-1640, 50 mM HEPES, 0.02% $NaN_3$, 0.5% BSA, and 1 nM $^{125}$I-hIL-10 with or without 1000 nM unlabeled hIL-10. The cells were washed 2 times with RPMI-1640 and then resuspended in 1 ml of RPMI-1640. To the cell suspension, 6 µl of dimethyl sulfoxide containing 10 µg/ml disuccinimidyl suberate (DSS) was added and the cells were incubated for 20 minutes on ice. The reaction was stopped by addition of 50 μl 1 M Tris-HCl (pH 7.5). The cells were collected by centrifugation and were then lysed by adding 30 μl of the lysis buffer containing the following: Tris-HCl (pH 7.5), 140 mM NaCl, 2 mM EDTA, 10 mg/ml leupeptin, 2 mM iodoacetamide, 2 mM O-phenanthroline, and 1% Triton X-100. The lysates were centrifuged at 10,000×g for 10 min at 4° C., and 10 μl of the supernatants were electrophoresed on a 7.5% gradient polyacrylamide gel (Daiichi Chemicals Co., Tokyo) in the presence of SDS according to Laemmli (1970) *Nature* 227:680–685, under reducing conditions.

COS7 transfections.

5 μg of the indicated plasmid DNA was mixed with 5×10$^6$ COS7 cells in 250 μl of Dulbecco's Modified Eagle Media with 10% Fetal Bovine Serum and antibiotics in an electroporation cuvette (Bio-Rad, Richmond, Calif.). The cells were electroporated using a Bio-Rad Gene Pulser using 0.20 kV with the capacitance set at 960 μF and the resistance at 200 ohms. After 10 min at room temperature, the cells were put in 10 cm dishes with 10 ml complete media, and allowed to attach. After an overnight incubation at 37° C., the media was replaced with the same media but without serum. Two days later, the cells were detached from the plates by incubating in a phosphate buffered saline with 4 mM EDTA and 0.03% NaN$_3$, harvested, and used for binding assays. Approximately 1×10$^6$ cells were used for each binding determination.

EXAMPLE 2: Preparation of human and mouse fusion proteins of IL-10 with FLAG sequences.

Nucleic acid constructs encoding fusion proteins as described in FIG. 1 were prepared by standard molecular biology techniques. The FLAG sequence is recognized by commercially available antibodies (IBI-Kodak, Rochester, N.Y.) and does not interfere significantly with the association of the IL-10 fusion protein with the binding protein, as measured in biological assays for IL-10 activity.

EXAMPLE 3: Preparation of a cDNA library from appropriate cell sources.

cDNA libraries were constructed using standard techniques from cell lines which are sensitive to IL-10. See SuperScript Plasmid System for cDNA Systems and Plasmid Cloning, Life Technologies, BRL, Gaithersburg, Md. The BJAB B cell line from human was used, and the mouse MC/9 mast cell or J774 macrophage cell lines were used.

EXAMPLE 4: Enrichment of transformed cells expressing elevated amounts of IL-10 binding protein.

Figure 3:
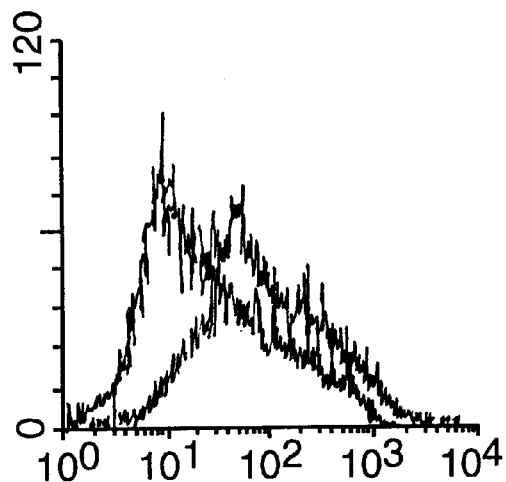
FIG. 3 shows FACS analysis of mIL-10 receptor expression on COS7 cells transfected with an mIL-10 receptor cDNA clone (m3.14). Binding of FLAG-mIL-10 (dark) is competed by a 30–100fold excess of mIL-10 (light), which is equivalent to background.

Cells transfected with the cDNA libraries were subjected to FACS sorting using biotinylated fluorescent FLAG antibodies as markers. After exposing transformed cells to the antibodies, phycoerythrin-streptavidin (PE-streptavidin) was added. The marked cells were then analyzed by FACS to collect the 3–5% of cells expressing the greatest amount of IL-10 binding. See FIG. 2. Selected cells were then used to make cDNA libraries. Cells were subjected to three cycles of enrichment. FIGS. 2 and 3 show that IL-10 can compete with the FLAG-IL-10 binding.

Alternatively, cells which expressed IL-10 binding were selected by affinity purification, i.e., panning, on plates coated with anti-FLAG antibodies. Cells were subjected to multiple cycles of the panning procedure, and those cells isolated and their exogenous vector inserts isolated and characterized.

EXAMPLE 5: Characterization of the IL-10 binding protein encoding nucleic acid.

The isolated inserts from both the human and mouse cDNA sources were further characterized by sequencing by standard methods.

Figure 4:
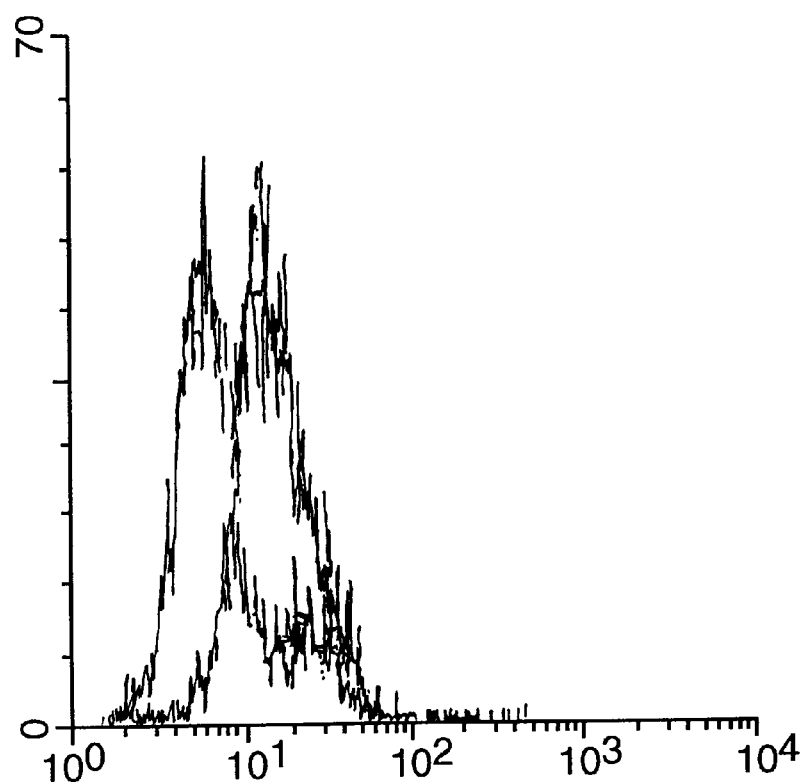
FIG. 4 shows FACS analysis of hIL-10 receptor expressed on a human B cell line BJAB. Cells in late log phase were diluted in fresh medium and assessed for hIL-10 receptor expression 12–16 hr later. Binding of FLAG-mIL-10 (right profile) is competed by a 30–100-fold excess of mIL-10 (left profile), which is equivalent to background.
Figure 5A:
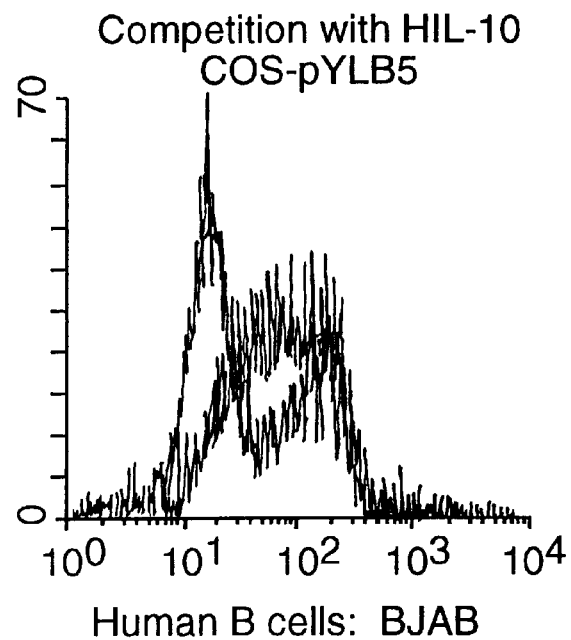
FIGS. 5A–5B, show FACS analysis of hIL-10 receptor expression on COS7 cells transfected with an hIL-10 receptor cDNA clone (YLB5).
Figure 5B:
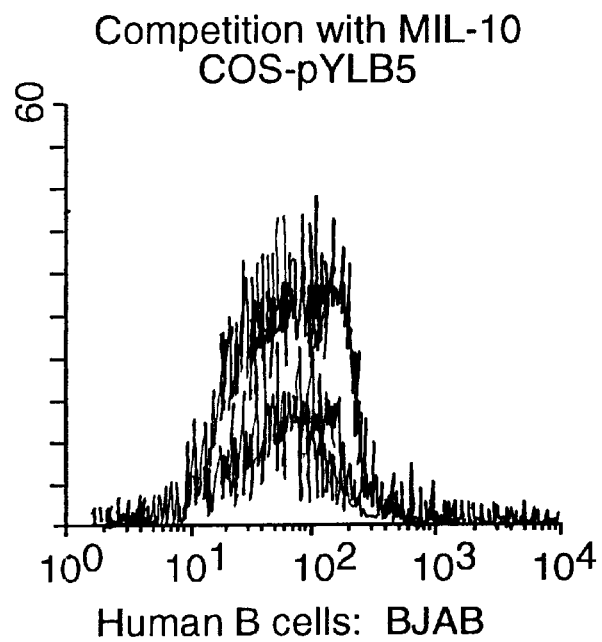

FIGS. 2, 3, 4, and 5 show that most of the cells after selection have a higher fluorescence intensity. Moreover, the binding signal is competed by a 50×excess of IL-10. FIG. 3 shows mouse cells. FIG. 4 shows cells transfected with the m3.14 mouse clone and expressing the resulting receptor. These cells exhibit fluorescence intensity which is competed by a 50×excess of IL-10 (left profile). FIG. 5 shows cells transfected with pYLB5 which was the original isolate of the human cDNA clone obtained through multiple cycles of enrichment. This clone was used to isolate the pSW8.1 clone from the original BJAB human cell cDNA library.

EXAMPLE 6: Lactoperoxidase labeling method retains the biological activity of hIL-10.

Purified CHO-derived hIL-10 was iodinated to high specific activity (100 to 200 μCi/μg protein) using the lactoperoxidase method. Initial attempts to label CHO-derived hIL-10 with the IODO-GEN reagent (Pierce, Rockford, Ill.) resulted in protein of insufficient specific activity to be used in receptor characterization. The lactoperoxidase method yielded iodinated hIL-10 with a specific activity approximately five-fold higher than that obtained with IODO-GEN.

Figure 6:
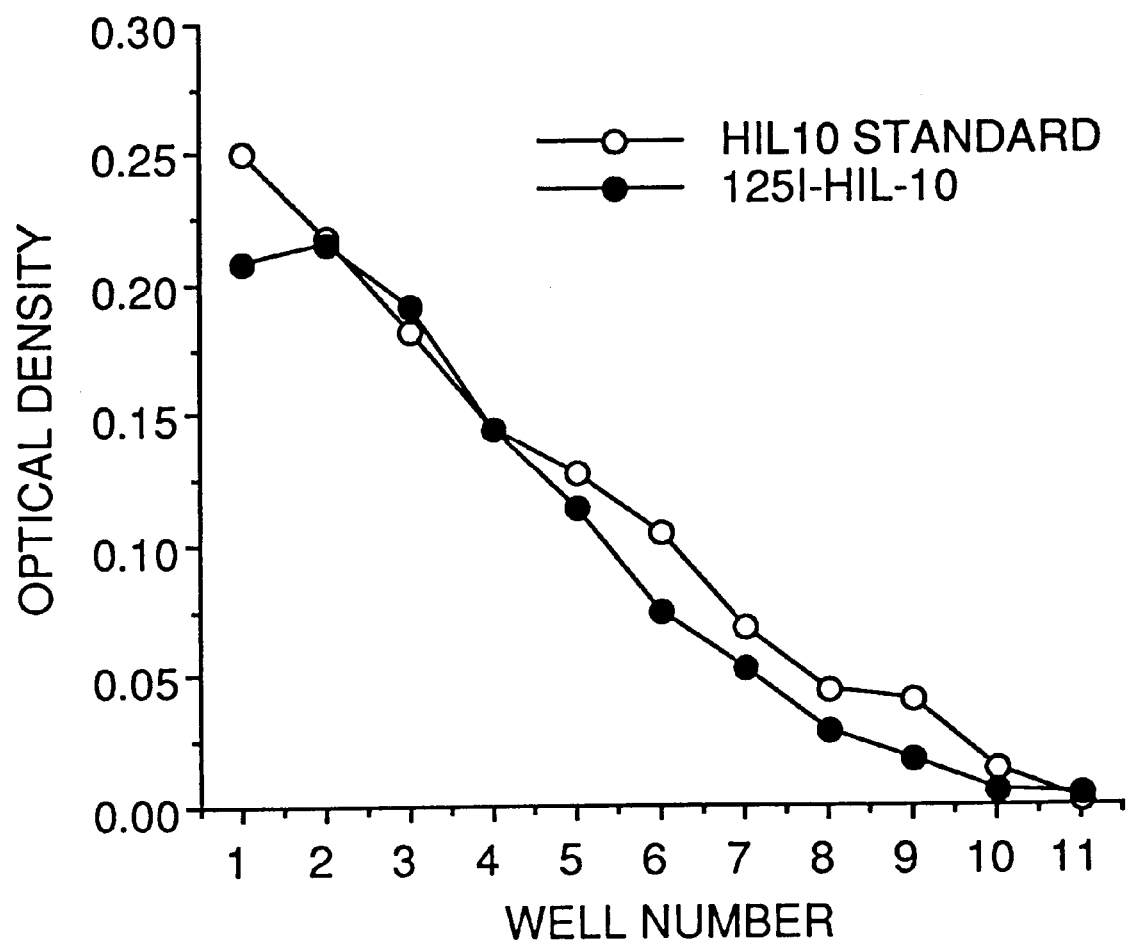
FIG. 6 shows an MC/9 proliferation assay of radioiodinated hIL-10. Unfractionated hIL-10 at a concentration of 50 ng/ml was tested for its proliferative effect on MC/9 cells using a colorimetric MTT assay. Unlabelled hIL-10, used also at 50 ng/ml at the highest concentration, was examined in parallel. The samples were two-fold serially diluted for assay.

In order to determine if the high specific activity labeled hIL-10 was biologically active, samples were examined for their ability to induce MC/9 cell proliferation by the method of Thompson-Snipes, et al. (1991) *J. Exp. Med.* 173:507–510. FIG. 6 shows the assay result with 50 ng/ml of iodinated hIL-10 in comparison with the same concentration of unlabeled protein. The estimated activity for the sample was 7.48×10$^2$ units/ml compared to 1.16×10$^3$ units/ml for the standard, giving a retention of 64% biological activity for this sample. Repetition of biological assay results with other samples of iodinated hIL-10 indicated routinely greater than 50% biological activity retention.

EXAMPLE 7: The active form of radiolabeled hIL-10 appears to be a dimer.

Figure 7A:
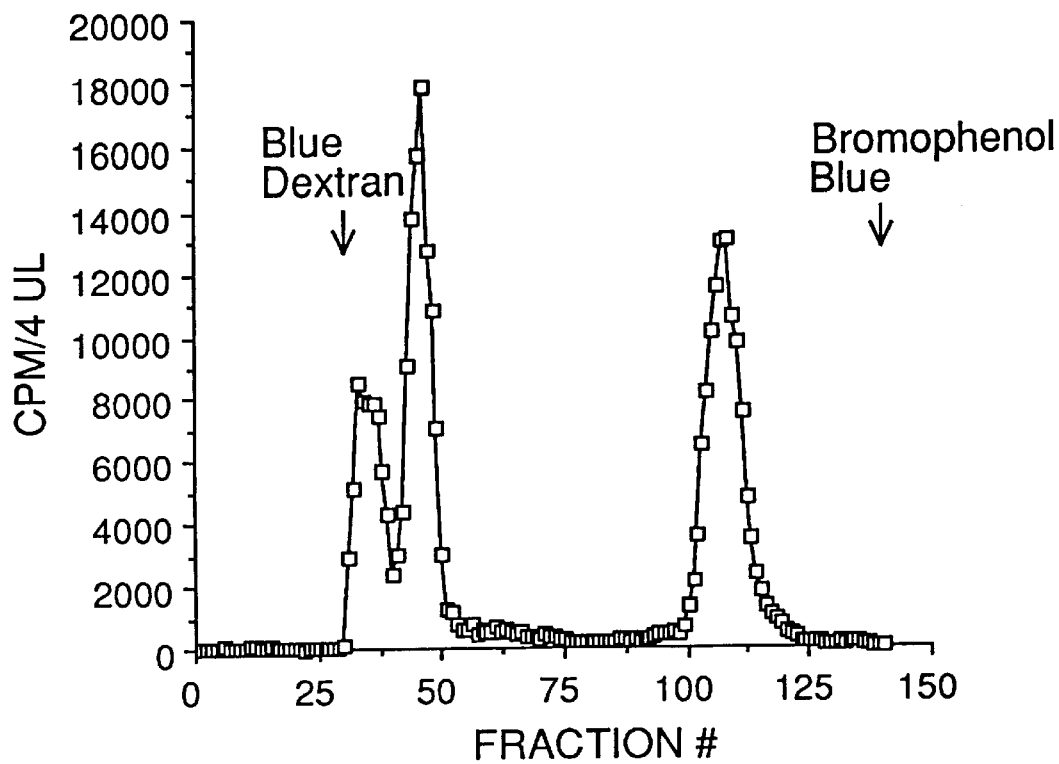
FIGS. 7A–7C, show gel filtration chromatography of radioactivity labeled hIL-10.
Figure 7B:
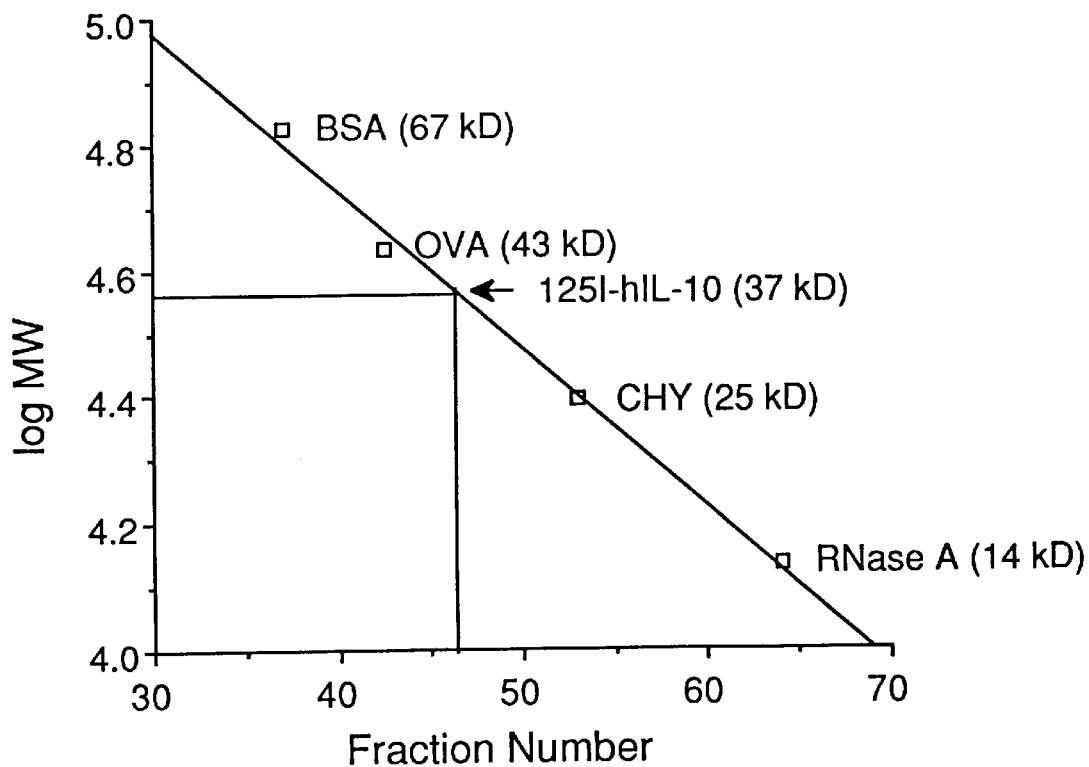
Figure 7C:
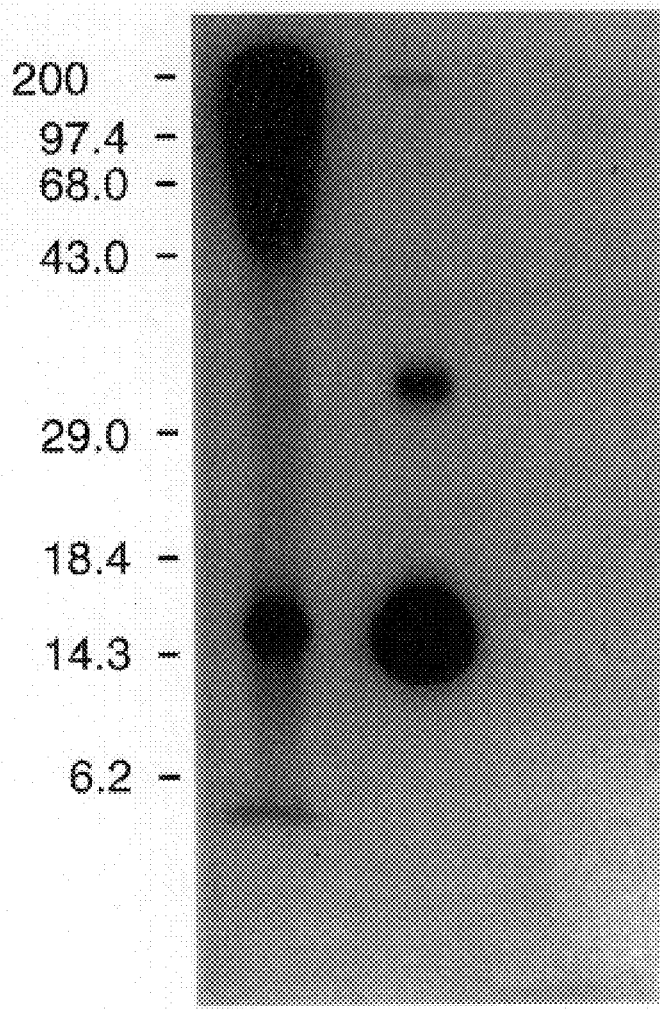

The labeled protein mixture, when passed through a Sephadex G-75 gel-filtration column, was resolved into three distinct species (FIG. 7A). This fractionation was found to be necessary to reduce background binding to target cells. The largest species was a high molecular weight form which elutes with the excluded volume. The smallest species eluted between the lowest molecular weight standard (13.7 kDa) and the dye marker Bromophenol Blue. Sizing with molecular weight standards showed the second species to be approximately 37 kDa (FIG. 7B), consistent with the predicted molecular weight for a hIL-10 dimer. Polyacrylamide gel electrophoresis of the three species in the presence of SDS (FIG. 7C) revealed that the high molecular weight form ran as an aggregate between 43 kDa and 200 kDa. The second species migrated under these conditions at approximately 18 kDa, while the third species was not observed at all. The radioactivity associated with the largest and the second species was TCA precipitable while that associated with the small species was not.

EXAMPLE 8: Radioiodinated hIL-10 binds specifically to its cellular receptors.

Figure 8:
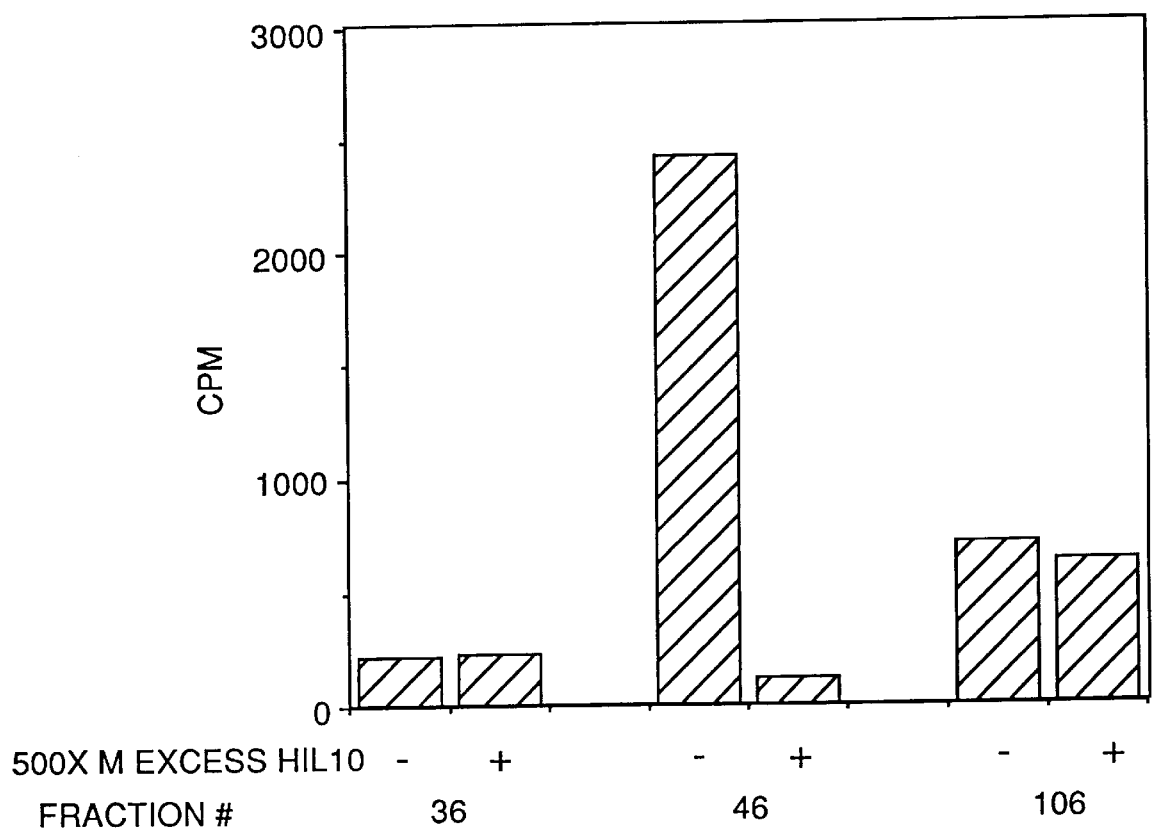
FIG. 8 shows radioiodinated hIL-10 fractions in MC/9 cell binding assays. Duplicate aliquots of the fractions obtained in FIG. 6 were tested for binding to MC/9 cells in the presence or absence of a 500-fold molar excess of unlabeled hIL-10. The concentration of iodinated hIL-10 in the assay was 100 pM.

Based on the observation that the radioiodinated hIL-10 was biologically active, fractionated samples were tested for their ability to bind specifically to candidate cell lines. MC/9 cells respond to hIL-10 by proliferation, so they were first used to determine the binding specificity of hIL-10. FIG. 8 shows that when the three species fractionated from the G-75 column were tested for binding to MC/9 cells, the 37 kDa species, but not the other two, was able to bind to a high degree; moreover, a 500-fold molar excess of unlabeled IL-10 protein could block greater than 90% of the labeled IL-10 binding.

Figure 9:
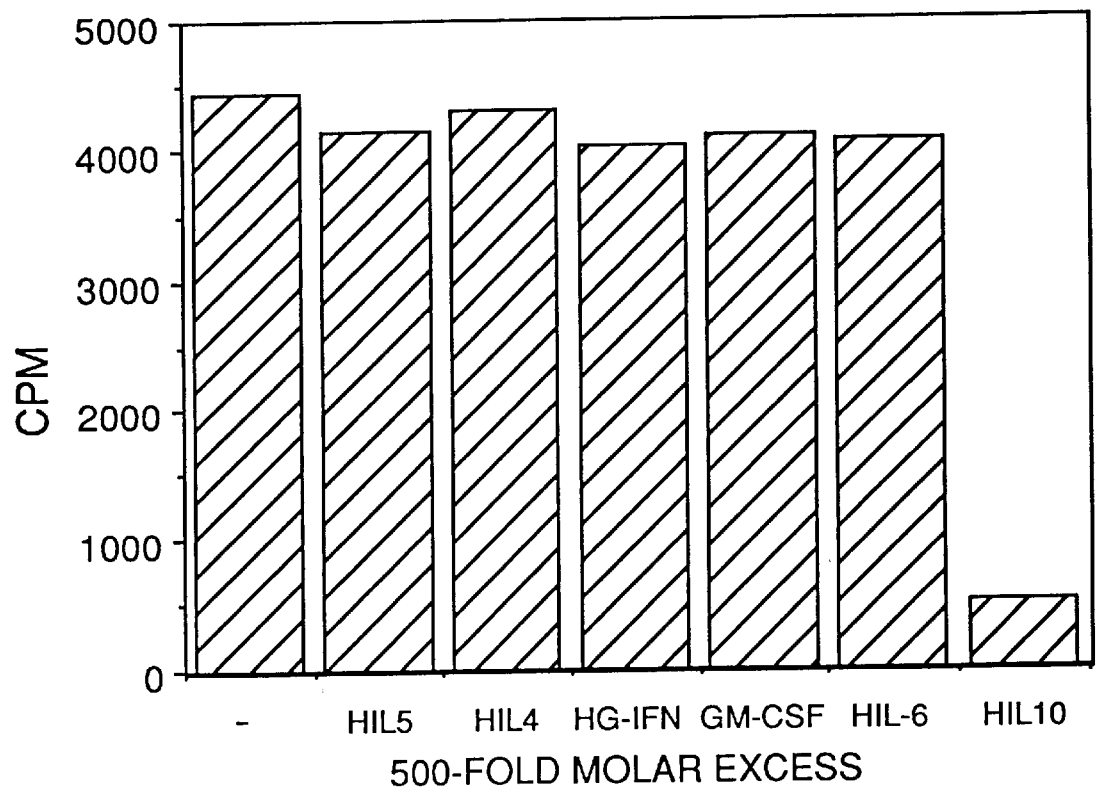
FIG. 9 shows a binding competition assay. Radioiodinated hIL-10 at a concentration of 150 pM was tested for binding to TF-1 cells in the absence or presence of 500-fold molar excess of unlabeled cytokine. Radioactivity bound was determined after washing and pelleting the cells.
Figure 10:
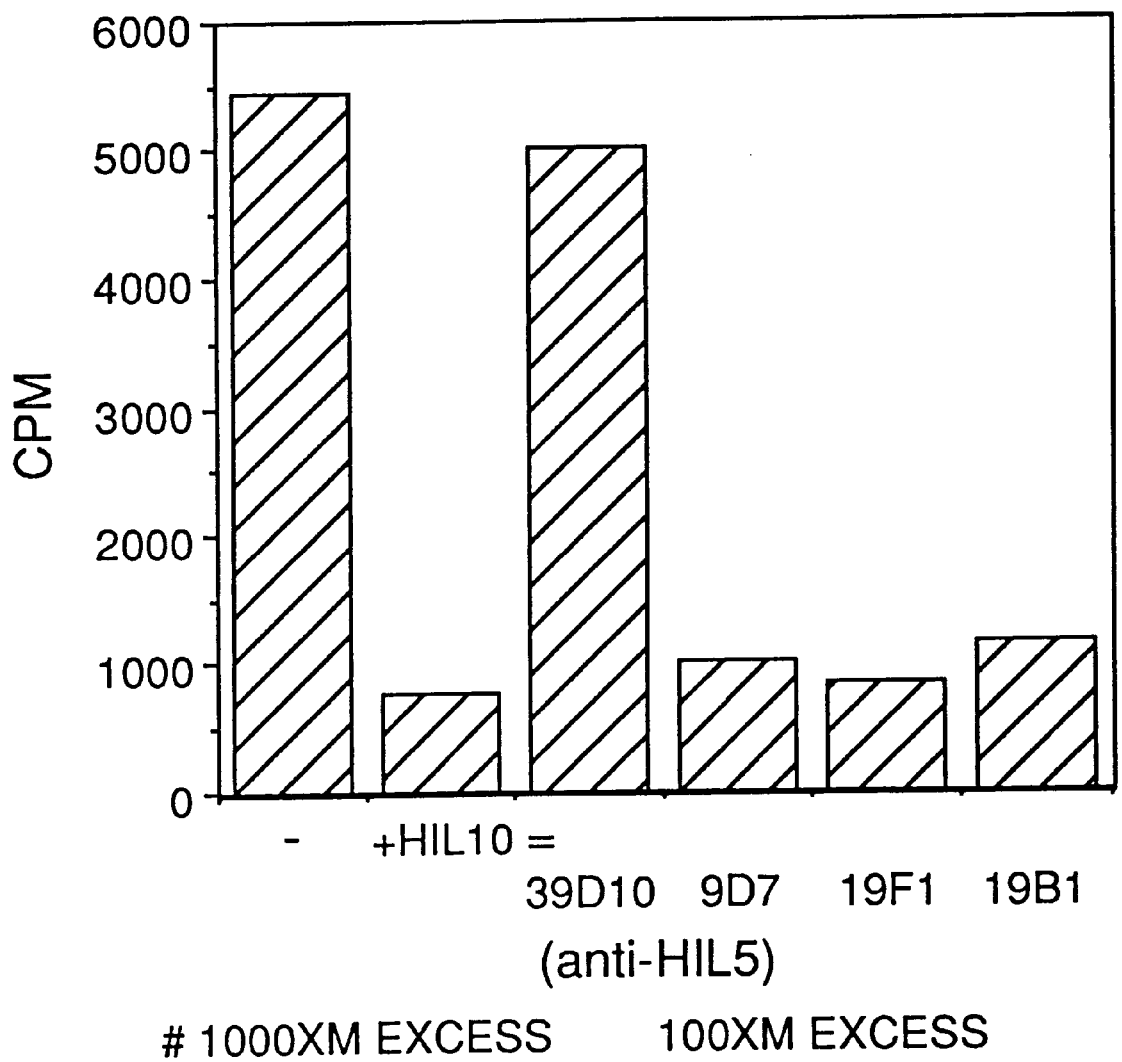
FIG. 10 shows monoclonal antibody inhibition of radioiodinated hIL-10 binding to TF-1 cells. The iodinated hIL-10 at 150 pM was tested for binding to TF-1 cells in the presence or absence of 500 fold molar excess of unlabeled hIL-10 or 100 fold molar excess of purified anti-hIL-5 monoclonal antibody 39D10 or anti-hIL-10 monoclonal antibodies 9D7, 19F1, and 19B1.

In order to ascertain the specificity of hIL-10 binding to its receptor, other cytokines, as well as monoclonal antibodies to hIL-10, were tested for their ability to inhibit the binding of iodinated hIL-10 to its cell surface receptor. FIG. 9 shows that excess hIL-10 was capable of competing with labeled hIL-10 in binding to TF-1 cells. In contrast, hIL-5, hIL-4, IFN-γ, GM-CSF, and hIL-6 were ineffective in competition. In order to further demonstrate that the binding of hIL-10 to TF-1 cells was specific, monoclonal antibodies to hIL-10 and hIL-5 were examined for their ability to block binding of iodinated hIL-10 to its receptor. FIG. 10 shows that neutralizing monoclonal antibodies generated against hIL-10 were capable of inhibiting the binding of labeled hIL-10 to TF-1 cells, while an anti-human IL-5 monoclonal antibody was unable to block binding of labeled IL-10 as expected.

Figure 11A:
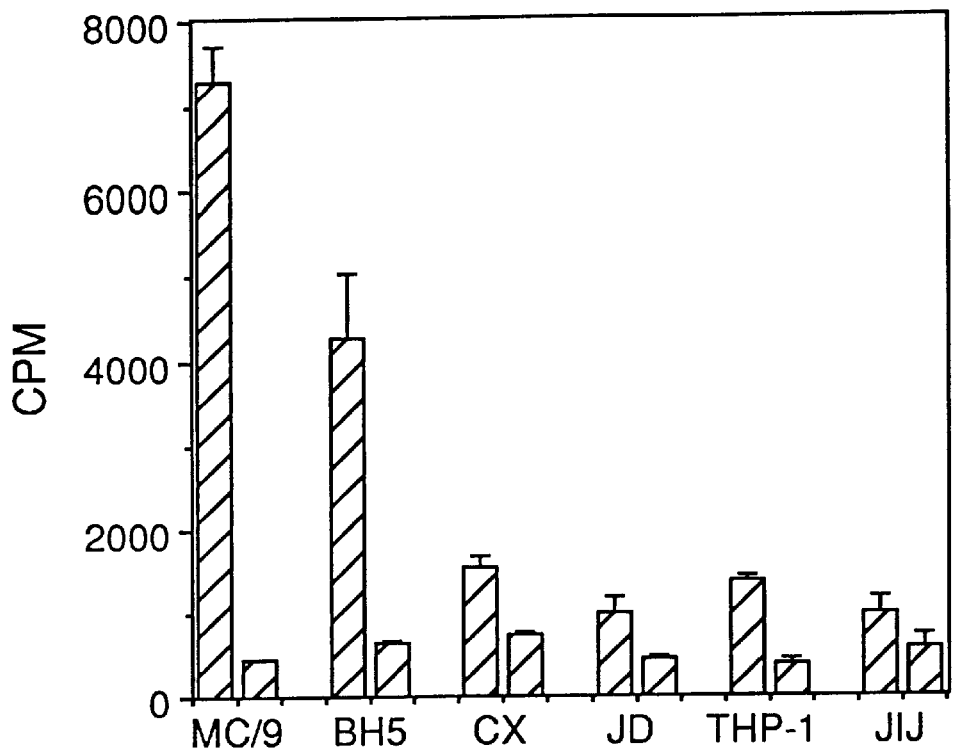
FIGS. 11A–11B, show binding of radiolabeled hIL-10 to different cell lines. Approximately $5\times10^6$ cells were used for each sample.
Figure 11B:
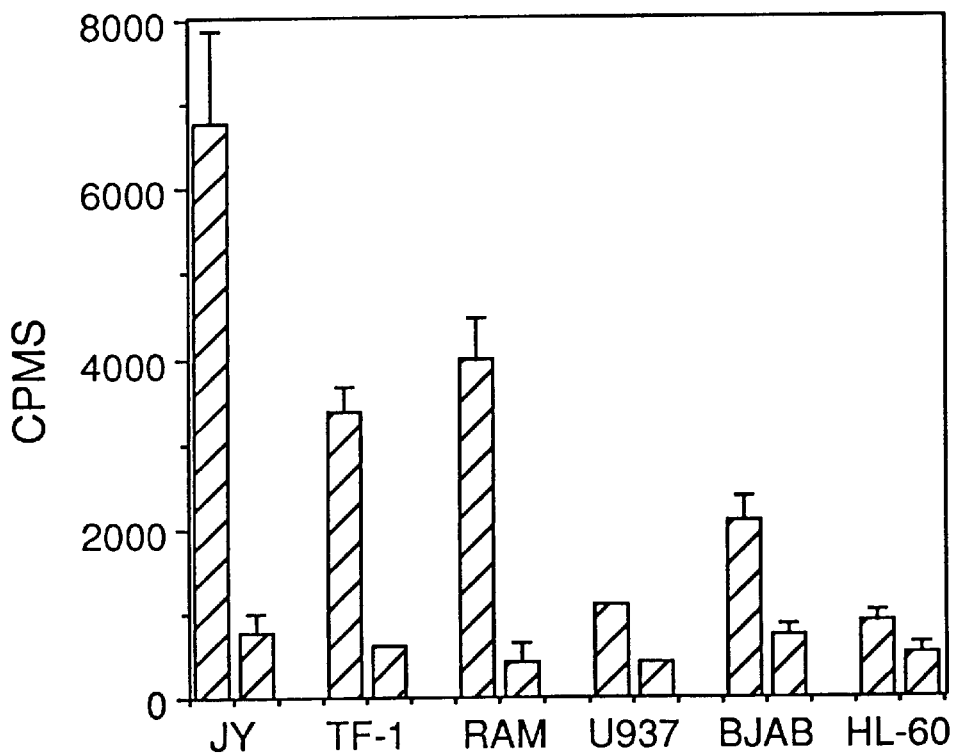

Binding assays with a number of different cell lines indicated that hIL-10 was able to bind to most of these lines to varying extents (FIG. 11). The highest degree of binding was seen with the mouse mast cell line MC/9 and the human B-lymphoma line JY. TF-1 (a human erythroleukemia line) as well as Ramos and BH5 (human B-lymphoma lines) show a reduced level of binding relative to JY and MC/9. Human IL-10 binds to the other cell lines examined at relatively low levels. A binding assay with WEHI 265.1, a mouse monocytic cell line, also shows a relatively low level of binding.

EXAMPLE 9: Human IL-10 binds to cellular receptors with high affinities.

Figure 12A:
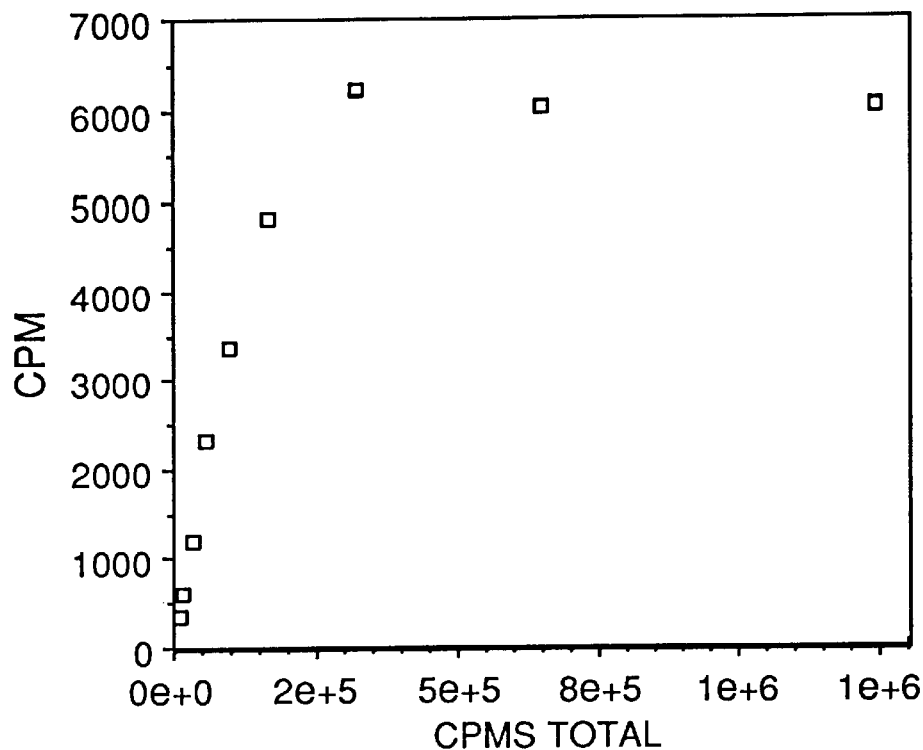
FIGS. 12A–12B, show saturation binding of MC/9 cells with radioactive hIL-10.
Figure 12B:
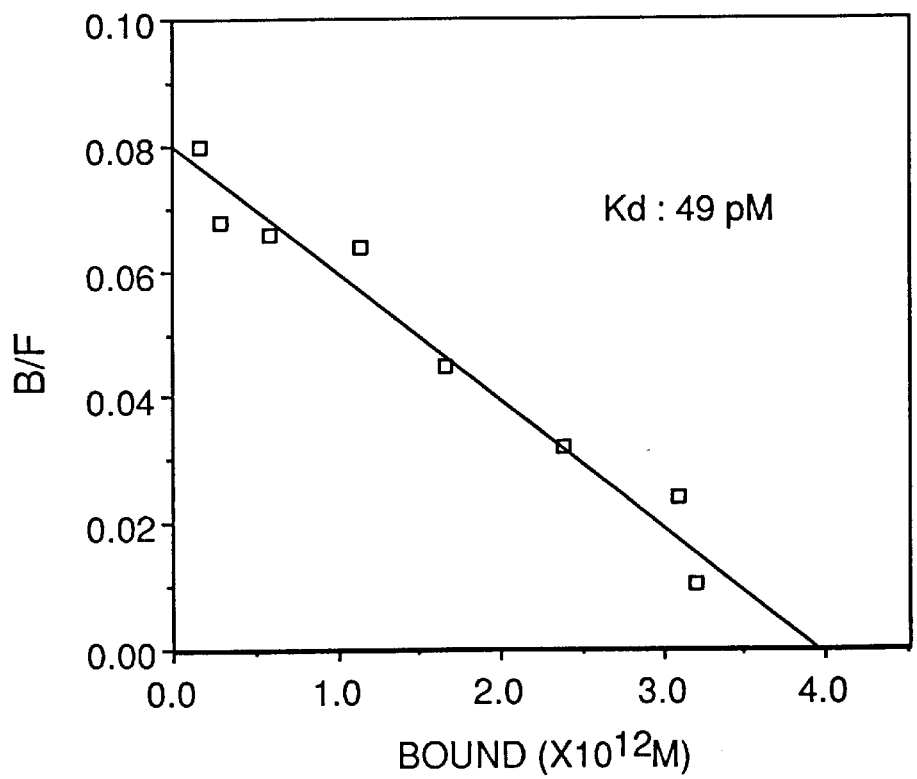
Figure 13A:
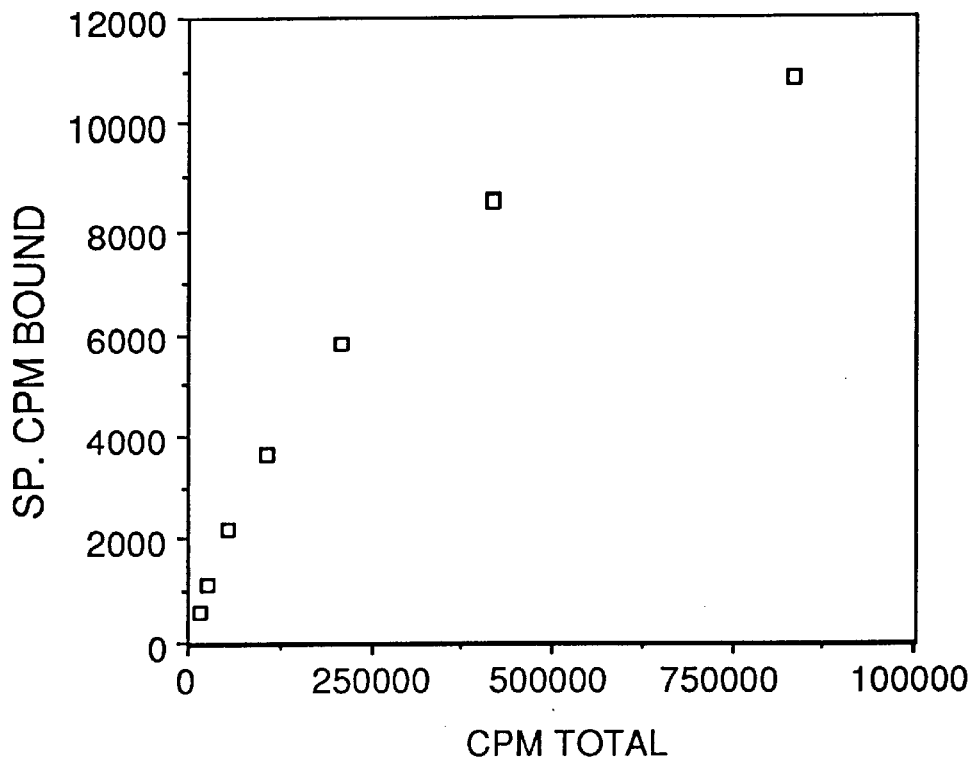
FIGS. 13A–13B, show saturation binding of JY cells with fractionated radioactive hIL-10.
Figure 13B:
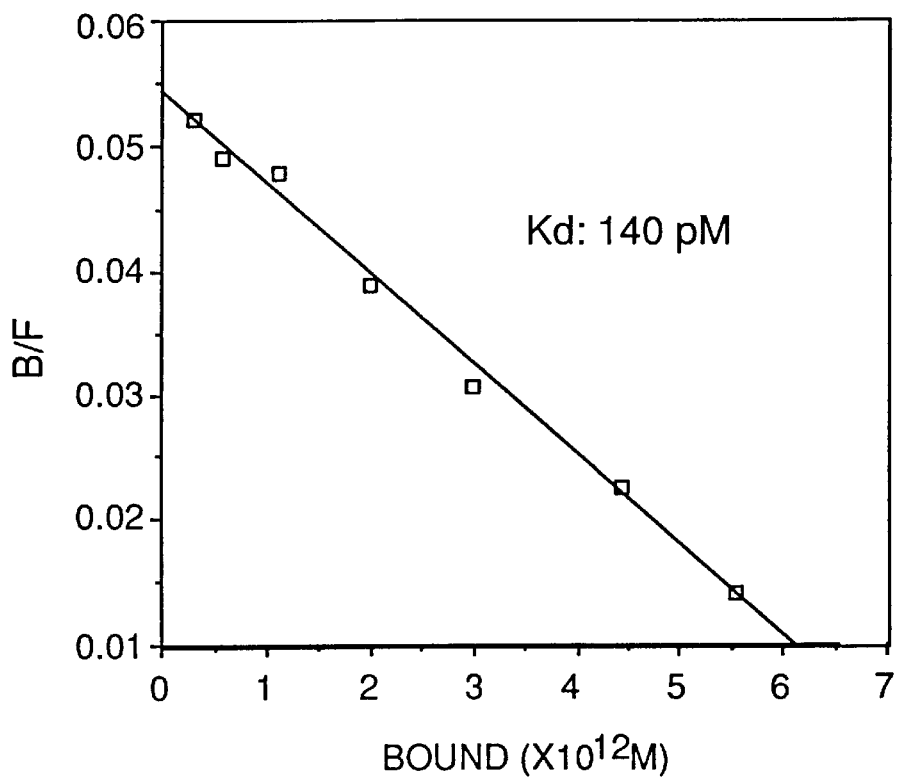

After demonstrating the specific binding of fractionated, iodinated hIL-10 to target cell lines, and the retention of biological activity of this labeled protein, it was decided to determine the binding affinity and estimate the number of binding sites/receptors per cell. Typical saturation binding curves with JY and MC/9 cells are shown in FIGS. 12A and 13A, respectively. Maximal binding occurs at approximately 300 to 400 pM of labeled hIL-10 for both cell lines. Scatchard analyses of representative binding data (FIGS. 12B for JY and 13B for MC/9) provided linear graphs with slopes yielding a Kd of approximately 150 pM for the JY cell line and 49 pM for the MC/9 line. Bmax values obtained, which represented the maximal concentration of ligand bound to cells, were 4.0 pM and 7.5 pM for MC/9 and JY cells, respectively. Assuming that one hIL-10 dimer ligand molecule binds one receptor, these results provide an estimate of approximately 100 unoccupied receptors per cell for MC/9 and 180 unoccupied receptors per cell for JY. From several independent experiments, the human IL-10 binding affinity for JY and MC/9 cells was approximately 50 to 170 pM, with between 100 and 300 unoccupied receptors per cell.

EXAMPLE 10: Mouse IL-10 receptor binding appears to be species-specific whereas human IL-10 receptor binding is not.

Figure 14A:
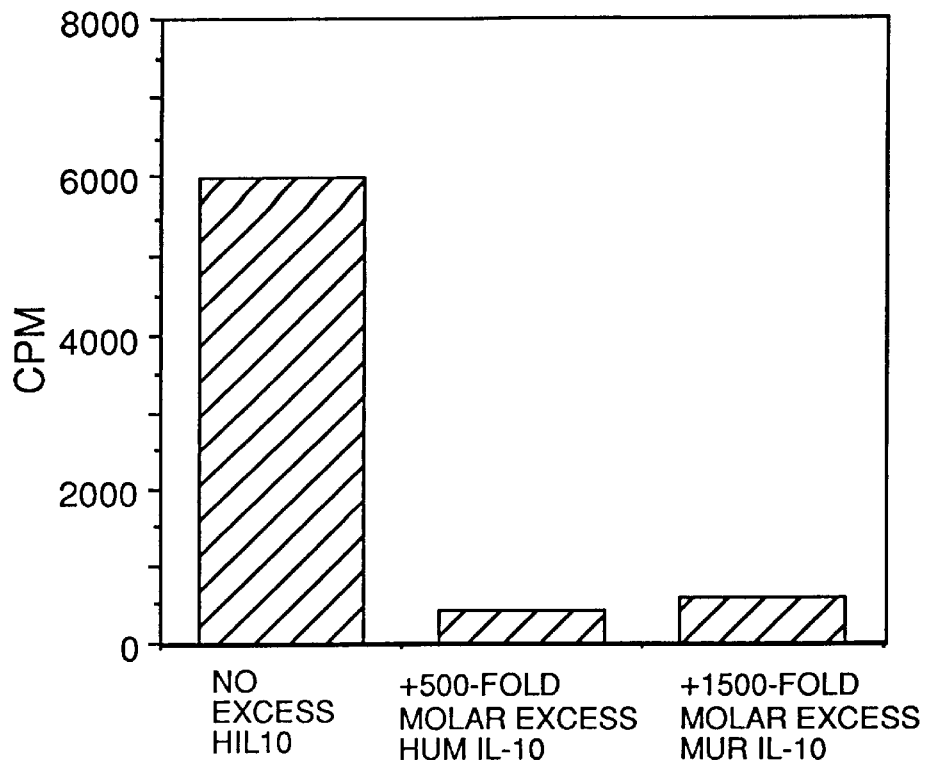
FIGS. 14A–14B, show human or mouse IL-10 competition with radioiodinated hIL-10 binding to MC/9 or JY cells.
Figure 14B:
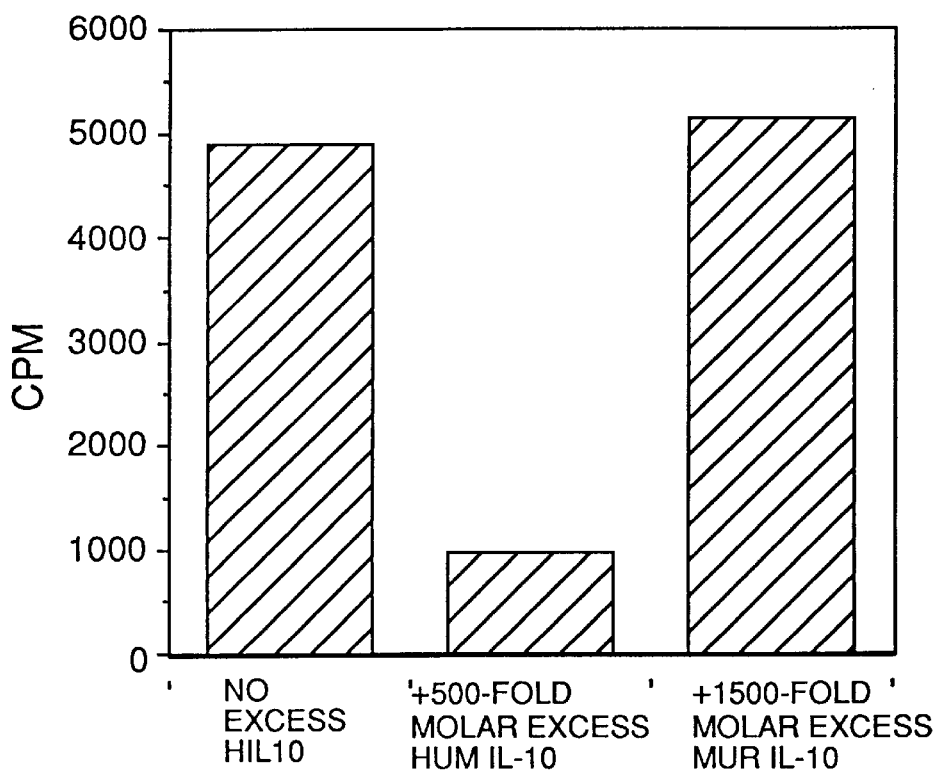

In order to examine the species-specificity of receptor binding, the ability of mouse and human IL-10 to compete with labeled human IL-10 for binding to mouse and human cell lines was examined. FIG. 14 shows the results of such competition experiments. Because the specific biological activity of E. coli-derived murine IL-10 was 60–70% of human IL-10, as determined by the MC/9 biological assay, the concentrations of human and murine IL-10 in the competition experiments were adjusted accordingly. FIG. 14A shows that both mouse and human IL-10 were able to block the binding of labeled hIL-10 to the mouse MC/9 line. In contrast, FIG. 14B shows that human IL-10, but not mouse IL-10, is able to successfully compete with the binding of labeled hIL-10 to the human B lymphoma line JY.

EXAMPLE 11: Multiple complexes were found after chemical cross-linking of radiolabeled hIL-10 to its receptors.

To characterize the receptor for hIL-10 in JY and MC/9 cells, cells were first incubated with 1 nM $^{125}$I-hIL-10, and then treated with bifunctional linker disuccinimidyl suberate, and analyzed by SDS-PAGE and autoradiography. A few relatively faint and two relatively strong bands were detectable with apparent relative molecular weight (Mr) of 110–180 kDa (minor bands), 98 kDa, and 83 kDa, respectively, with JY cells. The apparent Mrs were estimated based on co-electrophoresed prestained molecular size standards. The 98 kDa and 83 kDa bands were also observed with MC/9 cells although the signals were relatively weaker. Formation of all cross-linked complexes was completely inhibited by the presence of 1000-fold excess amount of unlabeled hIL-10. Upon reevaluation of the migration of the prestained molecular weight standards, the major bands were reassigned molecular weights of about 90–110 kD.

EXAMPLE 12: Specificity of binding to human IL-10.

Figure 15A:
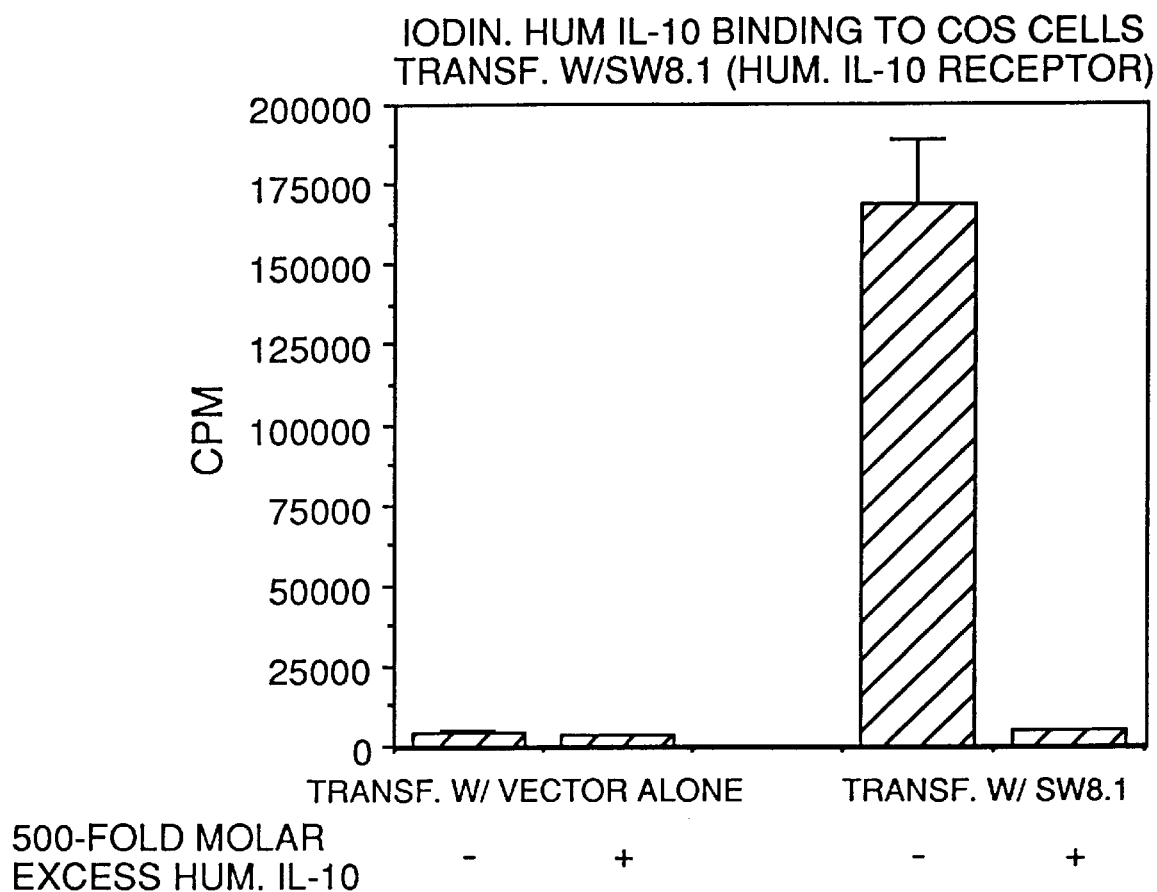
FIGS. 15A–15B, show specificity of binding to labeled human IL-10. COS7 cells were transfected with either the human (SW8.1) and mouse (m3.14) cDNA clones, allowed to express the clone for 72 hours, then tested for binding to iodinated human IL-10.
Figure 15B:
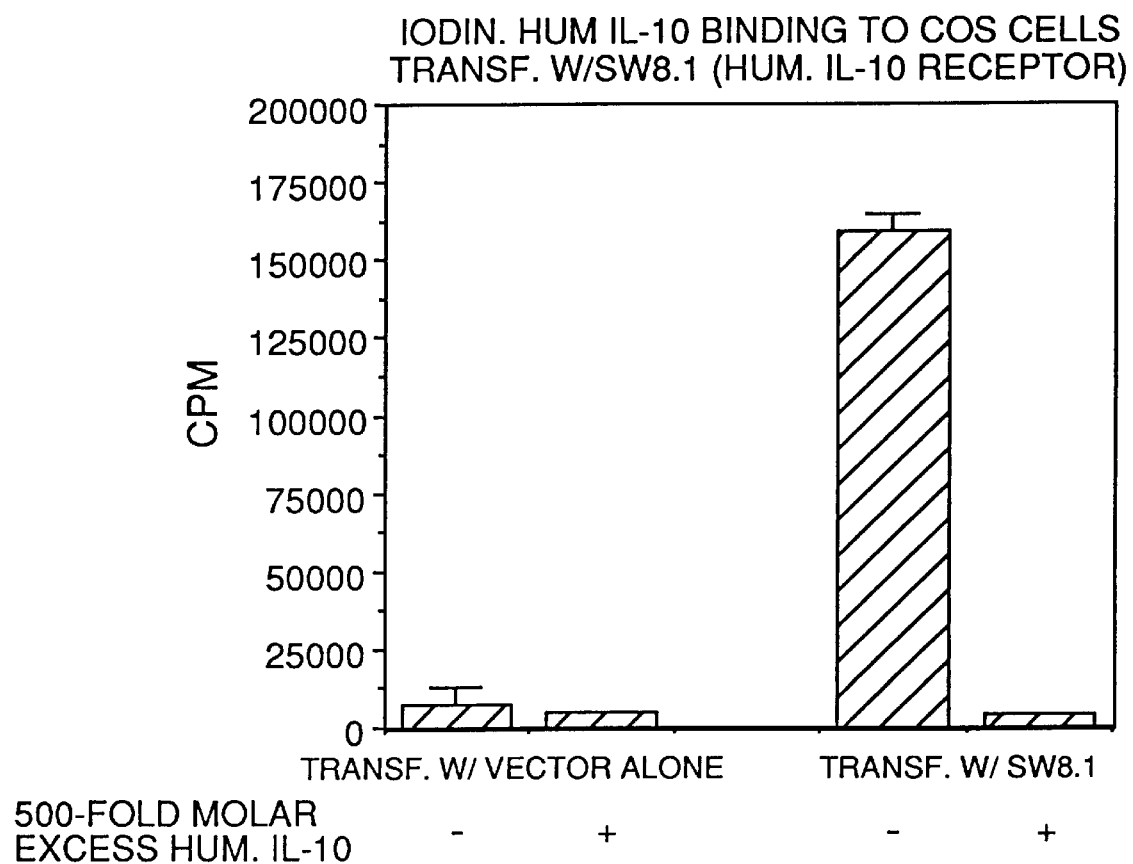

COS7 cells were transfected with the human or mouse cDNA clones, allowed to express the vector for 72 hours, and tested for binding to radioiodinated human IL-10. FIG. 15, panel A shows the human IL-10 receptor and FIG. 15, panel B shows the mouse IL-10 receptor.

These results show that unlike the vector alone, the cloned receptor cDNA is able to confer specific binding ability for human IL-10 on COS cells. Both the human and mouse clones are able to bind human IL-10.

EXAMPLE 13: Scatchard analysis of binding of human IL-10 to the human or mouse receptors.

Figure 16A:
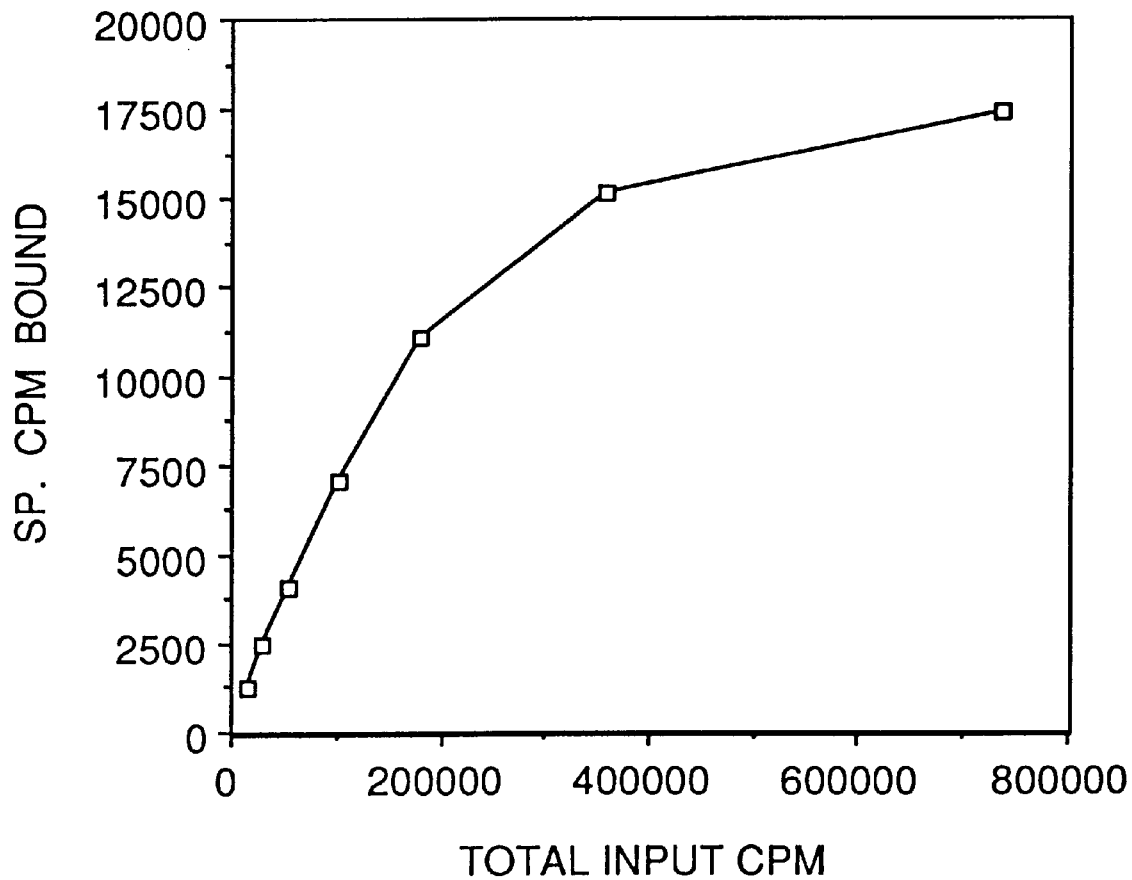
FIGS. 16A–16B show saturation binding of cloned human IL-10 receptor with labeled human IL-10.
Figure 16B:
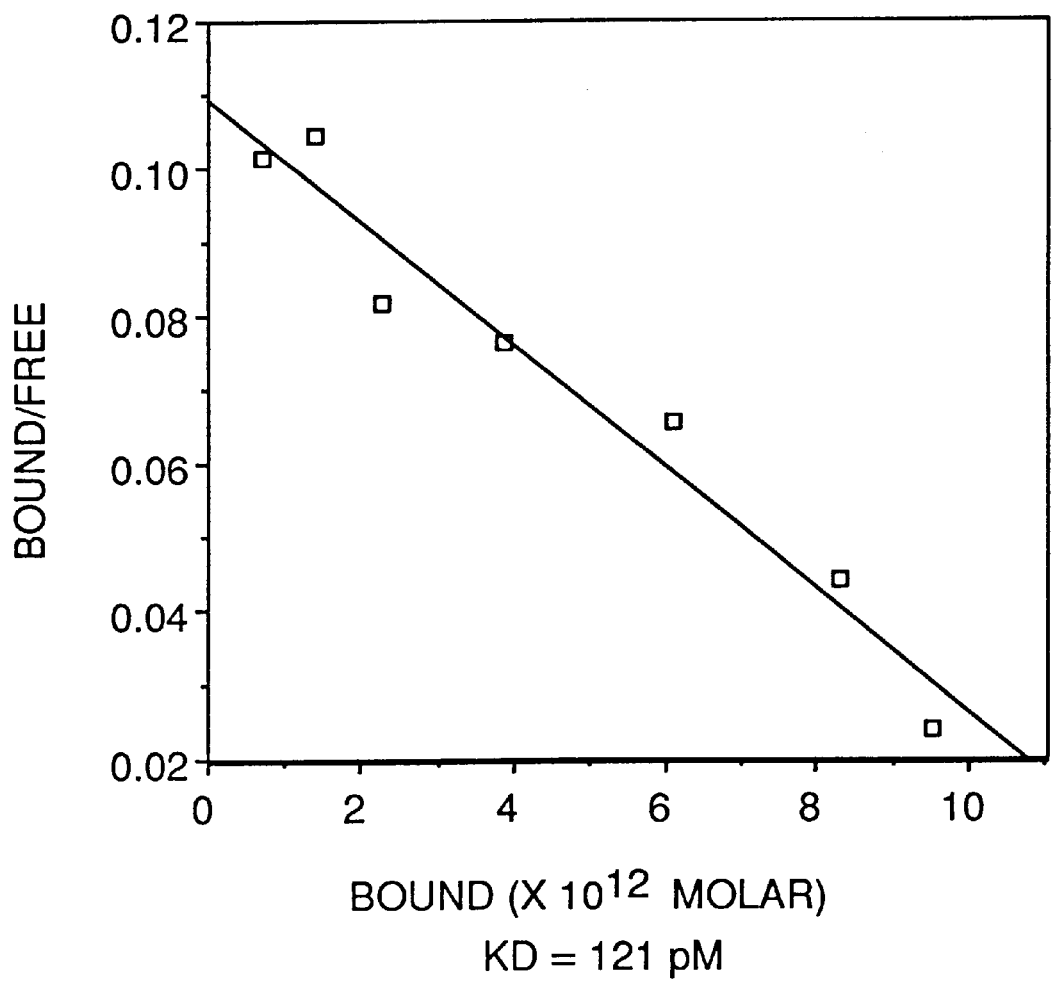
Figure 17A:
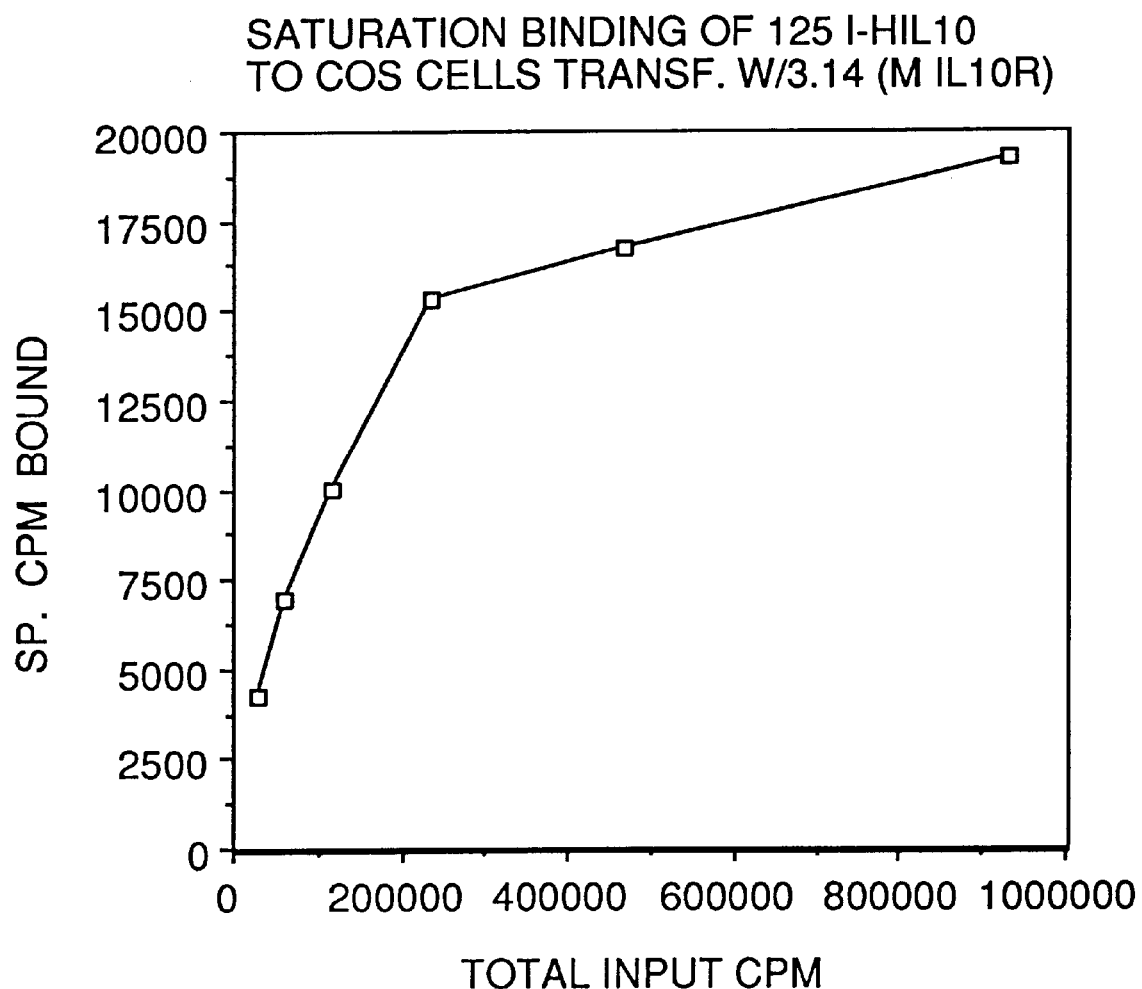
FIGS. 17A–17B, show saturation binding of cloned mouse IL-10 receptor with labeled human IL-10.
Figure 17B:
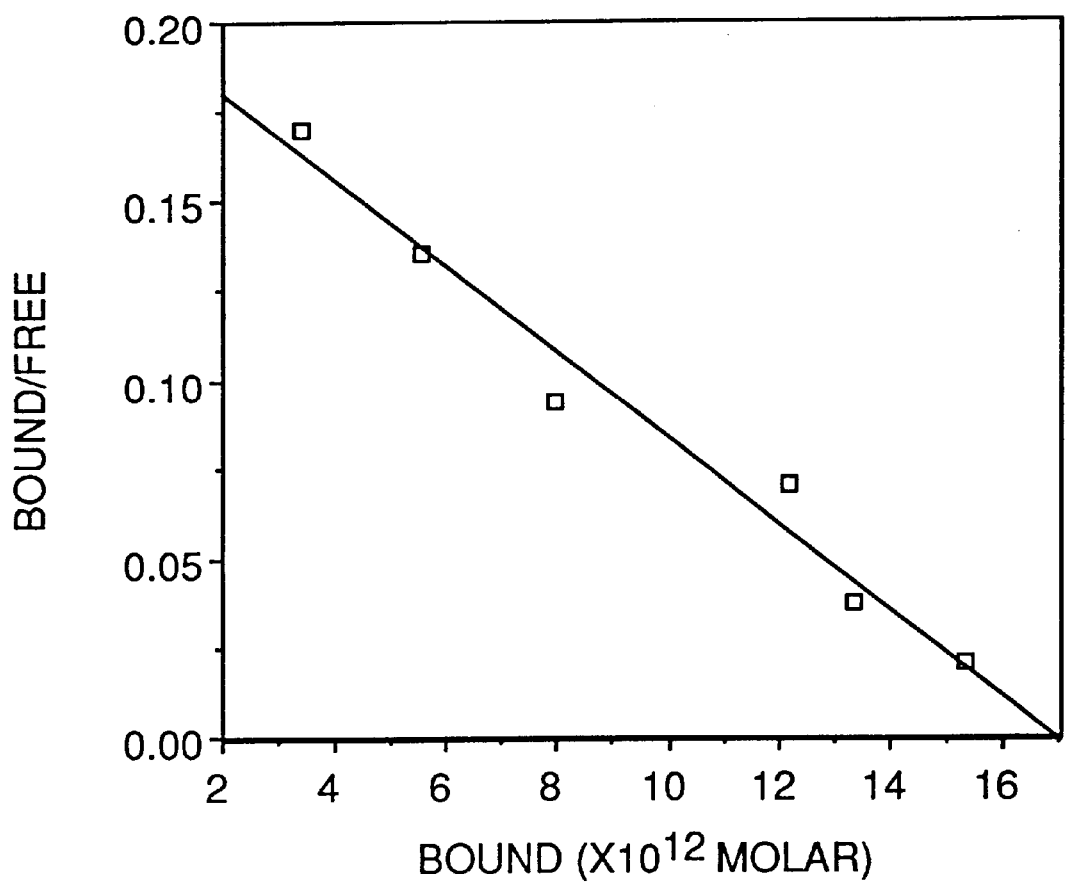

Binding assays were performed. For FIGS. 15A and 15B, iodinated human IL-10 was used at a concentration of 300–400 pM. For FIGS. 16 and 17, the highest concentration was 1 nM. Background was determined by performing binding at 500-fold molar excess. Points represent averages of duplicates.

EXAMPLE 14: Expression cloning and characterization of a human interleukin-10 receptor.

Numbered references for this section are found at the end of this section.

MATERIALS AND METHODS

Cytokines

Purified recombinant hIL-10 was provided by Dr. T. L. Nagabhushan, Schering-Plough Research Institute (Kenilworth, N.J.). Purified mIL-10 was provided by Dr. Satish Menon (DNAX). Concentrated COS7 transfection supernatants served as a source of vIL-10 (7, 24). $^{125}$I-hIL-10 with specific activity of ~100 μCi/μg was from Dupont-NEN (North Billerica, Mass.). Cytokines used in competition experiments were provided by various investigators at DNAX.

Cell lines and Antibodies

BJAB cells were provided by Dr. J. Banchereau (Schering-Plough; Dardilly, France) and maintained in RPMI1640 supplemented with 10% FCS (R10 medium). Ba/F3 cells were provided by Dr. T. Kitamura and maintained in R10+50 μM β-mercaptoethanol and 10 ng/ml mIL-3 (BaF medium). U937 cells were obtained from the American Type Culture Collection and were cultured in R10 with or without 1.5% DMSO. DMSO induces differentiation of U937 cells to cells with properties characteristic of mature macrophages (25, 26). RPMI8866 cells and Daudi (Burkitt lymphoma) cells were as described (27) and were all maintained in R10+50 μM β-mercaptoethanol. COS7 cells were maintained in DMEM supplemented with 5% FCS. Transfection of COS7 and Ba/F3 cells were performed as described (23, 28). Anti-hIL10 (12G8) and its isotype control (GL117) Mab were provided by Dr. J. Abrams and Mr. J. Silver. Anti-FLAG Mab M1 and M2 were purchased from IBI-Kodak (Rochester, N.Y.). SA-PE and Mab used in magnetic-bead depletion experiments were purchased from Becton Dickinson (Mountain View, Calif.).

Purification of human cells for RNA isolation

Human PBMC were isolated from buffy coats from healthy donors by centrifugation over Ficoll-Hypaque (Pharmacia, Uppsala, Sweden) (7). PBMC were incubated in cell culture dishes for 40–60 minutes at 37° C. Non-adherent cells were washed away, and the adherent cells were directly lysed on the plates with guanidinium thiocyanate for RNA preparation as described previously (18, 19). Human monocytes/macrophages of 80–90% purity were isolated by adherence to gelatin-coated plates as described (7, 29)

T cells and LGL cells were isolated from PBMC following adherence, passage over a nylon wool column, density centrifugation on a percoll gradient, and negative selection by magnetic beads. Briefly, PBMC were incubated at $10^8$ cells/100 mm tissue culture dish (Becton Dickinson, Lincoln Park, N.J.) for 45 min at 37° C. Nonadherent cells were removed and passed over a nylon wool (Robbins Scientific, Sunnyvale, Calif.) column. Cells were centrifuged, resuspended in 30% percoll, loaded on a 40% percoll gradient, and centrifuged for 25 min at 1400×g. The pellet consisted of small resting T cells, which were >98% $CD2^+$, $CD3^+$. The interphase, containing LGL, was incubated with saturating concentrations of anti-CDI4 (Leu-M3), anti-CD3 (Leu-4), anti-CD4 (Leu-3a), anti-CD19 (Leu-12) and anti-CD20 (Leu16) mAb for 30 min. at 4° C., washed, and incubated with sheep anti-mouse IgG-coated magnetic beads (Dynabeads M450, Dynal A. S., Oslo, Norway) at a bead to cell ratio of 20:1. The mixture was incubated with gentle shaking for 30 min. at 4° C., and rosetted cells were removed with the magnetic particle concentrator according to the manufacturer's recommendations. The resulting population was 80–90% $CD16^+$, $CD56^+$.

B cells were isolated from mononuclear cells obtained from spleens of healthy donors by centrifugation through Ficoll Hypaque. Mononuclear cells were incubated with saturating concentrations of anti-CD2 (Leu5b), anti-CD3 (Leu-4), anti-CD4 (Leu-3a) anti-CD8 (Leu-2a), anti-CD14 (Leu-M3), anti-CD16 (Leu-11a) and anti-CD56. (Leu-19) mAb for 30 min at 4° C. and subjected to negative selection with magnetic beads as described above. The resulting population was >95% CD19+, CD20+.

Structure and expression of FLAG-hIL-10

A signal sequence and FLAG peptide sequence (30) were fused to the hIL-10 coding region at the N-terminus by patch PCR as described previously (23, 31): MAL . . . ARP (signal peptide sequence)—DYK . . . DDK (FLAG)—SPG . . . SENS . . . (hIL-10). The PCR product was cloned in the pcDSRα296 vector (32). Transient expression of FLAG-hIL-10 in COS7 cells was analyzed by $^{35}$S-methionine labelling/SDS PAGE (19), and by ELISA with anti-FLAG Mab M1 as the coating Mab and anti-hIL-10 as the detecting Mab (10, 23). Biological activities of FLAG-hIL-10 in COS7 supernatants were assessed in the CSIF assay (4, 5) and by costimulation of proliferation of mouse MC/9 mast cells in the presence of IL-4 (16, 18).

Detection of hiL-10R (a) FACS. Human cells and cell lines were incubated with 30–60 nM FLAG-hIL-10 in FACS buffer (Hanks Balanced Salt Solution (HBSS) supplemented with 3% FCS, 0.02% $NaN_3$) on ice for 1 hr. After staining, cells were pelleted and resuspended directly in cross-linking solution (DPBS/50 mM Hepes pH 8.3/0.2 mM $BS^3$ (Pierce Chemical Co., Rockford, Ill.)) for 30 minutes on ice. Excess $BS^3$ was quenched by adding Tris-HCl pH 8.0 to a final concentration of 50 mM. Cells were then washed twice in FACS buffer, incubated with 10 μg/ml biotinylated M1 Mab for 30 minutes on ice, then washed and incubated with SA-PE prior to FACS analysis as described (23).

To determine specificity of binding, COS7 or Ba/F3 cells expressing recombinant hIL-10R were incubated with 5 nM FLAG-hIL-10 in the presence or absence of a 100-fold molar excess of the competing cytokine, then subjected to further treatment and FACS analysis as above.

(b) Ligand binding. Transfected Ba/F3 cells expressing recombinant hIL-10R (see below) were incubated as triplicate samples ($10^6$ cells/sample) with $^{125}$I-hIL-10 at concentrations of 4–530 pM, in the presence or absence of 150 nM purified hIL-10 for 4 hr at 4° C. in RPMI1640, 2% BSA, 0.02% sodium azide, and then pelleted through a mixture of phthalate oils as described (23, 33, 34). The, cell pellet and supernatant were assessed for bound and free 125I cpm, respectively. Nonspecific binding cpm as measured in samples containing unlabelled hIL-10 competitor were subtracted to obtain specific binding cpm. Values for Kd and receptor number were obtained by Scatchard analysis (23, 33, 34).

(c) SDS-PAGE. The detailed procedure was described previously (23). Briefly, hIL-10R expressed by BJAB cells and hIL-10R cDNA-transfected COS7 cells was bound to $^{35}$S-methionine labelled FLAG-hIL-10 and cross-linked with sulfo-EGS (Pierce Chemical Co., Rockford, Ill.), followed by lysis in a buffer containing 1% Triton X-100 and a cocktail of protease inhibitors. The cleared lysate or the anti-FLAG Mab M2 immunoprecipitates were analyzed by 7.5% SDS-PAGE and autoradiography.

cDNA library construction

A BJAB cDNA library of approximately 10independent clones was prepared using the Super Script Plasmid System (BRL, Gaithersburg, Md.), except that BstXI adaptors instead of SalI adaptors were used. Double-stranded cDNA was size-selected on Chromaspin-1000 columns (Clontech, Palo Alto, Calif.), ligated into the expression vector pJFE14 (35), and transformed into *E. coli* DH10B cells.

Expression cloning of hIL-10R cDNA

Screening of the BJAB cDNA library was performed by several rounds of transfection and selection by panning (23, 36–38). In the first round, 4.5×$10^7$ COS7 cells were transfected with the BJAB cDNA library by electroporation. Three days after transfection, COS7 cells were harvested from the plates with 0.5 mM EDTA/0.02% $NaN_3$ and incubated with 30–60 nM FLAG-hIL-10 for 1 h on ice, followed by cross-linking with $BS^3$. COS7 cells expressing hIL-10R were then selected on plates coated with anti-FLAG Mabs M1 and M2. Plasmid DNA recovered from the selected cells was transformed into *E. coli* DH10B cells by electroporation and reintroduced into COS7 cells by spheroplast fusion for subsequent rounds of panning. After three cycles of panning, DNAs were prepared from randomly picked *E. coli* colonies and digested with XhoI and NotI to release cDNA inserts. Approximately one third of the clones analyzed had the same insert, and two of them (pYLB5, pYLB6) were chosen for analysis by expression in COS7 cells.

A XbaI/PvuII DNA fragment from the 5'-end of pYLB5 was used as a probe to isolate another clone (pSW8.1) from the original BJAB cDNA library. The DNA sequence of hIL-10R was determined by using pSW8.1 subclones as templates as described (18) and analyzed using software from Intelligenetics, Inc. (Mountain View, Calif.).

Analysis of hIL-10R mRNA expression hIL-10R mRNA expression in various human tissues was tested by probing human multiple-tissue northern blots (Clontech, Palo Alto, Calif.) with the complete hIL-10R cDNA (XhoI-NotI fragment) according to the manufacturer's instructions. Expression of hIL-10R mRNA in human cells/cell lines was detected by RNA blot hybridization as described (18). Filters were probed first with hIL-10R and subsequently with human β-actin (Clontech, Palo Alto, Calif.). hIL-10R RNA blots required 24–72 hr exposure times; β-actin required 2–3 hr. Quantitative measurements of hIL-10R hybridization signals were made on a Phosphoramger (Molecular Dynamics, Sunnyvale, Calif.) with reference to the β-actin hybridization signal as a standard. After subtraction of background from the hIL-10R and β-actin signals, the ratio of their intensities was calculated for each sample for purposes of comparison.

Expression of hIL-10R in transfected Ba/F3 cells

The hIL-10R cDNA pSW8.1 was transfected into Ba/F3 cells along with a plasmid encoding neomycin resistance as described (23, 28). G418-resistant hIL-10R-expressing cells (Ba8.1) were twice sorted for hIL-10R expression and expanded in culture (23). Ba/F3 and Ba8.1 cells were tested for binding to various concentrations of FLAG-hIL-10 and analyzed by FACS (23). Their responsiveness to hIL-10 and mIL-10 was tested as follows (23): 2000–5000 cells were cultured with various amounts of IL-10 in a total volume of 100 μl in 96-well culture plates for 48 hr at 37° C. A 10 μl aliquot of Alamar Blue dye solution (Alamar Biosciences, Sacramento, Calif.) was added to each well. After 12–14 hr incubation, the response was determined by measuring $A_{570}$–$A_{600}$.

Chromosomal localization of the hIL-10R gene

The chromosomal location of the hIL-10R gene was determined by hybridization to MspI digests of genomic DNA from a panel of human-hamster somatic cell hybrids on a filter purchased from BIOS Corporation (New Haven, Conn.). The full-length hIL-10R cDNA was used as a probe.

RESULTS

Construction and expression of FLAG-hIL-10

A 21 amino acid leader sequence and 8 amino acid FLAG sequence were fused to the N-terminus of hIL-10 as described previously for mIL-10 (23). The PCR product was cloned in the expression vector pcDSRα296 and expressed in COS7 cells. The expression level of FLAG-hIL-10 was the same as hIL-10, and its biological activities were indistinguishable from hIL-10 as determined in CSIF and MC/9 bioassays (data not shown). Furthermore, anti-FLAG Mab could detect epitope-tagged FLAG-hIL-10 in ELISA but did not block the biological activities of FLAG-hIL-10 when added to CSIF or MC/9 bioassays in vitro (data not shown).

Figure 20A:
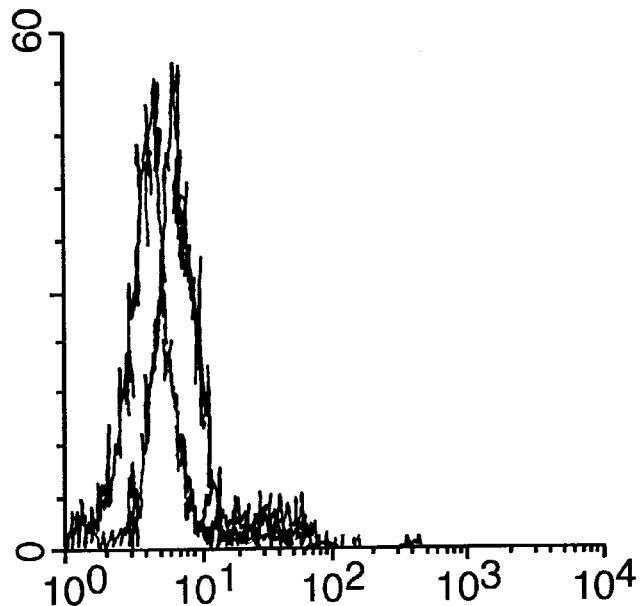
FIGS. 20A–20E, show detection of hIL-10R on human Burkitt Lymphoma cell line (BJAB), and transfected COS7 cells expressing hIL-10R. FACS histograms are shown for BJAB (FIG. 20A) and for COS7 cells transfected with pYLB5 (FIG. 20B), and compared to results obtained in the presence of a 100-fold molar excess hIL-10; each panel shows detection of FLAG-hIL-10 bound to hIL-10R (right histogram) reduced to background by competition with 100-fold molar excess of hIL-10 (left histogram). Immunofluorescence micrographs of COS7 cells expressing hIL-10R (the same cells as in FIG. 20B) in the absence (FIG. 20C) and presence (FIG. 20D) of hIL-10 competitor and in the presence of mIL-10 competitor (FIG. 20E) are also shown.

Detection of hIL-10R on BJAB cells hIL-10 responsive cells, which included human adherent cells from PBMC from healthy human donors (7) and human cell lines were tested for their ability to bind FLAG-hIL-10. Cells were incubated with various concentrations of FLAG-hIL-10, followed by treatment with a cross-linking reagent, and FLAG-hIL-10 bound to cells was detected by biotinylated anti-FLAG Mab and SA-PE for FACS analysis (23). A Burkitt lymphoma cell line, BJAB, was found to give reproducible but low levels of specific FLAG-hIL-10 binding which were reduced to background by excess hIL-10 as competitor (FIG. 20A). The level of this specific staining increased when BJAB cells were transferred to fresh culture medium and maintained at low cell density 14–16 hrs before analysis, probably because production of low but detectable amounts of hIL-10 by BJAB cells themselves leads to substantial occupancy of hIL-10R by endogenous hIL-10. This observation suggested that only "unoccupied" hIL-10 receptor could be readily detected by FLAG-hIL-10, or alternatively that hIL-10R may undergo ligand-induced down-modulation on BJAB cells. A cDNA library was made from these cells.

Isolation of hIL-10R cDNA clones from the BJAB cDNA library

A cDNA library of $10^7$ recombinants was prepared from mRNA isolated from BJAB cells. Size-selected double-stranded cDNA was cloned into the expression vector pJFE14. cDNA library DNA was introduced into COS7 cells by electroporation. After 72 hr, cells expressing hIL-10R were then selected by panning on anti-FLAG coated plates (see Materials and Methods). Plasmid DNA recovered from the selected cells was transformed into *E. coli* DH10B cells by electroporation and reintroduced into COS7 cells by spheroplast fusion for two further rounds of selection, after which the recovered plasmid DNA was highly enriched for hIL-10R cDNAs: seven out of 20 clones were found to have the same insert of 3.6 kb Two of the clones (pYLB5, pYLB6) were transfected into COS7 cells and the resulting transfectants were analyzed for hIL-10R expression.

Expression of hIL-10R clones

Figure 20B:
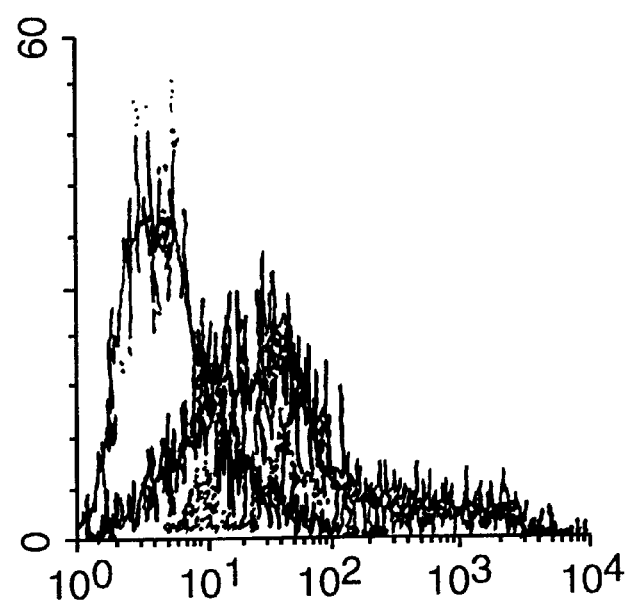
Figure 20C:
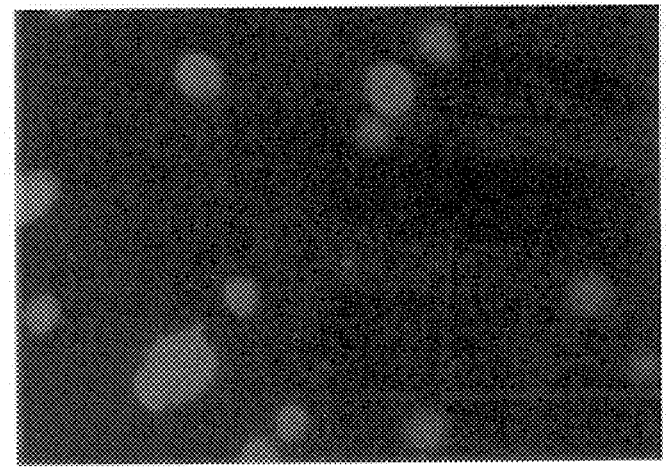
Figure 20D:
Figure 21:
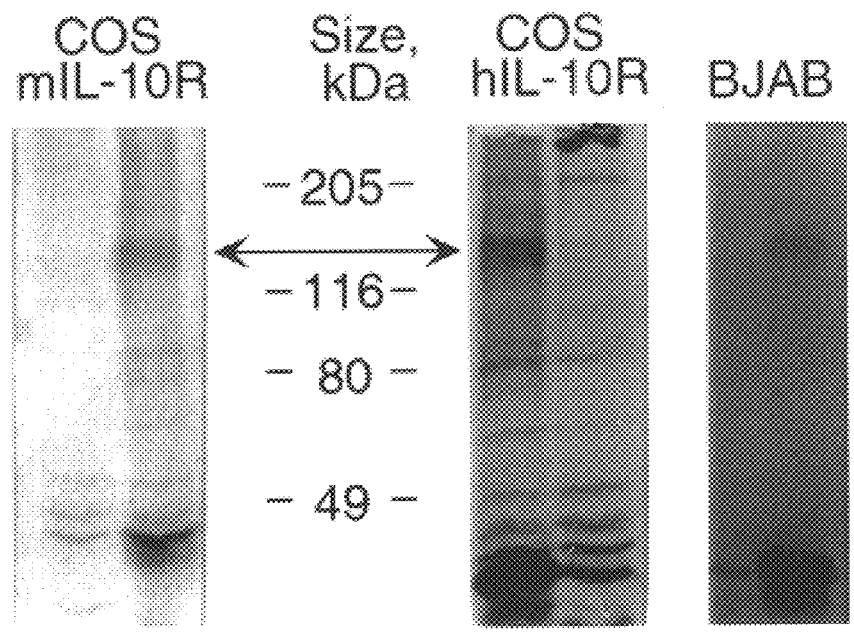
FIG. 21. Detection of hIL-10R expression by BJAB cells and pSW8.1-transfected COS7 cells by cross-linking to ³⁵S-labelled FLAG-hIL-10. The BJAB samples are immunoprecipitates and COS7 samples are cleared lysates. The hIL-10R and mIL-10R cross-linked to FLAG-hIL-10 or FLAG-mIL-10 (23), respectively, are indicated by arrows. The prominent bands near the 49 kDa standard are cross-linked FLAG-hIL-10 and FLAG-mIL-10 homodimers, as noted earlier (23).

COS7 cells transfected with candidate hIL10R cDNA clones were assessed for ability to bind FLAG-hIL-10. FIG. 20B shows specific staining of COS7 cells expressing the pYLB5 clone, which was reduced to background in the presence of excess hIL-10 (FIG. 20C) but not mIL-10 (data not shown). Fluorescence microscopy of pYLB5-transfected COS7 cells also showed specific staining with FLAG-hIL-10 which was not inhibited by excess mIL-10 (FIG. 20C, D, E). In contrast to BJAB cells, use of the cross-linking reagent was not required for detection of hIL-10R expressed on COS7 cells, probably because of increased avidity for ligand due to higher hIL-10R density.

hIL-10R was visualized as a 120–140 kDa protein by cross-linking $^{35}$S-labelled FLAG-hIL-10 bound to hIL-10R expressed on both BJAB and hIL10R cDNA-transfected COS7 cells (FIG. 21). This protein is the same size as mIL-10R detected on mIL-10R-transfected COS7 cells (23) (FIG. 21). No such protein species was detected in mock-transfected COS7 cells (data not shown). Subtraction of the molecular weight of one (~20 kDa) or two (~40 kDa) FLAG-hIL-10 peptide chains gave the estimated size of hIL-10R as 90–110 kDa.

Sequence analysis of hIL-10R cDNA

To avoid possible mutations of cDNAs during serial passages in COS7 cells during cDNA library screening; a XbaI-PvuII fragment from the 5'-end of pYLB5 was used as a hybridization probe to isolate another clone from the original BJAB cDNA library. (pSW8.1), which was then used for DNA sequence analysis. The complete nucleotide sequence of the 3647 bp insert of clone pSW8.1 is shown in Table 2. The DNA sequence contains an ORF encoding a protein of 578 amino acids, including a putative signal peptide sequence of 21 amino acids (39), a 215 amino acid extra-cellular domain, a transmembrane segment of 25 amino acids, and a cytoplasmic domain of 317 amino acids. The calculated molecular mass of hIL-10R from the deduced amino acid sequence is ~61 kDa, in contrast to the observed size of 90–110 kDa (FIG. 21). This suggested that, like mIL-10R (23), and as observed with other cytokine receptors (40), hIL-10R may be glycosylated at one or more of the six potential sites identified in the extracellular domain (Table 2 ). The nucleotide sequence of pSW8.1 is 70% homologous to the mIL-10R cDNA in the 5'-untranslated and predicted protein-coding regions. The predicted amino acid sequences of hIL-10R and mIL-10R are 60% identical; if chemically similar amino acids are included, the homology—"similarity"—is ~73% (see Table 2).

IL10 was predicted to be a member of the four α-helix bundle cytokine family (41), and most receptors for these cytokines (for example, IL-2; -3, -4, -5, -6, and IL-7; G-CSF; GM-CSF) are in the class I group of the cytokine receptor superfamily (42). However, like mIL-10R, the structure of hIL-10R is more similar to the smaller group of class II CRs which includes interferon receptors (IFNR), a viral IFNR homolog, and tissue factor (42–44). The extracellular portion of hIL-10R may be considered as two homologous segments of ~110 amino acids that are similar to the size of the immunoglobin-like ligand binding domains of the growth hormone receptor (GHR) (42, 45). The first class II CR domain features two conserved tryptophans and the second cysteine pair of class I CRs; however hIL-10R, unlike mIL-10R, lacks this cysteine pair (Table 2).

Functional expression of hIL-10R in Ba/F3 cells

Figure 22A:
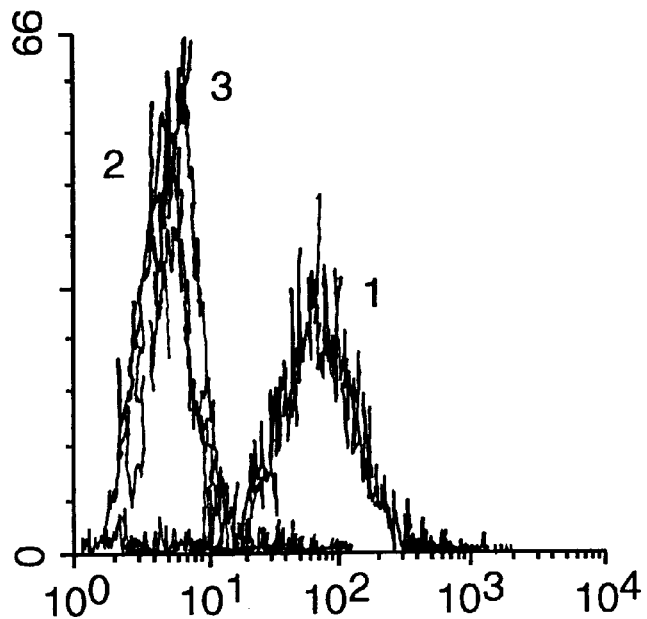
FIGS. 22A–22D Expression of hIL-10R in transfected Ba/F3 cells and their response to mIL-10, hIL-10.
Figure 22B:
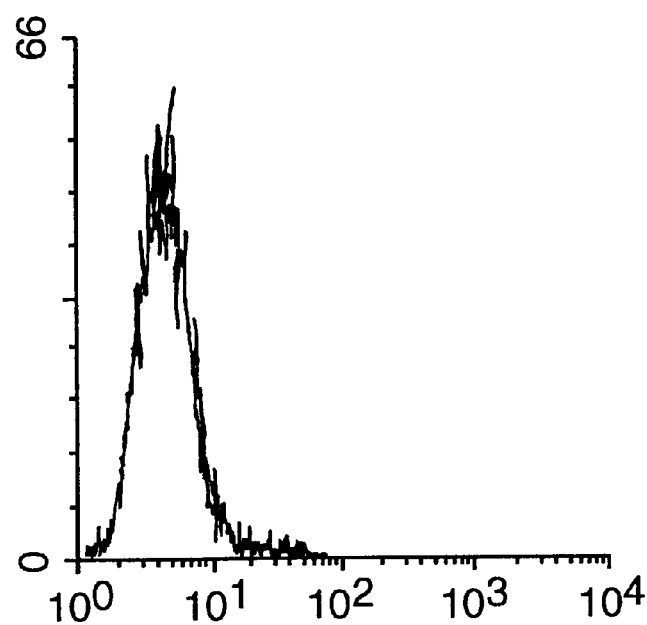

The hIL-10R cDNA pSW8.1 was transfected along with a plasmid encoding a neomycin resistance gene into a mouse pro-B cell line, Ba/F3, which expresses little or no mIL-10R (23). G418-resistant cells expressing recombinant hIL-10R (Ba8.1) were isolated by FACS (FIGS. 22A, B), expanded in culture, and tested for ability to bind $^{125}$I-hIL-10 (Scatchard analysis, FIG. 22C) and respond to either hIL-10 or mIL-10 (proliferation assay; FIG. 22D): The negative control Neo plasmid-transfected Ba/F3 cell line (BaF-Neo) neither binds hIL-10 (FIG. 22B), nor responds to hIL-10 in the proliferation assay (FIG. 22D).

Figure 22C:
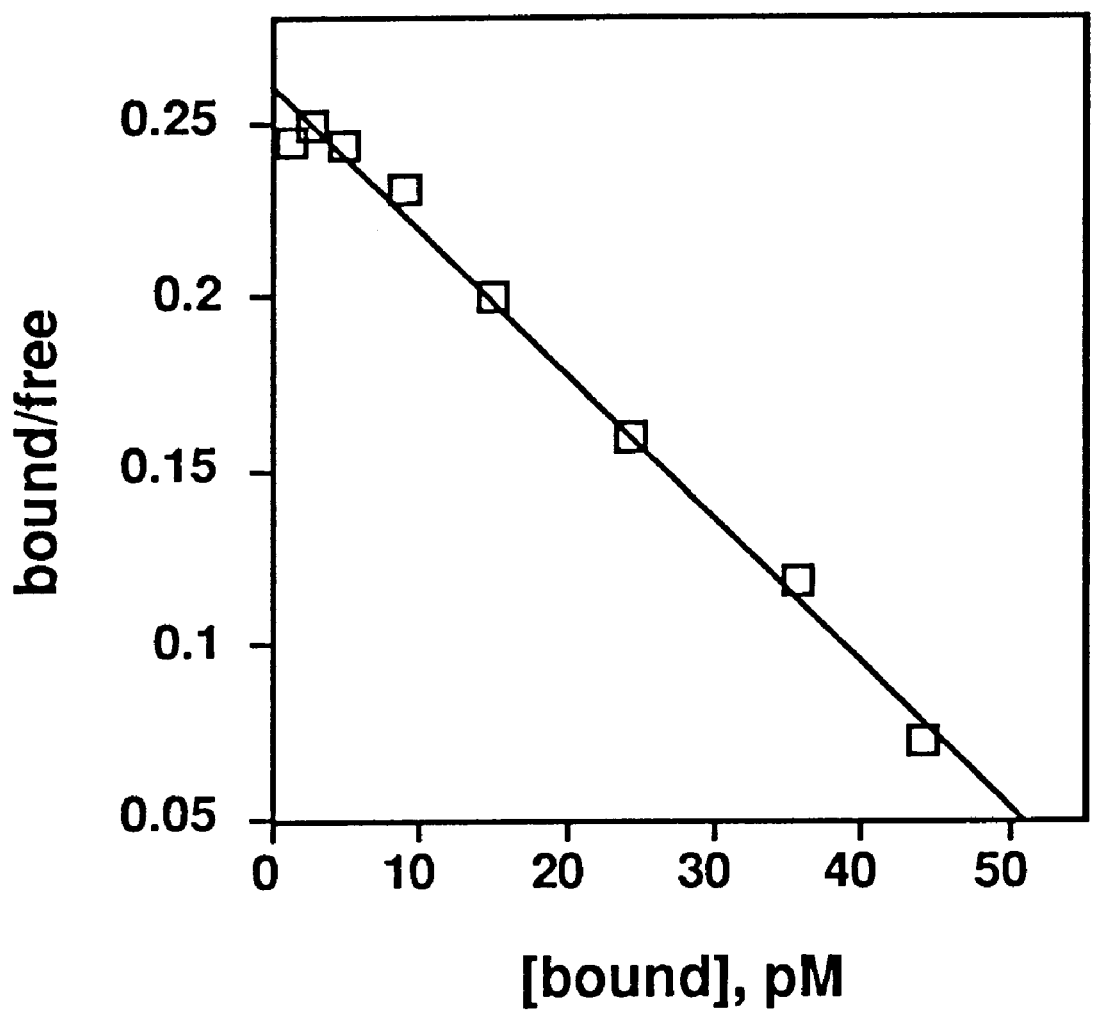
Figure 22D:
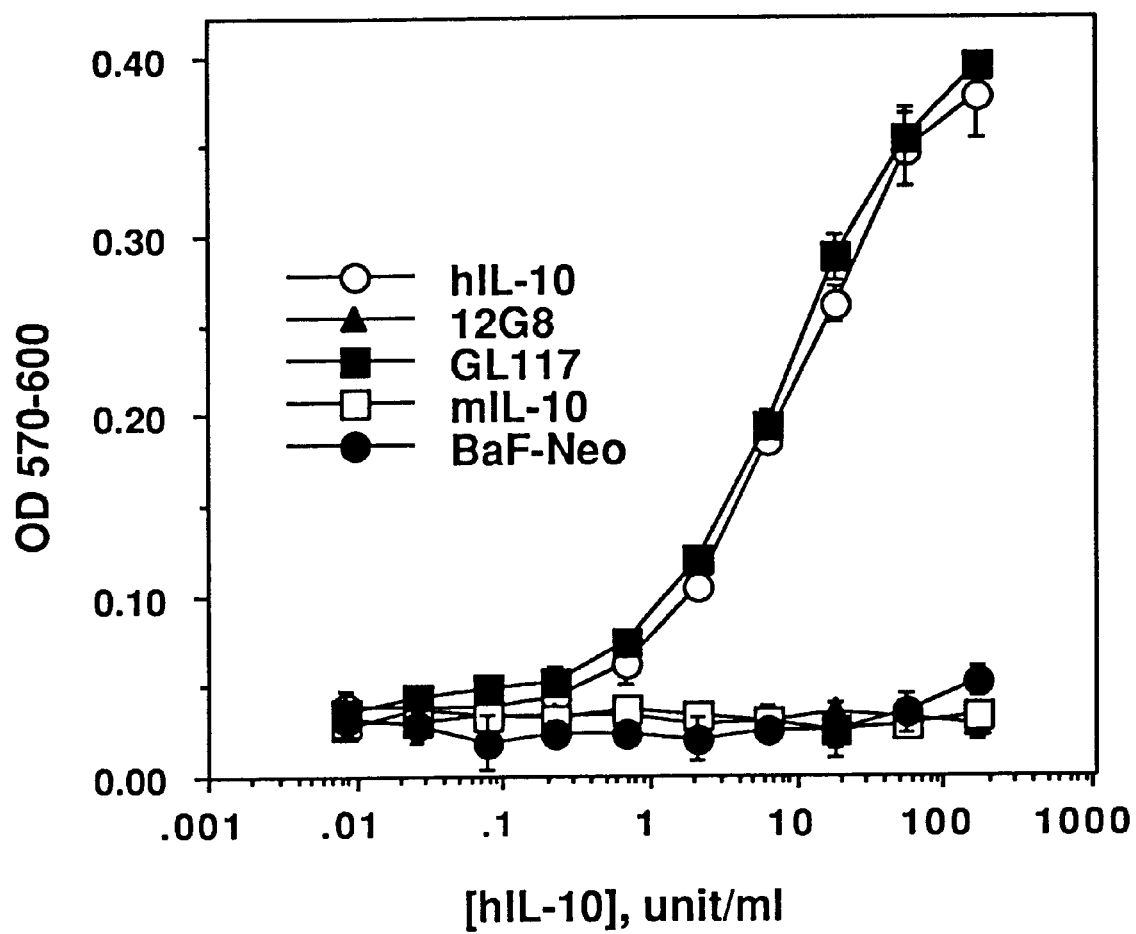

Ba8.1 cells expressed about 7000 receptors per cell and bound 125I-hIL-10 with a Kd of 200–250 pM, a relatively high affinity among CR (FIG. 22C). This is similar to the Kd of 50–200 pM of hIL-10R reported by Tan et al. for the human JY cell line (46), and somewhat higher than ~70 pM reported for recombinant mIL-10R (23). This value reflects a relatively high affinity compared to other CRs (47), which have Kd values ranging from 30 pM for the high-affinity erythropoietin receptor to 120 nM for the low-affinity hIL-3 receptor.

Figure 20E:
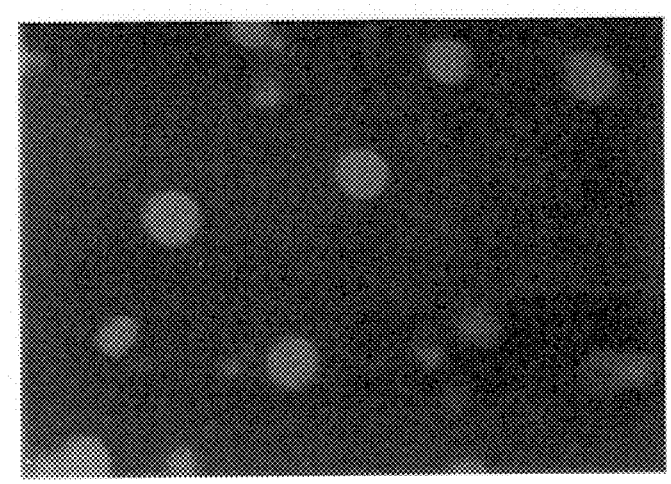

Neither BaF-Neo nor parental Ba/F3 cells gave a proliferative response to hIL-10 or mIL-10, but Ba8.1 cells, like Ba/F3 cells expressing recombinant mIL-10R (23), responded to hIL-10 specifically in a dose-dependent fashion in an assay measuring proliferation and viability (FIG. 22D). This response was inhibited by the neutralizing anti-hIL-10 Mab 12G8 (FIG. 22D) and thus was specific for hIL-10. Ba8.1 cells did not respond to mIL-10, consistent with observations that mIL-10 is species-specific (1) and does not bind to hIL-10R (FIG. 20E). Moreover, binding of FLAG-hIL-10 to hIL-10R expressed on Ba8.1 cells was not inhibited by 100-fold molar excess of hIL-1, -2, -3, -4, and hIL-5; hIL-7, hIL-13, hGMCSF, hIFNα, hIFNγ, hTNFα, mIL-10, or vIL-10 (data not shown).

hIL-10R mRNA expression

Figure 23A:
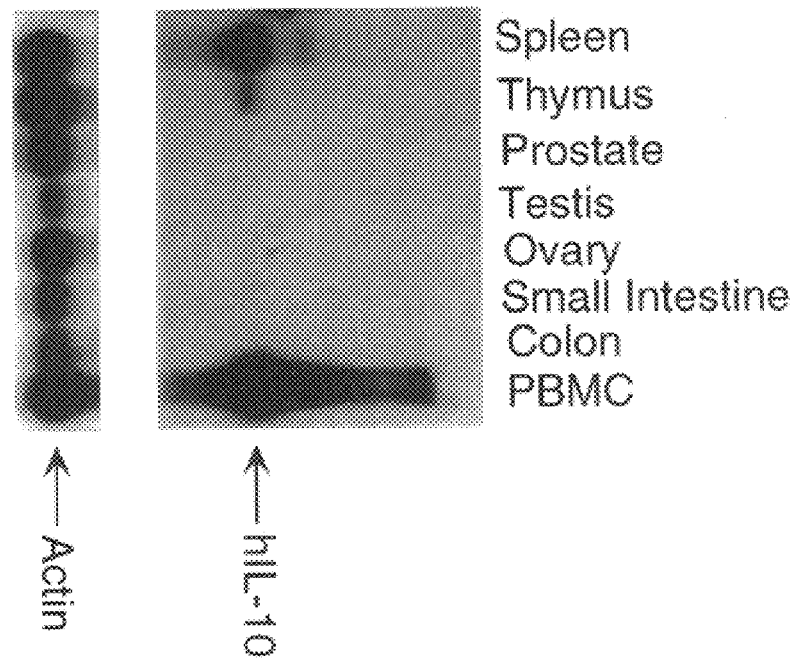
FIGS. 23A–23C hIL-10R mRNA expression in various human tissues and cells. The 3.6 kb hIL-10R mRNA (upper band) and actin mRNA (lower band) are shown.

RNA blot analysis revealed a 3.6 kb hIL-10R mRNA species in a number of human tissues including spleen, thymus, and PBMC (FIG. 23A). Non-hemopoietic tissues revealed only faint hybridization to the hIL-10R probe, including also pancreas, skeletal muscle, brain, heart, and kidney (not shown). Placenta, lung, and liver showed intermediate levels of hIL-10R mRNA. Possibly, much of the signal detected in these samples could be due to contaminating blood cells present during isolation of the tissues.

Figure 23B:
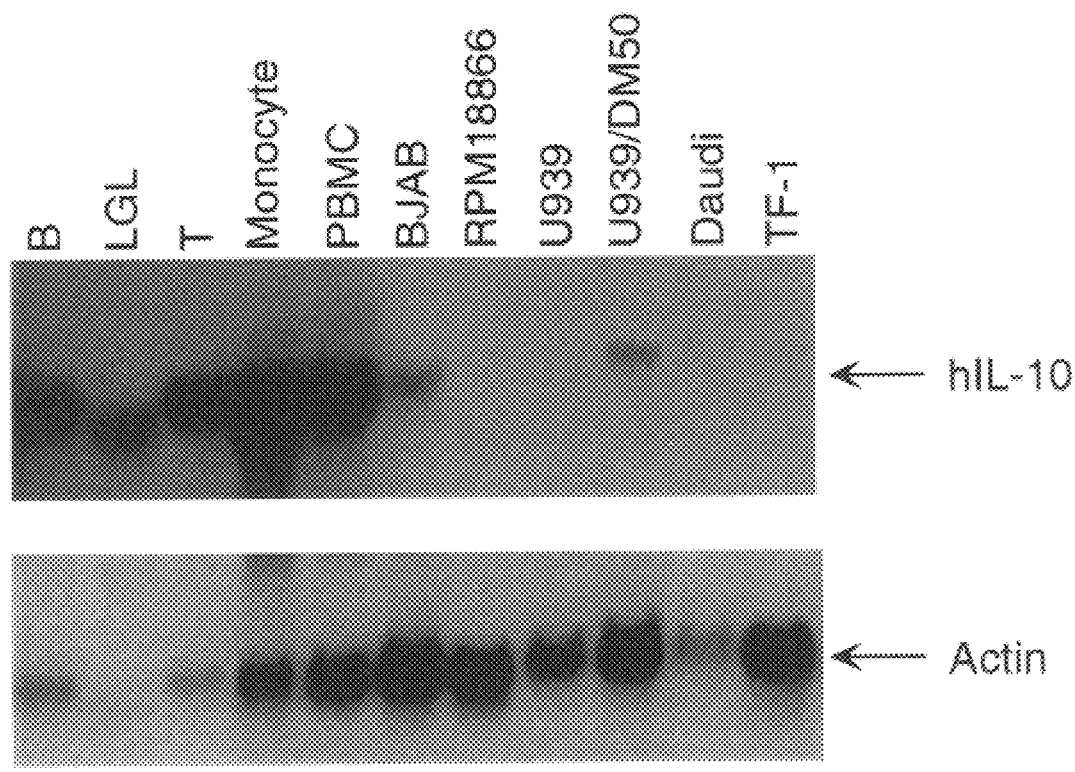
Figure 23C:
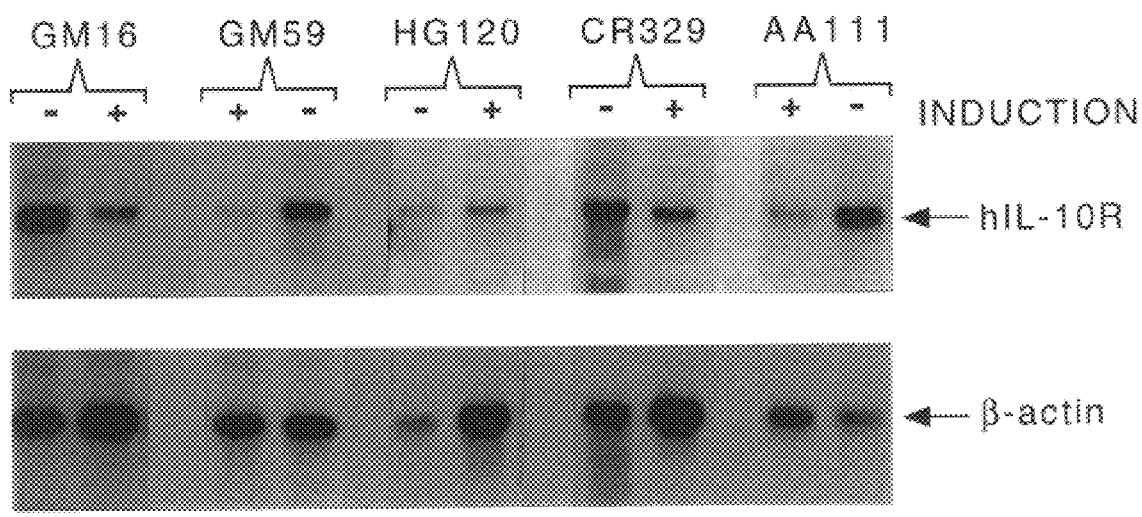

Human cells which express hIL-10R mRNA include monocytes, B cells, LGL, and T cells isolated from fresh PBMC or spleen (FIG. 23B). Cell lines in which the 3.6 kb, mRNA was detected were BJAB, DMSO-differentiated U937 cells (FIG. 23B), NK cell lines (data not shown), and various cloned human T cell lines (48) (FIG. 23C). All cell populations and cell lines known to respond to IL-10—B cells (12), monocytes/macrophages and DMSO-differentiated U937 cells (6, 10), and T cells and T cell clones (48)—expressed readily detectable levels of hIL-10R mRNA, as also observed for mIL-10R (23). Activation of human T cell clones of several phenotypes, including Tho-like CD8+clones (GM16, GM59) and Th1-like (CR239), Th2-like (AA111), and Tho-like (HG120) CD4+clones, by anti-CD3 and TPA was associated consistently with down-regulation of the level of hIL-10R mRNA detected in the cells (FIG. 23C and data not shown). With reference to β-actin mRNA as standard, the decrease in hIL-10R mRNA ranged from 2- to 10-fold in the samples examined, with the CD8+Tho clones tending to exhibit the more marked decreases in hIL-10R mRNA level.

Little or no hIL-10R mRNA was detected in RPMI8866, Daudi, undifferentiated U937, and TF1 cells on an RNA blot by autoradiogram. Furthermore, TF-1 cells, which express receptors for and respond to several human cytokines, including IL-1, IL-3, IL-4, IL-5, IL-6, GM-CSF, and erythropoietin (49), did not exhibit a detectable response to hIL-10 (YL and KWM, unpublished). Analysis of the hIL-10R and β-actin RNA blots using the phosphorimager suggested that expression of hIL-10R mRNA by these cell lines was at least several hundred-fold below the level observed in the hIL-10R+populations.

Chromosomal localization of the hIL-10R gene

We determined the chromosomal location of the hIL-10R gene by hybridizing the hIL-10R cDNA probe to MspI digests of DNAs from a human-hamster hybrid cell line panel. The hIL-10R probe hybridizes prominently to a MspI fragment of ~3.2 kb, along with several smaller, less intense bands in human genomic DNA. Only cell line 1049, which contained human chromosomes 5 and 11, was positive when hybridized with hIL-10R cDNA (data not shown). However, all other cell lines containing chromosome 5 did not hybridize to the hIL-10R cDNA probe (data not shown). Therefore, we concluded that the hIL-10R gene was located on chromosome 11.

References

1. Moore, K. W., A. O'Garra, R. de Waal Malefyt, P. Vieira, and T. R. Mosmann. 1993. Interleukin-10. Ann. Rev. Immunol. 11:165.

2. Enk, A. H., and S. I. Katz. 1992. Identification and induction of keratinocyte-derived IL-10. J. Immunol. 149:92.

3. Rivas, J. M., and S. E. Ullrich. 1992. Systemic suppression of delayed-type hypersensitivity by supernatants from UV-irradiated keratinocytes: an essential role for keratinocyte-derived IL-10. J. Immunol. 149:3865.

4. Fiorentino, D. F., M. W. Bond, and T. R. Mosmann. 1989. Two types of mouse helper T cell. IV. Th2 clones secrete a factor that inhibits cytokine production by Th1 clones. J. Exp. Med. 170:2081.

5. Fiorentirio, D. F., A. Zlotnik, P. Vieira, T. R. Mosmann, M. Howard, K. W. Moore, and A. O'Garra. 1991. IL-10 acts on the antigen-presenting cell to inhibit cytokine production by Th1 cells. J. Immunol. 146:3444.

6. de Waal Malefyt, R., J. Haanen, H. Spits, M.-G. Roncarolo, A. te Velde, C. Figdor, K. Johnson, R. Kastelein, H. Yssel, and J. E. de Vries. 1991. IL-10 and viral IL-10 strongly reduce antigen-specific human T cell proliferation by diminishing the antigen-presenting capacity of monocytes via downregulation of class II MHC expression. J. Exp. Med. 174:915.

7. Hsu, D.-H., K. W. Moore, and H. Spits. 1992. Differential effects of interleukin-4 and -10 interleukin-2-induced interferon-g synthesis and lymphokine-activated killer activity. Internat. Immunol. 4:563.

8. Ralph, P., I. Nakoinz, A. Sampson-Johannes, S. Fong, D. Lowe, H.-Y. Min, and L. Lin. 1992. IL-10, T lymphocyte inhibitor of human blood cell production of IL-1 and tumor necrosis factor. J. Immunol. 148:808.

9. Bogdan, C., Y. Vodovotz, and C. Nathan. 1991. Macrophage deactivation by interleukin 10. J. Exp. Med. 174:1549.

10. de Waal Malefyt, R., J. Abrams, B. Bennett, C. Figdor, and J. de Vries. 1991. IL-10 inhibits cytokine synthesis by human monocytes: an autoregulatory role of IL-10 produced by monocytes. J. Exp. Med. 174:1209.

11. Fiorentino, D. F., A. Zlotnik, T. R. Mosmann, M. H. Howard, and A. O'Garra. 1991. IL-10 inhibits cytokine production by activated macrophages. J. Immunol. 147:3815.

12. Rousset, F., E. Garcia, T. Defrance, C. Peronne, D.-H. Hsu, R. Kastelein, K. W. Moore, and J. Banchereau. 1992. IL-10 is a potent growth and differentiation factor for activated human B lymphocytes. Proc. Natl. Acad. Sci. USA 89:1890.

13. Suda, T., A. O'Garra, I. MacNeil, M. Fischer, M. Bond, and A. Zlotnik. 1990. Identification of a novel thymocyte growth promoting factor derived from B cell lymphomas. Cell. Immunol. 129:228.

14. MacNeil, I., T. Suda, K. W. Moore, T. R. Mosmann, and A. Zlotnik. 1990. IL-10: a novel cytokine growth cofactor for mature and immature T cells. J. Immunol. 145:4167.

15. Chen, W.-F., and A. Zlotnik. 1991. Interleukin 10: A novel cytotoxic T cell differentiation factor. J. Immunol. 147:528.

16. Thompson-Snipes, L., V. Dhar, M. W. Bond, T. R. Mosmann, K. W. Moore, and D. Rennick. 1991. Interleukin-10: a novel stimulatory factor for mast cells and their progenitors. J. Exp. Med. 173:507.

17. Go, N. F., B. E. Castle, R. Barrett, R. Kastelein, W. Dang, T. R. Mosmann, K. W. Moore, and M. Howard. 1990. Interleukin 10 (IL-10), a novel B cell stimulatory factor: unresponsiveness of X chromosome-linked immunodeficiency B cells. J. Exp. Med. 172:1625.

18. Vieira, P., R. de Waal-Malefyt, M.-N. Dang, K. E. Johnson, R. Kastelein, D. F. Fiorentino, J. E. deVries, M.-G. Roncarolo, T. R. Mosmann, and K. W. Moore. 1991. Isolation and expression of human cytokine synthesis inhibitory factor (CSIF/IL10) cDNA clones: homology to Epstein-Barr virus open reading frame BCRFI. Proc. Natl. Acad. Sci. USA 88:1172.

19. Moore, K. W., P. Vieira, D. F. Fiorentino, M. L. Trounstine, T. A. Khan, and T. R. Mosmann. 1990. Homology of cytokine synthesis inhibitory factor (IL-10) to the Epstein Barr Virus gene BCRFI. Science 248:1230.

20. Rode, H.-J., W. Janssen, A. Rosen-Wolff, J. J. Bugert, P. Thein, Y. Becker, and G. Darai. 1993. The genome of equine herpesvirus type 2 harbors an interleukin-10 (IL-10)-like gene. Virus Genes 7:111.

21. Burdin, N., C. Peronne, J. Banchereau, and F. Rousset. 1993. EpsteinBarr virus transformation induces B lymphocytes to produce human interleukin-10. J. Exp. Med. 177:295.

22. Miyazaki, I., R. K. Cheung, and H.-M. Dosch. 1993. Viral interleukin 10 is crtical for the induction of B cell growth transformation by EpsteinBarr virus. J. Exp. Med. 178:439.

23. Ho, A. S.-Y., Y. Liu, T. A. Khan, D.-H. Hsu, J. F. Bazan, and K. W. Moore. 1993. A receptor for interleukin-10 is related to interferon receptors. Proc. Natl. Acad. Sci. USA in press.

24. Hsu, D.-H., R. de Waal Malefyt, D. F. Fiorentino, M.-N. Dang, P. Vieira, J. de Vries, H. Spits, T. R. Mosmann, and K. W. Moore. 1990. Expression of IL-10 activity by Epstein-Barr Virus. Protein BCRFI. Science 250:830.

25. Myers, R. F., and M. I. Siegel. 1984. The appearance of phospholipase activity in the human macrophage-like cell line U937 during dimethyl sulfoxide-induced differentiation. Biochem. Biophys. Res. Commun. 118:217.

26. Nicholson, D. W., A. Ali, M. W. Klemba, N. A. Munday, R. J. Zamboni, and A. W. Ford-Hutchinson. 1992. Human leukotriene C4 synthase expression in dimethyl sulfoxide-differentiated U937 cells. J. Biol. Chem. 267:17849.

27. Stuart, S. G., M. L. Trounstine, D. J. T. Vaux, T. Koch, C. L. Martens, I. Mellman, and K. W. Moore. 1987. Isolation and expression of cDNA clones encoding a human receptor for IgG (FcgRII). J. Exp. Med. 166:1668.

28. Kitamura, T., K. Hayashida, K. Sakamaki, T. Yokota, K.-I. Arai, and A. Miyajima. 1991. Reconstitution of functional receptors for human granulocyte/macrophage colony-stimulating factor (GM-CSF): Evidence that the protein encoded by the AIC2B cDNA is a subunit of the murine GM-CSF receptor. Proc. Natl. Acad. Sci. USA 88:5082.

29. Wilson, A. B., J. M. Harris, and R. R. A. Coombs. 1988. Interleukin-2-induced production of interferon-g by resting human T cells and large granular lymphocytes: requirement for accessory cell factors, including interleukin-1. Cell. Immunol. 113:130.

30. Hopp, T. P., K. S. Prickett, V. L. Price, R. T. Libby, C. J. March, D. P. Cerretti, D. L. Urdal, and P. J. Conlon. 1988. A short polypeptide marker sequence useful for recombinant protein identification and purification. Bio/Technology 6:1204.

31. Squinto, S. P., T. H. Aldrich, R. M. Lindsay, D. M. Morrissey, N. Panayotatos, S. M. Bianco, M. E. Furth, and G. Yancopoulos. 1990. Identification of functional receptors for ciliary neurotrophic factor on neuronal cell lines and primary neurons. Neuron 5:757.

32. Takebe, Y., M. Seiki, J.-I. Fujisawa, P. Hoy, K. Yokota, K.-I. Arai, M. Yoshida, and N. Arai. 1988. SR-alpha promoter: an efficient and versatile mammalian cDNA expression system composed of the simian virus 40 early promoter and the R-U5 segment of human T-cell leukemia virus type 1 long terminal repeat. Mol. Cell. Biol. 8:466.

33. Zurawski, S. M., J.-L. Imler, and G. Zurawski. 1990. Partial agonist/antagonist mouse interleukin-2 proteins indicate that a third component of the receptor complex functions in signal transduction. EMBO J. 9:3899.

34. Zurawski, S. M., and G. Zurawski. 1992. Receptor antagonist and selective agonist derivatives of mouse interleukin-2. EMBO J. 11:3905.

35. Elliott, J. F., G. R. Albrecht, A. Gilladoga, S. Handunetti, J. Neequaye, G. Lallinger, J. N. Minjas, and R. J. Howard. 1990. Genes for Plasmodium falciparum surface antigens cloned by expression in COS cells. Proc. Natl. Acad. Sci. USA 87:6363.

36. Aruffo, A., and B. Seed. 1987. Molecular cloning of a CD28 cDNA by a high-efficiency COS cell expression system. Proc. Natl. Acad. Sci. USA 84:8573.

37. Gollnick, S. O., M. L. Trounstine, L. C. Yamashita, M. R. Kehry, and K. W. Moore. 1990. Isolation, characterization, and expression of cDNA clones encoding the mouse Fc receptor for IgE (FceRII). J. Immunol. 144:1974.

38. Davis, S., T. H. Aldrich, D. M. Valenzuela, V. Wong, M. E. Furth, S. P. Squinto, and G. D. Yancopoulos. 1991. The receptor for ciliary neurotrophic factor. Science 253:59.

39. von Heijne, G. 1986. A new method for predicting signal sequence cleavage sites. Nucl. Acids Res. 14:4683.

40. Hershey, G. K. K., and R. D. Schreiber. 1989. Biosynthetic analysis of the human interferon-g receptor. J. Biol. Chem. 264:11981.

41. Shanafelt, A. B., A. Miyajima, T. Kitamura, and R. A. Kastelein. 1991. The amino-terminal helix of GM-CSF and IL-5 governs high-affinity binding to their receptors. EMBO J. 10:4105.

42. Bazan, J. F. 1990. Structural design and molecular evolution of a cytokine receptor superfamily. Proc. Natl. Acad. Sci. USA 87:6934.

43. Bazan, J. F. 1990. Shared architecture of hormone binding domains in type I and II interferon receptors. Cell 61:753.

44. Upton, C., K. Mossman, and G. McFadden. 1992. Encoding of a homolog of the IFN-gamma receptor by myxoma virus. Science 258:136.9.

45. de Vos, A. M., M. Ultsch, and A. A. Kossiakoff. 1992. Human growth hormone and the extracellular domain of its receptor: crystal structure of the complex. Science 255:306.

46. Tan, J. C., S. Indelicato, S. K. Narula, P. J. Zavodny, and C.-C. Chou. 1993. Characterization of interleukin-10 receptors on human and mouse cells. J. Biol. Chem. in press.

47. Miyajima, A., T. Kitamura, N. Harada, T. Yokota, and K.-I. Arai. 1992. Cytokine receptors and signal transduction. Ann. Rev. Immunol. 10:295.

48. de Waal Malefyt, R., H. Yssel, and J. E. de Vries. 1993. Direct effects of IL-10 on subsets of human CD4+T cell clones and resting T cells. J. Immunol. 150:4754.

49. Kitamura, T., F. Takaku, and A. Miyajima. 1991. IL-1 up-regulates the expression of cytokine receptors on a factor-dependent human hemopoietic cell line, TF-1. Internat. Immunol. 3:571.

50. Aguet, M., Z. Dembic, and G. Merlin. 1988. Molecular cloning and expression of the human interferon-g receptor. Cell 55:273.

51. Uze, G., G. Lutfalla, and I. Gresser. 1990. Genetic transfer of a functional human interferon-a receptor into mouse cells: cloning and expression of its cDNA. Cell 60:225.

52. Pestka, S. 1992. The interferon receptors: an unfinished story. AIDS Res. Hum. Retroviruses 8:776.

53. Miyajima, A., T. Hara, and T. Kitamura. 1992. Common subunits of cytokine receptors and the functional redundancy of cytokines. Trends Biochem. Sci. 17:378.

54. Gearing, D. P., M. R. Comeau, D. J. Friend, S. D. Gimpel, C. J. Thut, J. McGourty, K. K. Brasher, J. A. King, S. Gillis, B. Mosley, S. F. Ziegler, and D. Cosman. 1992. The IL-6 signal transducer, gp130 : an oncostatin M receptor and affinity converter for the LIF receptor. Science 255:1434.

55. Shuai, K., C. Schindler, V. R. Prezioso, and J. E. Darnell. 1992. Activation of transcription by IFN-gamma: tyrosine phosphorylation of a 91-kD DNA binding. protein. Science 258:1808.

56. Sen, G. C., and P. Lengyel. 1992. The interferon system. A bird's-eye view of its biochemistry. J. Biol. Chem. 267.5017.

All references cited herein are incorporated herein by reference to the same extent as if each individual publication or patent application was specifically and individually indicated to be incorporated by reference.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

We claim:

1. A substantially pure or recombinant protein or polypeptide having an amino acid sequence of the mature form of protein from SEQ ID NO: 2 or 4.

2. The protein or polypeptide of claim 1, which lacks:
   a) glycosylation; or
   b) phosphorylation.

3. The protein or polypeptide of claim 1, produced by expression of the coding portion of SEQ ID NO: 1 or 3.

4. A method of making an antibody which binds to an IL-10 receptor, comprising immunizing a mammal with a polypeptide of claim 1.

5. The method of claim 4, wherein said antibody binds to the extracellular domain of said IL-10 receptor.

6. A recombinant or substantially pure protein or polypeptide comprising a segment of at least 14 contiguous amino acids from SEQ ID NO: 2 or 4.

7. The protein or polypeptide of claim 6, which is a natural allelic variant of SEQ ID NO: 2 or 4.

8. The protein or polypeptide of claim 6, wherein said protein:
   a) is attached to a solid substrate; or
   b) is in a sterile composition; or
   c) is in a buffered composition.

9. The protein or polypeptide of claim 6, which.
   a) binds an IL-10 with a Kd of at least about 100 pM; or
   b) transduces a signal in a mammalian cell in response to IL-10.

10. The peptide of claim 6, wherein said peptide is an extracellular portion of a mammalian IL-10 receptor.

11. The peptide of claim 10, wherein said peptide is soluble.

12. A fusion protein comprising a polypeptide of claim 6 and a fusion partner.

13. The fusion protein of claim 12, wherein said fusion partner is a purification or detection tag.

14. The polypeptide of claim 6, wherein at least 14 contiguous amino acids is at least 18 contiguous amino acids.

15. The polypeptide of claim 14, wherein at least 18 contiguous acids is at least 24 contiguous amino acids.

16. The polypeptide of claim 6, wherein said polypeptide comprises
   a portion of SEQ ID NO: 2 or 4 sufficient to define an extracellular domain or an intracellular domain of an IL-10 receptor.

17. The polypeptide of claim 6, wherein said polypeptide is:
   a) denatured in SDS;

b) detectably labeled; or c) made by a synthetic method.

18. The polypeptide of claim 6, which is a mature protein of SEQ ID NO: 2.

19. The polypeptide of claim 6, wherein said 14 contiguous amino acids comes from:

a) residues 22 to 235 of SEQ ID NO: 2; or b) residues 22 to 238 of SEQ ID NO: 4.

20. A method of making an antibody which binds to an IL-10 receptor, comprising immunizing a mammal with a polypeptide of claim 6.

21. A recombinant or substantially pure polypeptide which:

a) binds an IL-10 ligand with a Kd of at least about 100 pM; and b) comprises at least 16 contiguous amino acids from the extracellular domain of SEQ ID NO: 2 or 4.

22. The polypeptide of claim 21 having a molecular weight of about 90–100 kD with glycosylation.

23. The polypeptide of claim 21 which is:

a) isolated from a primate; or b) a soluble extracellular domain from SEQ ID NO: 2.

* * * * *

SEQUENCE LISTING (1) GENERAL INFORMATION:

(iii) NUMBER OF SEQUENCES: 4

(2) INFORMATION FOR SEQ ID NO:1:

```
    (i) SEQUENCE CHARACTERISTICS:
        (A) LENGTH: 3632 base pairs
        (B) TYPE: nucleic acid
        (C) STRANDEDNESS: single
        (D) TOPOLOGY: linear (ii) MOLECULE TYPE: cDNA (ix) FEATURE:
         (A) NAME/KEY: CDS
         (B) LOCATION: 62..1798

(xi) SEQUENCE DESCRIPTION: SEQ ID NO:1:

AAAGAGCTGG AGGCGCGCAG GCCGGCTCCG CTCCGGCCCC GGACGATGCG GCGCGCCCAG         60

G ATG CTG CCG TGC CTC GTA GTG CTG CTG GCG GCG CTC CTC AGC CTC           106
  Met Leu Pro Cys Leu Val Val Leu Leu Ala Ala Leu Leu Ser Leu
  1               5                   10                  15

CGT CTT GGC TCA GAC GCT CAT GGG ACA GAG CTG CCC AGC CCT CCG TCT         154
Arg Leu Gly Ser Asp Ala His Gly Thr Glu Leu Pro Ser Pro Pro Ser
                20                  25                  30

GTG TGG TTT GAA GCA GAA TTT TTC CAC CAC ATC CTC CAC TGG ACA CCC         202
Val Trp Phe Glu Ala Glu Phe Phe His His Ile Leu His Trp Thr Pro
            35                  40                  45

ATC CCA AAT CAG TCT GAA AGT ACC TGC TAT GAA GTG GCG CTC CTG AGG         250
Ile Pro Asn Gln Ser Glu Ser Thr Cys Tyr Glu Val Ala Leu Leu Arg
        50                  55                  60

TAT GGA ATA GAG TCC TGG AAC TCC ATC TCC AAC TGT AGC CAG ACC CTG         298
Tyr Gly Ile Glu Ser Trp Asn Ser Ile Ser Asn Cys Ser Gln Thr Leu
    65                  70                  75

TCC TAT GAC CTT ACC GCA GTG ACC TTG GAC CTG TAC CAC AGC AAT GGC         346
Ser Tyr Asp Leu Thr Ala Val Thr Leu Asp Leu Tyr His Ser Asn Gly
80                  85                  90                  95

TAC CGG GCC AGA GTG CGG GCT GTG GAC GGC AGC CGG CAC TCC AAC TGG         394
Tyr Arg Ala Arg Val Arg Ala Val Asp Gly Ser Arg His Ser Asn Trp
                100                 105                 110

ACC GTC ACC AAC ACC CGC TTC TCT GTG GAT GAA GTG ACT CTG ACA GTT         442
Thr Val Thr Asn Thr Arg Phe Ser Val Asp Glu Val Thr Leu Thr Val
            115                 120                 125

GGC AGT GTG AAC CTA GAG ATC CAC AAT GGC TTC ATC CTC GGG AAG ATT         490
Gly Ser Val Asn Leu Glu Ile His Asn Gly Phe Ile Leu Gly Lys Ile
        130                 135                 140

CAG CTA CCC AGG CCC AAG ATG GCC CCC GCG AAT GAC ACA TAT GAA AGC         538
Gln Leu Pro Arg Pro Lys Met Ala Pro Ala Asn Asp Thr Tyr Glu Ser
145                 150                 155

ATC TTC AGT CAC TTC CGA GAG TAT GAG ATT GCC ATT CGC AAG GTG CCG         586
Ile Phe Ser His Phe Arg Glu Tyr Glu Ile Ala Ile Arg Lys Val Pro
160                 165                 170                 175

GGA AAC TTC ACG TTC ACA CAC AAG AAA GTA AAA CAT GAA AAC TTC AGC         634
Gly Asn Phe Thr Phe Thr His Lys Lys Val Lys His Glu Asn Phe Ser
                180                 185                 190

CTC CTA ACC TCT GGA GAA GTG GGA GAG TTC TGT GTC CAG GTG AAA CCA         682
Leu Leu Thr Ser Gly Glu Val Gly Glu Phe Cys Val Gln Val Lys Pro
            195                 200                 205

TCT GTC GCT TCC CGA AGT AAC AAG GGG ATG TGG TCT AAA GAG GAG TGC         730
Ser Val Ala Ser Arg Ser Asn Lys Gly Met Trp Ser Lys Glu Glu Cys
        210                 215                 220

ATC TCC CTC ACC AGG CAG TAT TTC ACC GTG ACC AAC GTC ATC ATC TTC         778
Ile Ser Leu Thr Arg Gln Tyr Phe Thr Val Thr Asn Val Ile Ile Phe
225                 230                 235

TTT GCC TTT GTC CTG CTG CTC TCC GGA GCC CTC GCC TAC TGC CTG GCC         826
Phe Ala Phe Val Leu Leu Leu Ser Gly Ala Leu Ala Tyr Cys Leu Ala
240                 245                 250                 255
```

| | |
|---|---|
| CTC CAG CTG TAT GTG CGG CGC CGA AAG AAG CTA CCC AGT GTC CTG CTC<br>Leu Gln Leu Tyr Val Arg Arg Arg Lys Lys Leu Pro Ser Val Leu Leu<br>                 260                              265                    270 | 874 |
| TTC AAG AAG CCC AGC CCC TTC ATC TTC ATC AGC CAG CGT CCC TCC CCA<br>Phe Lys Lys Pro Ser Pro Phe Ile Phe Ile Ser Gln Arg Pro Ser Pro<br>        275                       280                    285 | 922 |
| GAG ACC CAA GAC ACC ATC CAC CCG CTT GAT GAG GAG GCC TTT TTG AAG<br>Glu Thr Gln Asp Thr Ile His Pro Leu Asp Glu Glu Ala Phe Leu Lys<br>              290                       295                  300 | 970 |
| GTG TCC CCA GAG CTG AAG AAC TTG GAC CTG CAC GGC AGC ACA GAC AGT<br>Val Ser Pro Glu Leu Lys Asn Leu Asp Leu His Gly Ser Thr Asp Ser<br>305                  310                       315 | 1018 |
| GGC TTT GGC AGC ACC AAG CCA TCC CTG CAG ACT GAA GAG CCC CAG TTC<br>Gly Phe Gly Ser Thr Lys Pro Ser Leu Gln Thr Glu Glu Pro Gln Phe<br>320                  325                       330                  335 | 1066 |
| CTC CTC CCT GAC CCT CAC CCC CAG GCT GAC AGA ACG CTG GGA AAC GGG<br>Leu Leu Pro Asp Pro His Pro Gln Ala Asp Arg Thr Leu Gly Asn Gly<br>                 340                             345                  350 | 1114 |
| GAG CCC CCT GTG CTG GGG GAC AGC TGC AGT AGT GGC AGC AGC AAT AGC<br>Glu Pro Pro Val Leu Gly Asp Ser Cys Ser Ser Gly Ser Ser Asn Ser<br>                355                       360                       365 | 1162 |
| ACA GAC AGC GGG ATC TGC CTG CAG GAG CCC AGC CTG AGC CCC AGC ACA<br>Thr Asp Ser Gly Ile Cys Leu Gln Glu Pro Ser Leu Ser Pro Ser Thr<br>        370                       375                    380 | 1210 |
| GGG CCC ACC TGG GAG CAA CAG GTG GGG AGC AAC AGC AGG GGC CAG GAT<br>Gly Pro Thr Trp Glu Gln Gln Val Gly Ser Asn Ser Arg Gly Gln Asp<br>385                  390                       395 | 1258 |
| GAC AGT GGC ATT GAC TTA GTT CAA AAC TCT GAG GGC CGG GCT GGG GAC<br>Asp Ser Gly Ile Asp Leu Val Gln Asn Ser Glu Gly Arg Ala Gly Asp<br>400                  405                       410                  415 | 1306 |
| ACA CAG GGT GGC TCG GCC TTG GGC CAC CAC AGT CCC CCG GAG CCT GAG<br>Thr Gln Gly Gly Ser Ala Leu Gly His His Ser Pro Pro Glu Pro Glu<br>                 420                       425                        430 | 1354 |
| GTG CCT GGG GAA GAA GAC CCA GCT GCT GTG GCA TTC CAG GGT TAC CTG<br>Val Pro Gly Glu Glu Asp Pro Ala Ala Val Ala Phe Gln Gly Tyr Leu<br>                435                       440                       445 | 1402 |
| AGG CAG ACC AGA TGT GCT GAA GAG AAG GCA ACC AAG ACA GGC TGC CTG<br>Arg Gln Thr Arg Cys Ala Glu Glu Lys Ala Thr Lys Thr Gly Cys Leu<br>        450                       455                    460 | 1450 |
| GAG GAA GAA TCG CCC TTG ACA GAT GGC CTT GGC CCC AAA TTC GGG AGA<br>Glu Glu Glu Ser Pro Leu Thr Asp Gly Leu Gly Pro Lys Phe Gly Arg<br>465                  470                       475 | 1498 |
| TGC CTG GTT GAT GAG GCA GGC TTG CAT CCA CCA GCC CTG GCC AAG GGC<br>Cys Leu Val Asp Glu Ala Gly Leu His Pro Pro Ala Leu Ala Lys Gly<br>480                  485                       490                  495 | 1546 |
| TAT TTG AAA CAG GAT CCT CTA GAA ATG ACT CTG GCT TCC TCA GGG GCC<br>Tyr Leu Lys Gln Asp Pro Leu Glu Met Thr Leu Ala Ser Ser Gly Ala<br>                500                       505                    510 | 1594 |
| CCA ACG GGA CAG TGG AAC CAG CCC ACT GAG GAA TGG TCA CTC CTG GCC<br>Pro Thr Gly Gln Trp Asn Gln Pro Thr Glu Glu Trp Ser Leu Leu Ala<br>                515                       520                    525 | 1642 |
| TTG AGC AGC TGC AGT GAC CTG GGA ATA TCT GAC TGG AGC TTT GCC CAT<br>Leu Ser Ser Cys Ser Asp Leu Gly Ile Ser Asp Trp Ser Phe Ala His<br>        530                       535                    540 | 1690 |
| GAC CTT GCC CCT CTA GGC TGT GTG GCA GCC CCA GGT GGT CTC CTG GGC<br>Asp Leu Ala Pro Leu Gly Cys Val Ala Ala Pro Gly Gly Leu Leu Gly<br>        545                       550                    555 | 1738 |
| AGC TTT AAC TCA GAC CTG GTC ACC CTG CCC CTC ATC TCT AGC CTG CAG<br>Ser Phe Asn Ser Asp Leu Val Thr Leu Pro Leu Ile Ser Ser Leu Gln<br>560                  565                       570                  575 | 1786 |

```
TCA AGT GAG TGACTCGGGC TGAGAGGCTG CTTTTGATTT TAGCCATGCC        1835
Ser Ser Glu

TGCTCCTCTG CCTGGACCAG GAGGAGGGCC CTGGGGCAGA AGTTAGGCAC GAGGCAGTCT 1895

GGGCACTTTT CTGCAAGTCC ACTGGGGCTG GCCCAGCCAG GCTGCAGGGC TGGTCAGGGT 1955

GTCTGGGGCA GGAGGAGGCC AACTCACTGA ACTAGTGCAG GGTATGTGGG TGGCACTGAC 2015

CTGTTCTGTT GACTGGGGCC CTGCAGACTC TGGCAGAGCT GAGAAGGGCA GGGACCTTCT 2075

CCCTCCTAGG AACTCTTTCC TGTATCATAA AGGATTATTT GCTCAGGGGA ACCATGGGGC 2135

TTTCTGGAGT TGTGGTGAGG CCACCAGGCT GAAGTCAGCT CAGACCCAGA CCTCCCTGCT 2195

TAGGCCACTC GAGCATCAGA GCTTCCAGCA GGAGGAAGGG CTGTAGGAAT GGAAGCTTCA 2255

GGGCCTTGCT GCTGGGGTCA TTTTTAGGGG AAAAAGGAGG ATATGATGGT CACATGGGGA 2315

ACCTCCCCTC ATCGGGCCTC TGGGGCAGGA AGCTTGTCAC TGGAAGATCT TAAGGTATAT 2375

ATTTTCTGGA CACTCAAACA CATCATAATG GATTCACTGA GGGGAGACAA AGGGAGCCGA 2435

GACCCTGGAT GGGGCTTCCA GCTCAGAACC CATCCCTCTG GTGGGTACCT CTGGCACCCA 2495

TCTGCAAATA TCTCCCTCTC TCCAACAAAT GGAGTAGCAT CCCCCTGGGG CACTTGCTGA 2555

GGCCAAGCCA CTCACATCCT CACTTTGCTG CCCCACCATC TTGCTGACAA CTTCCAGAGA 2615

AGCCATGGTT TTTTGTATTG GTCATAACTC AGCCCTTTGG GCGGCCTCTG GCTTGGGCA  2675

CCAGCTCATG CCAGCCCCAG AGGGTCAGGG TTGGAGGCCT GTGCTTGTGT TTGCTGCTAA 2735

TGTCCAGCTA CAGACCCAGA GGATAAGCCA CTGGGCACTG GCTGGGGTC CCTGCCTTGT  2795

TGGTGTTCAG CTGTGTGATT TTGGACTAGC CACTTGTCAG AGGGCCTCAA TCTCCCATCT 2855

GTGAAATAAG GACTCCACCT TTAGGGGACC CTCCATGTTT GCTGGGTATT AGCCAAGCTG 2915

GTCCTGGGAG AATGCAGATA CTGTCCGTGG ACTACCAAGC TGGCTTGTTT CTTATGCCAG 2975

AGGCTAACAG ATCCAATGGG AGTCCATGGT GTCATGCCAA GACAGTATCA GACACAGCCC 3035

CAGAAGGGGG CATTATGGGC CCTGCCTCCC CATAGGCCAT TTGGACTCTG CCTTCAAACA 3095

AAGGCAGTTC AGTCCACAGG CATGGAAGCT GTGAGGGGAC AGGCCTGTGC GTGCCATCCA 3155

GAGTCATCTC AGCCCTGCCT TTCTCTGGAG CATTCTGAAA ACAGATATTC TGGCCCAGGG 3215

AATCCAGCCA TGACCCCCAC CCCTCTGCCA AAGTACTCTT AGGTGCCAGT CTGGTAACTG 3275

AACTCCCTCT GGAGGCAGGC TTGAGGGAGG ATTCCTCAGG GTTCCCTTGA AAGCTTTATT 3335

TATTTATTTT GTTCATTTAT TTATTGGAGA GGCAGCATTG CACAGTGAAA GAATTCTGGA 3395

TATCTCAGGA GCCCCGAAAT TCTAGCTCTG ACTTTGCTGT TTCCAGTGGT ATGACCTTGG 3455

AGAAGTCACT TATCCTCTTG GAGCCTCAGT TTCCTCATCT GCAGAATAAT GACTGACTTG 3515

TCTAATTCAT AGGGATGTGA GGTTCTGCTG AGGAAATGGG TATGAATGTG CCTTGAACAC 3575

AAAGCTCTGT CAATAAGTGA TACATGTTTT TTATTCCAAT AAATTGTCAA GACCACA    3632

(2) INFORMATION FOR SEQ ID NO:2:

(i) SEQUENCE CHARACTERISTICS:
        (A) LENGTH: 578 amino acids
        (B) TYPE: amino acid
        (D) TOPOLOGY: linear (ii) MOLECULE TYPE: protein (xi) SEQUENCE DESCRIPTION: SEQ ID NO:2:

Met Leu Pro Cys Leu Val Val Leu Leu Ala Ala Leu Leu Ser Leu Arg
 1               5                  10                  15

Leu Gly Ser Asp Ala His Gly Thr Glu Leu Pro Ser Pro Pro Ser Val
                20                  25                  30
```

Trp Phe Glu Ala Glu Phe Phe His His Ile Leu His Trp Thr Pro Ile
        35                  40                  45

Pro Asn Gln Ser Glu Ser Thr Cys Tyr Glu Val Ala Leu Leu Arg Tyr
        50                  55                  60

Gly Ile Glu Ser Trp Asn Ser Ile Ser Asn Cys Ser Gln Thr Leu Ser
65                  70                  75                  80

Tyr Asp Leu Thr Ala Val Thr Leu Asp Leu Tyr His Ser Asn Gly Tyr
                85                  90                  95

Arg Ala Arg Val Arg Ala Val Asp Gly Ser Arg His Ser Asn Trp Thr
            100                 105                 110

Val Thr Asn Thr Arg Phe Ser Val Asp Glu Val Thr Leu Thr Val Gly
            115                 120                 125

Ser Val Asn Leu Glu Ile His Asn Gly Phe Ile Leu Gly Lys Ile Gln
            130                 135                 140

Leu Pro Arg Pro Lys Met Ala Pro Ala Asn Asp Thr Tyr Glu Ser Ile
145                 150                 155                 160

Phe Ser His Phe Arg Glu Tyr Glu Ile Ala Ile Arg Lys Val Pro Gly
                165                 170                 175

Asn Phe Thr Phe Thr His Lys Lys Val Lys His Glu Asn Phe Ser Leu
            180                 185                 190

Leu Thr Ser Gly Glu Val Gly Glu Phe Cys Val Gln Val Lys Pro Ser
            195                 200                 205

Val Ala Ser Arg Ser Asn Lys Gly Met Trp Ser Lys Glu Glu Cys Ile
            210                 215                 220

Ser Leu Thr Arg Gln Tyr Phe Thr Val Thr Asn Val Ile Ile Phe Phe
225                 230                 235                 240

Ala Phe Val Leu Leu Leu Ser Gly Ala Leu Ala Tyr Cys Leu Ala Leu
                245                 250                 255

Gln Leu Tyr Val Arg Arg Arg Lys Lys Leu Pro Ser Val Leu Leu Phe
            260                 265                 270

Lys Lys Pro Ser Pro Phe Ile Phe Ile Ser Gln Arg Pro Ser Pro Glu
            275                 280                 285

Thr Gln Asp Thr Ile His Pro Leu Asp Glu Glu Ala Phe Leu Lys Val
            290                 295                 300

Ser Pro Glu Leu Lys Asn Leu Asp Leu His Gly Ser Thr Asp Ser Gly
305                 310                 315                 320

Phe Gly Ser Thr Lys Pro Ser Leu Gln Thr Glu Glu Pro Gln Phe Leu
                325                 330                 335

Leu Pro Asp Pro His Pro Gln Ala Asp Arg Thr Leu Gly Asn Gly Glu
            340                 345                 350

Pro Pro Val Leu Gly Asp Ser Cys Ser Ser Gly Ser Ser Asn Ser Thr
            355                 360                 365

Asp Ser Gly Ile Cys Leu Gln Glu Pro Ser Leu Ser Pro Ser Thr Gly
            370                 375                 380

Pro Thr Trp Glu Gln Gln Val Gly Ser Asn Ser Arg Gly Gln Asp Asp
385                 390                 395                 400

Ser Gly Ile Asp Leu Val Gln Asn Ser Glu Gly Arg Ala Gly Asp Thr
                405                 410                 415

Gln Gly Gly Ser Ala Leu Gly His His Ser Pro Pro Glu Pro Glu Val
            420                 425                 430

Pro Gly Glu Glu Asp Pro Ala Ala Val Ala Phe Gln Gly Tyr Leu Arg
            435                 440                 445

Gln Thr Arg Cys Ala Glu Glu Lys Ala Thr Lys Thr Gly Cys Leu Glu

```
          450                 455                 460
Glu Glu Ser Pro Leu Thr Asp Gly Leu Gly Pro Lys Phe Gly Arg Cys
465                 470                 475                 480

Leu Val Asp Glu Ala Gly Leu His Pro Pro Ala Leu Ala Lys Gly Tyr
                485                 490                 495

Leu Lys Gln Asp Pro Leu Glu Met Thr Leu Ala Ser Ser Gly Ala Pro
                500                 505                 510

Thr Gly Gln Trp Asn Gln Pro Thr Glu Glu Trp Ser Leu Leu Ala Leu
            515                 520                 525

Ser Ser Cys Ser Asp Leu Gly Ile Ser Asp Trp Ser Phe Ala His Asp
530                 535                 540

Leu Ala Pro Leu Gly Cys Val Ala Ala Pro Gly Gly Leu Leu Gly Ser
545                 550                 555                 560

Phe Asn Ser Asp Leu Val Thr Leu Pro Leu Ile Ser Ser Leu Gln Ser
                565                 570                 575

Ser Glu (2) INFORMATION FOR SEQ ID NO:3:

(i) SEQUENCE CHARACTERISTICS:
        (A) LENGTH: 3520 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 80..1807

(xi) SEQUENCE DESCRIPTION: SEQ ID NO:3:

CCATTGTGCT GGAAAGCAGG ACGCGCCGGC CGGAGGCGTA AAGGCCGGCT CCAGTGGACG        60

ATGCCGCTGT GCGCCCAGG ATG TTG TCG CGT TTG CTC CCA TTC CTC GTC ACG       112
                     Met Leu Ser Arg Leu Leu Pro Phe Leu Val Thr
                       1               5                      10

ATC TCC AGC CTG AGC CTA GAA TTC ATT GCA TAC GGG ACA GAA CTG CCA        160
Ile Ser Ser Leu Ser Leu Glu Phe Ile Ala Tyr Gly Thr Glu Leu Pro
                 15                  20                  25

AGC CCT TCC TAT GTG TGG TTT GAA GCC AGA TTT TTC CAG CAC ATC CTC        208
Ser Pro Ser Tyr Val Trp Phe Glu Ala Arg Phe Phe Gln His Ile Leu
         30                  35                  40

CAC TGG AAA CCT ATC CCA AAC CAG TCT GAG AGC ACC TAC TAT GAA GTG        256
His Trp Lys Pro Ile Pro Asn Gln Ser Glu Ser Thr Tyr Tyr Glu Val
     45                  50                  55

GCC CTC AAA CAG TAC GGA AAC TCA ACC TGG AAT GAC ATC CAT ATC TGT        304
Ala Leu Lys Gln Tyr Gly Asn Ser Thr Trp Asn Asp Ile His Ile Cys
 60                  65                  70                  75

AGA AAG GCT CAG GCA TTG TCC TGT GAT CTC ACA ACG TTC ACC CTG GAT        352
Arg Lys Ala Gln Ala Leu Ser Cys Asp Leu Thr Thr Phe Thr Leu Asp
                 80                  85                  90

CTG TAT CAC CGA AGC TAT GGC TAC CGG GCC AGA GTC CGG GCA GTG GAC        400
Leu Tyr His Arg Ser Tyr Gly Tyr Arg Ala Arg Val Arg Ala Val Asp
             95                 100                 105

AAC AGT CAG TAC TCC AAC TGG ACC ACC ACT GAG ACT CGC TTC ACA GTG        448
Asn Ser Gln Tyr Ser Asn Trp Thr Thr Thr Glu Thr Arg Phe Thr Val
        110                 115                 120

GAT GAA GTG ATT CTG ACA GTG GAT AGC GTG ACT CTG AAA GCA ATG GAC        496
Asp Glu Val Ile Leu Thr Val Asp Ser Val Thr Leu Lys Ala Met Asp
    125                 130                 135
```

-continued

| | | |
|---|---|---|
| GGC ATC ATC TAT GGG ACA ATC CAT CCC CCC AGG CCC ACG ATA ACC CCT<br>Gly Ile Ile Tyr Gly Thr Ile His Pro Pro Arg Pro Thr Ile Thr Pro<br>140                           145                     150                         155 | 544 |
| GCA GGG GAT GAG TAC GAA CAA GTC TTC AAG GAT CTC CGA GTT TAC AAG<br>Ala Gly Asp Glu Tyr Glu Gln Val Phe Lys Asp Leu Arg Val Tyr Lys<br>                     160                       165                       170 | 592 |
| ATT TCC ATC CGG AAG TTC TCA GAA CTA AAG AAT GCA ACC AAG AGA GTG<br>Ile Ser Ile Arg Lys Phe Ser Glu Leu Lys Asn Ala Thr Lys Arg Val<br>             175                     180                     185 | 640 |
| AAA CAG GAA ACC TTC ACC CTC ACG GTC CCC ATA GGG GTG AGA AAG TTT<br>Lys Gln Glu Thr Phe Thr Leu Thr Val Pro Ile Gly Val Arg Lys Phe<br>       190                     195                     200 | 688 |
| TGT GTC AAG GTG CTG CCC CGC TTG GAA TCC CGA ATT AAC AAG GCA GAG<br>Cys Val Lys Val Leu Pro Arg Leu Glu Ser Arg Ile Asn Lys Ala Glu<br>205                         210                     215 | 736 |
| TGG TCG GAG GAG CAG TGT TTA CTT ATC ACG ACG GAG CAG TAT TTC ACT<br>Trp Ser Glu Glu Gln Cys Leu Leu Ile Thr Thr Glu Gln Tyr Phe Thr<br>220                         225                     230                     235 | 784 |
| GTG ACC AAC CTG AGC ATC TTA GTC ATA TCT ATG CTG CTA TTC TGT GGA<br>Val Thr Asn Leu Ser Ile Leu Val Ile Ser Met Leu Leu Phe Cys Gly<br>                     240                       245                     250 | 832 |
| ATC CTG GTC TGT CTG GTT CTC CAG TGG TAC ATC CGG CAC CCG GGG AAG<br>Ile Leu Val Cys Leu Val Leu Gln Trp Tyr Ile Arg His Pro Gly Lys<br>             255                     260                     265 | 880 |
| TTG CCT ACA GTC CTG GTC TTC AAG AAG CCT CAC GAC TTC TTC CCA GCC<br>Leu Pro Thr Val Leu Val Phe Lys Lys Pro His Asp Phe Phe Pro Ala<br>       270                     275                     280 | 928 |
| AAC CCT CTC TGC CCA GAA ACT CCC GAT GCC ATT CAC ATC GTG GAC CTG<br>Asn Pro Leu Cys Pro Glu Thr Pro Asp Ala Ile His Ile Val Asp Leu<br>285                         290                     295 | 976 |
| GAG GTT TTC CCA AAG GTG TCA CTA GAG CTG AGA GAC TCA GTC CTG CAT<br>Glu Val Phe Pro Lys Val Ser Leu Glu Leu Arg Asp Ser Val Leu His<br>300                         305                     310                     315 | 1024 |
| GGC AGC ACC GAC AGT GGC TTT GGC AGT GGT AAA CCA TCA CTT CAG ACT<br>Gly Ser Thr Asp Ser Gly Phe Gly Ser Gly Lys Pro Ser Leu Gln Thr<br>                     320                       325                     330 | 1072 |
| GAA GAG TCC CAA TTC CTC CTC CCT GGC TCC CAC CCC CAG ATA CAG GGG<br>Glu Glu Ser Gln Phe Leu Leu Pro Gly Ser His Pro Gln Ile Gln Gly<br>             335                     340                     345 | 1120 |
| ACT CTG GGA AAA GAA GAG TCT CCA GGG CTA CAG GCC ACC TGT GGG GAC<br>Thr Leu Gly Lys Glu Glu Ser Pro Gly Leu Gln Ala Thr Cys Gly Asp<br>       350                     355                     360 | 1168 |
| AAC ACG GAC AGT GGG ATC TGC CTG CAG GAG CCC GGC TTA CAC TCC AGC<br>Asn Thr Asp Ser Gly Ile Cys Leu Gln Glu Pro Gly Leu His Ser Ser<br>365                         370                     375 | 1216 |
| ATG GGG CCC GCC TGG AAG CAG CAG CTT GGA TAT ACC CAT CAG GAC CAG<br>Met Gly Pro Ala Trp Lys Gln Gln Leu Gly Tyr Thr His Gln Asp Gln<br>380                         385                     390                     395 | 1264 |
| GAT GAC AGT GAC GTT AAC CTA GTC CAG AAC TCT CCA GGG CAG CCT AAG<br>Asp Asp Ser Asp Val Asn Leu Val Gln Asn Ser Pro Gly Gln Pro Lys<br>                     400                       405                     410 | 1312 |
| TAC ACA CAG GAT GCA TCT GCC TTG GGC CAT GTC TGT CTC CTA GAA CCT<br>Tyr Thr Gln Asp Ala Ser Ala Leu Gly His Val Cys Leu Leu Glu Pro<br>             415                     420                     425 | 1360 |
| AAA GCC CCT GAG GAG AAA GAC CAA GTC ATG GTG ACA TTC CAG GGC TAC<br>Lys Ala Pro Glu Glu Lys Asp Gln Val Met Val Thr Phe Gln Gly Tyr<br>       430                     435                     440 | 1408 |
| CAG AAA CAG ACC AGA TGG AAG GCA GAG GCA GCA GGC CCA GCA GAA TGC<br>Gln Lys Gln Thr Arg Trp Lys Ala Glu Ala Ala Gly Pro Ala Glu Cys<br>445                         450                     455 | 1456 |

```
TTG GAC GAA GAG ATT CCC TTG ACA GAT GCC TTT GAT CCT GAA CTT GGG      1504
Leu Asp Glu Glu Ile Pro Leu Thr Asp Ala Phe Asp Pro Glu Leu Gly
460                 465                 470                 475

GTA CAC CTG CAG GAT GAT TTG GCT TGG CCT CCA CCA GCT CTG GCC GCA      1552
Val His Leu Gln Asp Asp Leu Ala Trp Pro Pro Pro Ala Leu Ala Ala
                480                 485                 490

GGT TAT TTG AAA CAG GAG TCT CAA GGG ATG GCT TCT GCT CCA CCA GGG      1600
Gly Tyr Leu Lys Gln Glu Ser Gln Gly Met Ala Ser Ala Pro Pro Gly
            495                 500                 505

ACA CCA AGT AGA CAG TGG AAT CAA CTG ACC GAA GAG TGG TCA CTC CTG      1648
Thr Pro Ser Arg Gln Trp Asn Gln Leu Thr Glu Glu Trp Ser Leu Leu
        510                 515                 520

GGT GTG GTT AGC TGT GAA GAT CTA AGC ATA GAA AGT TGG AGG TTT GCC      1696
Gly Val Val Ser Cys Glu Asp Leu Ser Ile Glu Ser Trp Arg Phe Ala
    525                 530                 535

CAT AAA CTT GAC CCT CTG GAC TGT GGG GCA GCC CCT GGT GGC CTC CTG      1744
His Lys Leu Asp Pro Leu Asp Cys Gly Ala Ala Pro Gly Gly Leu Leu
540                 545                 550                 555

GAT AGC CTT GGC TCT AAC CTG GTC ACC CTG CCG TTG ATC TCC AGC CTG      1792
Asp Ser Leu Gly Ser Asn Leu Val Thr Leu Pro Leu Ile Ser Ser Leu
                560                 565                 570

CAG GTA GAA GAA TGACAGCGGC TAAGAGTTAT TTGTATTCCA GCCATGCCTG          1844
Gln Val Glu Glu
            575

CTCCCCTCCC TGTACCTGGG AGGCTCAGGA GTCAAAGAAA TATGTGGGTC CTTTTCTGCA    1904

GACCTACTGT GACCAGCTAG CCAGGCTCCA CGGGGCAAGG AAAGGCCATC TTGATACACG    1964

AGTGTCAGGT ACATGAGAGG TTGTGGCTAG TCTGCTGAGT GAGGGTCTGT AGATACCAGC    2024

AGAGCTGAGC AGGATTGACA GAGACCTCCT CATGCCTCAG GGCTGGCTCC TACACTGGAA    2084

GGACCTGTGT TTGGGTGTAA CCTCAGGGCT TTCTGGATGT GGTAAGACTG TAGGTCTGAA    2144

GTCAGCTGAG CCTGGATGTC TGCGGAGGTG TTGGAGTGGC TAGCCTGCTA CAGGATAAAG    2204

GGAAGGCTCA AGAGATAGAA GGGCAGAGCA TGAGCCAGGT TTAATTTTGT CCTGTAGAGA    2264

TGGTCCCCAG CCAGGATGGG TTACTTGTGG CTGGAGATC TTGGGGTATA CACCACCCTG     2324

AATGATCAGC CAGTCAATTC AGAGCTGTGT GGCAAAAGGG ACTGAGACCC AGAATTTCTG    2384

TTCCTCTTGT GAGGTGTCTC TGCTACCCAT CTGCAGACAC ACATCTTCAT CTTTTTACTA    2444

TGGCTGTGTC CCCTGAATTA CCAGCAGTGG CCAAGCCATT ACTCCCTGCT GCTCACTGTT    2504

GTGACGTCAG ACCAGACCAG ACGCTGTCTG TCTGTGTTAG TACACTACCC TTTAGGTGGC    2564

CTTTGGGCTT GAGCACTGGC CCAGGCTTAG GACTTATGTC TGCTTTTGCT GCTAATCTCT    2624

AACTGCAGAC CCAGAGAACA GGGTGCTGGG CTGACACCTC CGTGTTCAGC TGTGTGACCT    2684

CCGACCAGCA GCTTCCTCAG GGGACTAAAA TAATGACTAG GTCATTCAGA AGTCCCTCAT    2744

GCTGAATGTT AACCAAGGTG CCCCTGGGGT GATAGTTTAG GTCCTGCAAC CTCTGGGTTG    2804

GAAGGAAGTG GACTACGGAA GCCATCTGTC CCCCTGGGGA GCTTCCACCT CATGCCAGTG    2864

TTTCAGAGAT CTTGTGGGAG CCTAGGGCCT TGTGCCAAGG GAGCTGCTAG TCCCTGGGGT    2924

CTAGGGCTGG TCCCTGCCTC CCTATACTGC GTTTGAGACC TGTCTTCAAA TGGAGGCAGT    2984

TTGCAGCCCC TAAGCAAGGA TGCTGAGAGA AGCAGCAAGG CTGCTGATCC CTGAGCCCAG    3044

AGTTTCTCTG AAGCTTTCCA AATACAGACT GTGTGACGGG GTGAGGCCAG CCATGAACTT    3104

TGGCATCCTG CCGAGAAGGT CATGACCCTA ATCTGGTACG AGAGCTCCTT CTGGAACTGG    3164

GCAAGCTCTT TGAGACCCCC CTGGAACCTT TATTTATTTA TTTGCTCACT TATTTATTGA    3224

GGAAGCAGCG TGGCACAGGC GCAAGGCTCT GGGTCTCTCA GGAGGTCTAG ATTTGCCTGC    3284
```

```
CCTGTTTCTA GCTGTGTGAC CTTGGGCAAG TCACGTTTCC TCGTGGAGCC TCAGTTTTCC      3344

TGTCTGTATG CAAAGCTTGG AAATTGAAAT GTACCTGACG TGCTCCATCC CTAGGAGTGC      3404

TGAGTCCCAC TGAGAAAGCG GGCACAGACG CCTCAAATGG AACCACAAGT GGTGTGTGTT      3464

TTCATCCTAA TAAAAGTCA GGTGTTTTGT GGAAAAAAAA AAAAAAAAAA AAAAAA          3520
```

(2) INFORMATION FOR SEQ ID NO:4:

(i) SEQUENCE CHARACTERISTICS:
        (A) LENGTH: 575 amino acids
        (B) TYPE: amino acid
        (D) TOPOLOGY: linear (ii) MOLECULE TYPE: protein (xi) SEQUENCE DESCRIPTION: SEQ ID NO:4:

```
Met Leu Ser Arg Leu Leu Pro Phe Leu Val Thr Ile Ser Ser Leu Ser
 1               5                  10                  15

Leu Glu Phe Ile Ala Tyr Gly Thr Glu Leu Pro Ser Pro Ser Tyr Val
                 20                  25                  30

Trp Phe Glu Ala Arg Phe Phe Gln His Ile Leu His Trp Lys Pro Ile
             35                  40                  45

Pro Asn Gln Ser Glu Ser Thr Tyr Tyr Glu Val Ala Leu Lys Gln Tyr
         50                  55                  60

Gly Asn Ser Thr Trp Asn Asp Ile His Ile Cys Arg Lys Ala Gln Ala
 65                  70                  75                  80

Leu Ser Cys Asp Leu Thr Thr Phe Thr Leu Asp Leu Tyr His Arg Ser
                 85                  90                  95

Tyr Gly Tyr Arg Ala Arg Val Arg Ala Val Asp Asn Ser Gln Tyr Ser
             100                 105                 110

Asn Trp Thr Thr Thr Glu Thr Arg Phe Thr Val Asp Glu Val Ile Leu
         115                 120                 125

Thr Val Asp Ser Val Thr Leu Lys Ala Met Asp Gly Ile Ile Tyr Gly
130                 135                 140

Thr Ile His Pro Arg Pro Thr Ile Thr Pro Ala Gly Asp Glu Tyr
145                 150                 155                 160

Glu Gln Val Phe Lys Asp Leu Arg Val Tyr Lys Ile Ser Ile Arg Lys
                 165                 170                 175

Phe Ser Glu Leu Lys Asn Ala Thr Lys Arg Val Lys Gln Glu Thr Phe
             180                 185                 190

Thr Leu Thr Val Pro Ile Gly Val Arg Lys Phe Cys Val Lys Val Leu
         195                 200                 205

Pro Arg Leu Glu Ser Arg Ile Asn Lys Ala Glu Trp Ser Glu Glu Gln
210                 215                 220

Cys Leu Leu Ile Thr Thr Glu Gln Tyr Phe Thr Val Thr Asn Leu Ser
225                 230                 235                 240

Ile Leu Val Ile Ser Met Leu Leu Phe Cys Gly Ile Leu Val Cys Leu
                 245                 250                 255

Val Leu Gln Trp Tyr Ile Arg His Pro Gly Lys Leu Pro Thr Val Leu
             260                 265                 270

Val Phe Lys Lys Pro His Asp Phe Phe Pro Ala Asn Pro Leu Cys Pro
         275                 280                 285

Glu Thr Pro Asp Ala Ile His Ile Val Asp Leu Glu Val Phe Pro Lys
     290                 295                 300

Val Ser Leu Glu Leu Arg Asp Ser Val Leu His Gly Ser Thr Asp Ser
305                 310                 315                 320
```

```
Gly Phe Gly Ser Gly Lys Pro Ser Leu Gln Thr Glu Ser Gln Phe
                325                 330             335

Leu Leu Pro Gly Ser His Pro Gln Ile Gln Gly Thr Leu Gly Lys Glu
            340             345             350

Glu Ser Pro Gly Leu Gln Ala Thr Cys Gly Asp Asn Thr Asp Ser Gly
        355             360                 365

Ile Cys Leu Gln Glu Pro Gly Leu His Ser Ser Met Gly Pro Ala Trp
    370             375                 380

Lys Gln Gln Leu Gly Tyr Thr His Gln Asp Gln Asp Asp Ser Asp Val
385             390             395                     400

Asn Leu Val Gln Asn Ser Pro Gly Gln Pro Lys Tyr Thr Gln Asp Ala
                405             410                 415

Ser Ala Leu Gly His Val Cys Leu Leu Glu Pro Lys Ala Pro Glu Glu
                420             425             430

Lys Asp Gln Val Met Val Thr Phe Gln Gly Tyr Gln Lys Gln Thr Arg
            435             440             445

Trp Lys Ala Glu Ala Ala Gly Pro Ala Glu Cys Leu Asp Glu Glu Ile
        450             455             460

Pro Leu Thr Asp Ala Phe Asp Pro Glu Leu Gly Val His Leu Gln Asp
465             470             475                     480

Asp Leu Ala Trp Pro Pro Pro Ala Leu Ala Ala Gly Tyr Leu Lys Gln
                485             490                 495

Glu Ser Gln Gly Met Ala Ser Ala Pro Pro Gly Thr Pro Ser Arg Gln
            500             505             510

Trp Asn Gln Leu Thr Glu Glu Trp Ser Leu Leu Gly Val Val Ser Cys
        515             520             525

Glu Asp Leu Ser Ile Glu Ser Trp Arg Phe Ala His Lys Leu Asp Pro
    530             535             540

Leu Asp Cys Gly Ala Ala Pro Gly Gly Leu Leu Asp Ser Leu Gly Ser
545             550             555                     560

Asn Leu Val Thr Leu Pro Leu Ile Ser Ser Leu Gln Val Glu Glu
                565             570             575
```